US007557261B2

(12) United States Patent
Spangenberg et al.

(10) Patent No.: US 7,557,261 B2

(45) Date of Patent: Jul. 7, 2009

(54) MODIFICATION OF FRUCTAN BIOSYNTHESIS

(75) Inventors: German Carlos Spangenberg, Bundoora (AU); Angela Jane Lidgett, Richmond (AU); Xenie Angela Johnson, Collingwood (AU); Katherine Terdich, East Ivanhoe (AU)

(73) Assignee: Molecular Plant Breeding Nominees Ltd., Glen Osmond (AU)

( * ) Notice: Subject to any disclaimer, the term of this patent is extended or adjusted under 35 U.S.C. 154(b) by 888 days.

(21) Appl. No.: 10/311,193

(22) PCT Filed: Jun. 14, 2001

(86) PCT No.: PCT/AU01/00705

§ 371 (c)(1), (2), (4) Date: Jun. 30, 2003

(87) PCT Pub. No.: WO01/95691

PCT Pub. Date: Dec. 20, 2001

(65) Prior Publication Data

US 2005/0089845 A1 Apr. 28, 2005

(30) Foreign Application Priority Data

Jun. 14, 2002 (AU) .................................... PQ8155

(51) Int. Cl.

| | |
|---|---|
| ***C12N 15/82*** | (2006.01) |
| ***C12N 15/29*** | (2006.01) |
| ***C12N 15/52*** | (2006.01) |
| ***A01H 5/00*** | (2006.01) |
| ***A01H 5/10*** | (2006.01) |

(52) U.S. Cl. ....................... 800/284; 800/278; 800/295; 800/298; 435/320.1; 435/468; 435/193; 536/23.1; 536/23.2; 536/23.6

(58) Field of Classification Search ....................... None
See application file for complete search history.

(56) References Cited

U.S. PATENT DOCUMENTS 6,057,494 A * 5/2000 Koops et al. ................ 800/284

FOREIGN PATENT DOCUMENTS

| | | | |
|---|---|---|---|
| WO | WO/ 94/14970 | | 7/1994 |
| WO | WO 95/13389 | * | 5/1995 |
| WO | WO 98/39460 | | 9/1998 |
| WO | WO 99/46395 | | 9/1999 |

OTHER PUBLICATIONS

Vergauwen et al Plant Physiology 2003, 133:391-401.*

Ritsema et al 2004 Plant Molecular Biology 54:853-863.*

Turk et al 1997 New Phytology 136:29-38.*

French, S. et al. Journal of Molecular Evolution; 1983, vol. 19, pp. 171-175.*

Lüscher, M. et al., "Cloning and Functional Analysis of Sucrose: Sucrose I -Fructosyltransferase from Tall Fescue," *Plant Physiology*, 124:1217-1227, Nov. 2000.

Lüscher, M. and Nelson, C. J., "Fructosyltransferase Activities in the Leaf Growth Zone of Tall Fescue," *Plant Physiology*, 107:1419-1425, 1995.

St. John, J. A. et al., "A fructan: fructan fructosyltransferase activity from *Lolium rigidum*," *New Phytol.*, 135:235-247, 1997.

St. John, J. A. et al., "Synthesis of fructans by partially purifed fructosyltransferase activities from *Lolium rigidum*," *New Phytol.*, 136:39-51, 1997.

Vijn, I. et al., "Expression of fructosyltransferase genes in transgenic plants," *Proc. Phyto. Soc. Eur.*, (Regulation of Primary Metabolic Pathways in Plants), 42:Chapter 11:227-237, 1999.

van der Meer, I. M. et al., "Cloning of the fructan biosynthesis pathway of Jerusalem artichoke," *The Plant Journal*, 15(4):489-500, 1998.

Sprenger, N. et al., "Purification, cloning, and functional expression of sucrose: fructan 6-fructosyltransferase, a key enzyme of fructan synthesis in barley," *Proc. Natl. Acad. Sci. USA*, 92:11652-11656, Dec. 1995.

"Hordeum vulgare mRNA for sucrose:fructan 6-fructosyltransferase," Database EMBL 'Online!' Jan. 22, 1996, XP 002336247.

"Triticum aestivum vacuolar invertase (WVRV) mRNA, partial cds.," Database EMBL 'Online!' Jun. 17, 1998, XP002336248.

Irma Vijn, et al., "Cloning of Sucrose:Sucrose I-Fructosyltransferase from Onion and Synthesis of Structurally Defined Fructan Molecules from Sucrose," Plant Physiology, American Society of Plant Physiologists, vol. 117, No. 4, 1998, pp. 1507-1513, XP002970800.

Supplementary European Search Report dated Aug. 8, 2005.

* cited by examiner

*Primary Examiner*—Russell Kallis
*Assistant Examiner*—Brent Page
(74) *Attorney, Agent, or Firm*—Larson & Anderson, LLC

(57) ABSTRACT

The present invention relates to the modification of fructan biosynthesis in plants and, more particularly, to enzymes involved in the fructan biosynthetic pathway and nucleic acids encoding such enzymes. The present invention also relates to regulatory elements and, more particularly, to promoters capable of causing expression of an exogenous gene in plant cells, such promoters being from a gene encoding an enzyme involved in the fructan biosynthetic pathway in plants. The invention also relates to vectors including the nucleic acids and regulatory elements of the invention, plant cells, plants, seeds and other plant parts transformed with the regulatory elements, nucleic acids and vectors, and methods of using the nucleic acids, regulatory elements and vectors.

17 Claims, 55 Drawing Sheets

```
       GGCACGAGATCTGCTCCATTTGTTTTGGAATTCGCCGACGATCGATGGAGTCTCGGTCCA
    1  ---------+---------+---------+---------+---------+---------+  60
                                                 M  E  S  R  S  I

       TTCCCGGCGCGTACGCGTACGAGCCGCTGCCCCACTCCTCCGACGACGCCCATGGCCACG
   61  ---------+---------+---------+---------+---------+---------+  120
        P  G  A  Y  A  Y  E  P  L  P  H  S  S  D  D  A  H  G  H  D

       ACGACCGCCGGAGCGCCGGCGGCGTGAGGTGGCGCGCGTGCGCGGCCGTTCTTGCGGCGT
  121  ---------+---------+---------+---------+---------+---------+  180
        D  R  R  S  A  G  G  V  R  W  R  A  C  A  A  V  L  A  A  S

       CTGCCCTGGTTGTGTTCGTGGTCGCCAGCACGCTCGCCGGGTCAAGGGTGGACCGCGTGG
  181  ---------+---------+---------+---------+---------+---------+  240
        A  L  V  V  F  V  V  A  S  T  L  A  G  S  R  V  D  R  V  A

       CCGTGGACGTGGCTGCCATGCCGGCGCTGTCGGAGACGGCGAGGAGCCGTGGGAAGGACG
  241  ---------+---------+---------+---------+---------+---------+  300
        V  D  V  A  A  M  P  A  L  S  E  T  A  R  S  R  G  K  D  A

       CGGGCGTGTCGGAGAAGACGTCCGGCGCGGCGGACGAGATGGGGTTCCTCGGCGCCGGCT
  301  ---------+---------+---------+---------+---------+---------+  360
        G  V  S  E  K  T  S  G  A  A  D  E  M  G  F  L  G  A  G  S

       CCGGCGCCGACGCCGACGGGTTCCCGTGGAGCAACGCCATGCTGCAGTGGCAGCGCACGG
  361  ---------+---------+---------+---------+---------+---------+  420
        G  A  D  A  D  G  F  P  W  S  N  A  M  L  Q  W  Q  R  T  G

       GTTTCCATTTCCAGCCCGAGATGAACTGGATGAACGATCCCAACGGTCCGGTGTATTACC
  421  ---------+---------+---------+---------+---------+---------+  480
        F  H  F  Q  P  E  M  N  W  M  N  D  P  N  G  P  V  Y  Y  R

       GAGGATGGTACCACCTCTTCTACCAgTACAACCCCGAGGGGGCGGTGTGGGGCAACATCG
  481  ---------+---------+---------+---------+---------+---------+  540
        G  W  Y  H  L  F  Y  Q  Y  N  P  E  G  A  V  W  G  N  I  A

       CGTGGGGCCACGCCGTGTCCCGGGACCTGGTCCACTGGCGCCACCTCCCGCTCGCCATGG
  541  ---------+---------+---------+---------+---------+---------+  600
        W  G  H  A  V  S  R  D  L  V  H  W  R  H  L  P  L  A  M  V

       TGCCTGACCAATGGTACGACATCAACGGTGTCTGGACGGGCTCCGCCACTGTGTTCCCCG
  601  ---------+---------+---------+---------+---------+---------+  660
        P  D  Q  W  Y  D  I  N  G  V  W  T  G  S  A  T  V  F  P  D

       ATGGGACCCTCAACATGCTCTACACGGGGTCCACCAACGCCTCCGTGCAGGTTCAGTGCC
  661  ---------+---------+---------+---------+---------+---------+  720
        G  T  L  N  M  L  Y  T  G  S  T  N  A  S  V  Q  V  Q  C  L
```

FIGURE 1

```
        TTGCTGTGCCCGAGGACCCCAACGACTCCCTCCTCCGCAACTGGACAAAGCACGAAGCTA
 721    ---------+---------+---------+---------+---------+---------+    780
          A  V  P  E  D  P  N  D  S  L  L  R  N  W  T  K  H  E  A  N

        ACCCCGTGCTCCTACCGCCGCCCGGGATCGGCGACAAGGACTTCCGTGACCCGACCACCG
 781    ---------+---------+---------+---------+---------+---------+    840
          P  V  L  L  P  P  P  G  I  G  D  K  D  F  R  D  P  T  T  A

        CCTGGTTCGACGAGTCCGACCAGACGTGGCGCACCGTCATCGGGTCCAAGGACAACAACG
 841    ---------+---------+---------+---------+---------+---------+    900
          W  F  D  E  S  D  Q  T  W  R  T  V  I  G  S  K  D  N  N  G

        GCCACGcCGGTATTGCCATGGTGTACAAGACCAAGGACTTCCTCAACTACGAGCTCATCC
 901    ---------+---------+---------+---------+---------+---------+    960
          H  A  G  I  A  M  V  Y  K  T  K  D  F  L  N  Y  E  L  I  P

        CGGGATACTTGCATCGCGTCGACGGCACCGGCATGTGGGAGTGCATCGACTTCTACCCCG
 961    ---------+---------+---------+---------+---------+---------+    1020
          G  Y  L  H  R  V  D  G  T  G  M  W  E  C  I  D  F  Y  P  V

        TCGGAGGCAAAAACGGCAGCGAGGAGTTGTACGTGATCAAGGAGAGCAGCGACGACGACC
1021    ---------+---------+---------+---------+---------+---------+    1080
          G  G  K  N  G  S  E  E  L  Y  V  I  K  E  S  S  D  D  D  R

        GACATGACTGGTACACGCTAGGGAAATACGACGCGGCAGCCAACACGTTCACGGCCGCGG
1081    ---------+---------+---------+---------+---------+---------+    1140
          H  D  W  Y  T  L  G  K  Y  D  A  A  A  N  T  F  T  A  A  D

        ACCCGGAGAACGACCTAGGGATTGGGTTGAGGTATGACTGGGGCAAGTTCTACGCGACCA
1141    ---------+---------+---------+---------+---------+---------+    1200
          P  E  N  D  L  G  I  G  L  R  Y  D  W  G  K  F  Y  A  T  K

        AGACTTTCTACGACCCGGCCAAGAATCGGCGCGTGCTCTGGGGATGGATCGGCGAGACCG
1201    ---------+---------+---------+---------+---------+---------+    1260
          T  F  Y  D  P  A  K  N  R  R  V  L  W  G  W  I  G  E  T  D

        ACTCTGAGCGCGCCGATGTCGCCAAGGGATGGGCATCCCTCATGTCGATTCCGAGGACGG
1261    ---------+---------+---------+---------+---------+---------+    1320
          S  E  R  A  D  V  A  K  G  W  A  S  L  M  S  I  P  R  T  V

        TGGAACTCGACGAGAAGACCCGGACCAACCTCATCCAATGGCCGGTGGAGGAGCTCGAGA
1321    ---------+---------+---------+---------+---------+---------+    1380
          E  L  D  E  K  T  R  T  N  L  I  Q  W  P  V  E  E  L  E  T

        CCCTCCGCATCAAGTCCACCGACCTCGGTGGCGTCACCATCGACCACGGCAGCGTCTACC
1381    ---------+---------+---------+---------+---------+---------+    1440
          L  R  I  K  S  T  D  L  G  G  V  T  I  D  H  G  S  V  Y  P
```

FIGURE 1 CONTINUED

```
       CACTCCCTCTCCACCGCGCCACACAACTCGACATTGAGGCCTCCTTCCGCATCGACACTG
1441   ---------+---------+---------+---------+---------+---------+   1500
         L  P  L  H  R  A  T  Q  L  D  I  E  A  S  F  R  I  D  T  A

       CCACCGTCGCTGCCCTCAATGAGGCTGACGTTGGCTACAATTGCAGCACCAGCGGTGGCT
1501   ---------+---------+---------+---------+---------+---------+   1560
          T  V  A  A  L  N  E  A  D  V  G  Y  N  C  S  T  S  G  G  S

       CTGCCAACCGTGGCGCACTCGGCCCCTTTGGCCTCCTCGTCCTCGCCGACGGTAAGGCAG
1561   ---------+---------+---------+---------+---------+---------+   1620
         A  N  R  G  A  L  G  P  F  G  L  L  V  L  A  D  G  K  A  E

       AGCAGACGGCAGTGTACTTCTATGTGGCCAAGGGCCTCGACGGGACCCTCCAAACCCACT
1621   ---------+---------+---------+---------+---------+---------+   1680
           Q  T  A  V  Y  F  Y  V  A  K  G  L  D  G  T  L  Q  T  H  F

       TCTGCCACGACGAGTCACGGTCGACGCTTGCTAGGGATGTTGTGAAGCGGGTGGTGGGAT
1681   ---------+---------+---------+---------+---------+---------+   1740
            C  H  D  E  S  R  S  T  L  A  R  D  V  V  K  R  V  V  G  Y

       ACACCGTGCCTGTCCTCGACGGTGAGGCCTTCTCCGTCAGGGTGCTCGTGGACCACTCAA
1741   ---------+---------+---------+---------+---------+---------+   1800
          T  V  P  V  L  D  G  E  A  F  S  V  R  V  L  V  D  H  S  I

       TCGTGGAGAGcTTCGCCATGGGCGGCAGGTCCACGGCAACATCGAGGGTGTACCCAACGG
1801   ---------+---------+---------+---------+---------+---------+   1860
           V  E  S  F  A  M  G  G  R  S  T  A  T  S  R  V  Y  P  T  E

       AGGCCATCTATGGCGCTGCCGGTGCGTATCTTTTCAACAACGCCACCGGCGGCTCCGTCA
1861   ---------+---------+---------+---------+---------+---------+   1920
             A  I  Y  G  A  A  G  A  Y  L  F  N  N  A  T  G  G  S  V  T

       CCGTTGAGAAGCTCGTGGTGCATGAGATGGACTCGTCCTACAACCAGATCTTCATGGCTG
1921   ---------+---------+---------+---------+---------+---------+   1980
            V  E  K  L  V  V  H  E  M  D  S  S  Y  N  Q  I  F  M  A  D

       ACGACTTGTAGTCATCGTCGTCCATGGATAGCGCGCGCGGATGGTGAGGATGATCACCTA
1981   ---------+---------+---------+---------+---------+---------+   2040
           D  L

       CTACATATACATACATACTATTGATCGAGCGATCACCACATCGGTCGGTGGCGGCTTCCT
2041   ---------+---------+---------+---------+---------+---------+   2100

       CTTcTCTTGGATGCAGAAGGAGATGGAGTACTAGCTACTCTATTTACCATGTTGTTTTGT
2101   ---------+---------+---------+---------+---------+---------+   2160
```

FIGURE 1 CONTINUED

```
     TGGTTTTTTTGGGTTTTGGGTTTTTGACGAGATGGATGAATTAGCTATAGATGGACGATT
2161 ---------+---------+---------+---------+---------+---------+ 2220

     GTGTCCTATTTATCTCCTGCCTTCCGAGTGTAACTATACATATATTGGCAGGATCGATGA
2221 ---------+---------+---------+---------+---------+---------+ 2280

     TATCCCTACTGCATGACAGTCATGATTAATTATTGTGATGATATTGATCAATCAACTTGT
2281 ---------+---------+---------+---------+---------+---------+ 2340

     AAATGAATTTATTGGGGGAAAGGTTTATGAAAAAAAAAAAAAAAAA
2341 ---------+---------+---------+---------+------ 2386
```

FIGURE 1 CONTINUED

```
      GGCACGAGCTTGTCTAATCCCTCCCTCGCACTAGTCGGCCGAGGCATTCTTCCTAGTTGC
  1   ---------+---------+---------+---------+---------+---------+   60

      TTCCATCGCATCGATCTCGATCCACAGATTCTATGCCAATGGAGGCAAGAGATGGCGTCT
 61   ---------+---------+---------+---------+---------+---------+   120
                                      M  P  M  E  A  R  D  G  V  S

      CGATGCCCTACTCGTATGCGGCCCTGCCGGAGGACGCCGAGGCAGCGGTGGTTGGGCGCG
121   ---------+---------+---------+---------+---------+---------+   180
        M  P  Y  S  Y  A  A  L  P  E  D  A  E  A  A  V  V  G  R  G

      GTCGCCGGACCGGGCCTCTGTTCGCAGCGTTGCTGTTGACGTTGGTCGCCGCGCTCCTTG
181   ---------+---------+---------+---------+---------+---------+   240
        R  R  T  G  P  L  F  A  A  L  L  L  T  L  V  A  A  L  L  A

      CCGTCGCCGCGCTGGCTGGCGTCAGGCTCGTTGGCGAGCTGCCTGCCGGGGGCGTCkTCA
241   ---------+---------+---------+---------+---------+---------+   300
        V  A  A  L  A  G  V  R  L  V  G  E  L  P  A  G  G  V  X  M

      TGCCCAACCACCCGATGGAAGTCATGGACGTCAGCGGTAGCAGAGGGCCTGAGTCAGGCG
301   ---------+---------+---------+---------+---------+---------+   360
        P  N  H  P  M  E  V  M  D  V  S  G  S  R  G  P  E  S  G  V

      TGTCGGAGAAGACGTCCGGGGCCGCCAGCGAGAGCGGCGGCATGCTGGGCGCCGACGCCG
361   ---------+---------+---------+---------+---------+---------+   420
        S  E  K  T  S  G  A  A  S  E  S  G  G  M  L  G  A  D  A  G

      GCAGCAACGCGTTCCCGTGGAGCAATGCGATGCTCCAGTGGCAGCGCACCGGCTTCCACT
421   ---------+---------+---------+---------+---------+---------+   480
        S  N  A  F  P  W  S  N  A  M  L  Q  W  Q  R  T  G  F  H  F

      TCCAGCCCGAGAAGAACTGGATGAACGACCCCAACGGTCCGGTCTACTACAAGGGGTGGT
481   ---------+---------+---------+-------------------+---------+   540
        Q  P  E  K  N  W  M  N  D  P  N  G  P  V  Y  Y  K  G  W  Y

      ACCACCTCTTCTACCAGTACAACCCGGAGGGCGCAATCTGGGGCAACAAGATCGCGTGGG
541   ---------+---------+---------+---------+---------+---------+   600
        H  L  F  Y  Q  Y  N  P  E  G  A  I  W  G  N  K  I  A  W  G

      GCCATGCCGTGTCCCGGGACATGCTCCGGTGGCGCCACCTGCCCATCGCCATGTTCCCCG
601   ---------+---------+---------+---------+---------+---------+   660
        H  A  V  S  R  D  M  L  R  W  R  H  L  P  I  A  M  F  P  D

      ACCAGTGGTACGACATCAACGGCGCATGGTCAGGCTCCGCCACCGTGCTCCCCGACGGCC
661   ---------+---------+---------+---------+---------+---------+   720
        Q  W  Y  D  I  N  G  A  W  S  G  S  A  T  V  L  P  D  G  R
```

FIGURE 2

```
      GCATCGTCATGCTCTACACGGGCTCCACCAACGCCTCCGTGCAGGTCCAGTGCCTCGCCT
721   ---------+---------+---------+---------+---------+---------+   780
        I  V  M  L  Y  T  G  S  T  N  A  S  V  Q  V  Q  C  L  A  F

      TCCCCTCCGACCCCTCCGACCCGCTGCTCACCAACTGGACCAAGTATGAGGGCAACCCGG
781   ---------+---------+---------+---------+---------+---------+   840
        P  S  D  P  S  D  P  L  L  T  N  W  T  K  Y  E  G  N  P  V

      TGCTGTACCCGCCTCCGCACGTCGGGGAGAAGGACTTCCGGGACCCGACCACTGCATGGT
841   ---------+---------+---------+---------+---------+---------+   900
        L  Y  P  P  P  H  V  G  E  K  D  F  R  D  P  T  T  A  W  Y

      ACGATGGCTCCGATGGAATGTGGCGGATCGTCATCGGGTCCAAGGATAACCGCCGCGCCG
901   ---------+---------+---------+---------+---------+---------+   960
        D  G  S  D  G  M  W  R  I  V  I  G  S  K  D  N  R  R  A  G

      GCATGGCCTTGACCTACAAGACCAAGAACTTCCATGATTTTGAGCTCGTTCCCGGAGTGC
961   ---------+---------+---------+---------+---------+---------+   1020
        M  A  L  T  Y  K  T  K  N  F  H  D  F  E  L  V  P  G  V  L

      TGCACCGGGTGCCGGCGACGGGGATGTGGGAGTGCATCGATTTGTACCCGGTTGGCGGCG
1021  ---------+---------+---------+---------+---------+---------+   1080
        H  R  V  P  A  T  G  M  W  E  C  I  D  L  Y  P  V  G  G  A

      CGAGGGGCATTGACATGACGGAGGCCGTTGCGGCGGCATCCAACAGCGGTGGTGGTGAAG
1081  ---------+---------+---------+---------+---------+---------+   1140
        R  G  I  D  M  T  E  A  V  A  A  A  S  N  S  G  G  G  E  V

      TTTTGCATGTCATGAAGGAGAGCTCAGACGACGACCGACATGACTACTACGCGCTAGGGA
1141  ---------+---------+---------+---------+---------+---------+   1200
        L  H  V  M  K  E  S  S  D  D  D  R  H  D  Y  Y  A  L  G  R

      GGTACGATGCAGCGACAAACAAGTGGACACCGCTAGATGCCGACGCCGATGTCGGCATCG
1201  ---------+---------+---------+---------+---------+---------+   1260
        Y  D  A  A  T  N  K  W  T  P  L  D  A  D  A  D  V  G  I  G

      GGCTGAGGTACGATTGGGGAAAGTTCTACGCATCCAAGACCTTCTATGACCCGGCCAAGA
1261  ---------+---------+---------+---------+---------+---------+   1320
        L  R  Y  D  W  G  K  F  Y  A  S  K  T  F  Y  D  P  A  K  K

      AGAGGCGTGTGCTATGGGGGTGGGTCGGCGAGACTGACTCTGAGCGCGCCGACGTGGCCA
1321  ---------+---------+---------+---------+---------+---------+   1380
        R  R  V  L  W  G  W  V  G  E  T  D  S  E  R  A  D  V  A  K

      AGGGATGGGCTTCCCTACAGTCGATCCCTCGCACGGTrGTGcTAGATACCAAGACGGGCA
1381  ---------+---------+---------+---------+---------+---------+   1440
        G  W  A  S  L  Q  S  I  P  R  T  V  V  L  D  T  K  T  G  S
```

FIGURE 2 CONTINUED

```
     GCAwCCTTATCCAGTGGCCGGTgGTCGAGGTGGAGACGCTCCGTACCAACTCCACCAATC
1441 ---------+---------+---------+---------+---------+---------+ 1500
       X  L  I  Q  W  P  V  V  E  V  E  T  L  R  T  N  S  T  N  L

     TCGGGAGCATCATCGTCGAGCATGGCTCCGTCTTCCCTCTCAGTCTCCACCGGGCCACAC
1501 ---------+---------+---------+---------+---------+---------+ 1560
       G  S  I  I  V  E  H  G  S  V  F  P  L  S  L  H  R  A  T  Q

     AGCTCGACATCGAGGCTTCCTTCCGCCTGGACCCGCTCGATGTCGCCGCCGCAAAGGAGG
1561 ---------+---------+---------+---------+---------+---------+ 1620
       L  D  I  E  A  S  F  R  L  D  P  L  D  V  A  A  A  K  E  A

     CCGACGTTGGCTACAACTGCAGCACCAGCGGTGGCGCGGCCGGTCGTGGAGCGCTCGGTC
1621 ---------+---------+---------+---------+---------+---------+ 1680
       D  V  G  Y  N  C  S  T  S  G  G  A  A  G  R  G  A  L  G  P

     CCTTTGGCCTGCTCGTACTCGCCGATGCCAGGCGCCATGGCGGGGACACGGAGCAGACCG
1681 ---------+---------+---------+---------+---------+---------+ 1740
       F  G  L  L  V  L  A  D  A  R  R  H  G  G  D  T  E  Q  T  A

     CCGTCTACTTCTACGTCGCGAGGGGCCTCGATGGCAACCTGCGCACGCACTTCTGCCATG
1741 ---------+---------+---------+---------+---------+---------+ 1800
       V  Y  F  Y  V  A  R  G  L  D  G  N  L  R  T  H  F  C  H  D

     ACGAGTCACGGTCATCCCGTGCCAACGACATTGTCAAGAGGGTCGTTGGCAACATCGTGC
1801 ---------+---------+---------+---------+---------+---------+ 1860
       E  S  R  S  S  R  A  N  D  I  V  K  R  V  V  G  N  I  V  P

     CAGTGCTCGACGGAGAGGCGCTGTCTGTTAGGGTTCTGGTGGACCAmTCCATTGTCGAGA
1861 ---------+---------+---------+---------+---------+---------+ 1920
       V  L  D  G  E  A  L  S  V  R  V  L  V  D  X  S  I  V  E  S

     GyTTCGCACAGGGTGGGAGGTCGGTGGTGAmTTCaACgGAGTTTaACCCGACTGAGGCCA
1921 ---------+---------+---------+---------+---------+---------+ 1980
       F  A  Q  G  G  R  S  V  V  X  S  T  E  F  N  P  T  E  A  I

     TmTACGCCAATGCCGGGGTATACCTcTTCAACAACGCCACCGGTGCCCGGGTCACCGCCA
1981 ---------+---------+---------+---------+---------+---------+ 2040
       Y  A  N  A  G  V  Y  L  F  N  N  A  T  G  A  R  V  T  A  T

     CCAGTCTyGTCGTCCATGAGATGGACCCCTCCTACAACCAGAACCAGGCCGAGATGGCTT
2041 ---------+---------+---------+---------+---------+---------+ 2100
       S  L  V  V  H  E  M  D  P  S  Y  N  Q  N  Q  A  E  M  A  S

     CATTGTAAATCGAAGATGTACATATTGTTTTTTGTGATAGCATGTTGCACGTACAACATG
2101 ---------+---------+---------+---------+---------+---------+ 2160
       L  *
```

FIGURE 2 CONTINUED

```
     TGTGCTGAACATCGAGGGAGCCTGGATCGAGCCAAGGGGAATGTGCATCCCCGTAGGCAC
2161 ---------+---------+---------+---------+---------+---------+ 2220

     CACCCAAAACAAAACAAAAATACGTGAGCGAGGCGAAACGCAGGCCGGAATAGACTGCCA
2221 ---------+---------+---------+---------+---------+---------+ 2280

     CAATTAGACCGGGAAAAGTGCCCAGAGTGTTTTGATGAATTCAAAAAAAAAAAAAAAAAA
2281 ---------+---------+---------+---------+---------+---------+ 2340
```

```
    GGCACGAGCGGACGAGTGTCGGGTACCATCACGGTGCTCCACAATGGCACGCTCGTCCTC
  1 ---------+---------+---------+---------+---------+---------+  60
    G  T  S  G  R  V  S  G  T  I  T  V  L  H  N  G  T  L  V  L

    CTCTACACGGGGGTCACAGAAGACCCTATGGCCGAGTCCCAGTGCATCGCCGTCCCGACC
 61 ---------+---------+---------+---------+---------+---------+ 120
    L  Y  T  G  V  T  E  D  P  M  A  E  S  Q  C  I  A  V  P  T

    GACCCCAACGACCCCCTCCTTCGCCATTGGACCAAGCACCCCGCCAACCCAGTTCTCGCT
121 ---------+---------+---------+---------+---------+---------+ 180
    D  P  N  D  P  L  L  R  H  W  T  K  H  P  A  N  P  V  L  A

    CACCCACAGGGGGTCCAGGGCATGGACTTCCGAGACCCCACCAGCGCGTGGTGGGACAAG
181 ---------+---------+---------+---------+---------+---------+ 240
    H  P  Q  G  V  Q  G  M  D  F  R  D  P  T  S  A  W  W  D  K

    TCCGACTCCACGTGGCGCATTCTCATCGGTTCCAArGACrAmrACAACGGCAGCCACGCT
241 ---------+---------+---------+---------+---------+---------+ 300
    S  D  S  T  W  R  I  L  I  G  S  K  D  X  X  N  G  S  H  A

    GGCwTCsCCTTCATCTTCAAGACCAAGGACTTCCTTAGCTTCGAGCGTGtTCCmAGkTAT
301 ---------+---------+---------+---------+---------+---------+ 360
    G  X  X  F  I  F  K  T  K  D  F  L  S  F  E  R  V  P  X  Y

    CGtTGCATCGTGtTCsArGGTwCCGGCATGTkGGAGTGCATCGACTTTTACCCCGTTGGA
361 ---------+---------+---------+---------+---------+---------+ 420
    R  C  I  V  F  Z  G  X  G  M  X  E  C  I  D  F  Y  P  V  G

    GGTGGCCACAACTCTTCGTCGGAGGAGTTGTACGTGATAAAGGCGAGCATGGACGACGAA
421 ---------+---------+---------+---------+---------+---------+ 480
    G  G  H  N  S  S  S  E  E  L  Y  V  I  K  A  S  M  D  D  E

    CGACACGACTACTACTCATTGGGGAGGTATGACGCGGCAGCGAACACATGGACGCCATTG
481 ---------+---------+---------+---------+---------+---------+ 540
    R  H  D  Y  Y  S  L  G  R  Y  D  A  A  A  N  T  W  T  P  L

    GACGCCGAGCTAGACTTGGGGATTGGGCTGAGGTACGACTGGGGCAAGCTCTACGCTTCC
541 ---------+---------+---------+---------+---------+---------+ 600
    D  A  E  L  D  L  G  I  G  L  R  Y  D  W  G  K  L  Y  A  S

    ACGTCGTTCTACGATCCACTGAAGCAGCGGCgAATTATGTTgGGGTATGTAGGCGAGGTC
601 ---------+---------+---------+---------+---------+---------+ 660
    T  S  F  Y  D  P  L  K  Q  R  R  I  M  L  G  Y  V  G  E  V

    GACTCTGCGCGAGCcGACGTTGCCAAGGGATGGGCCTCACTTCAGTCGATTCCgAGGACA
661 ---------+---------+---------+---------+---------+---------+ 720
    D  S  A  R  A  D  V  A  K  G  W  A  S  L  Q  S  I  P  R  T
```

FIGURE 8

```
     GTGGCACTAGACGAGAAGACCCGGACGAACcTCcTCCTATGGCCGGTGgAGgAGGTGgAG
 721 ---------+---------+---------+---------+---------+---------+ 780
     V  A  L  D  E  K  T  R  T  N  L  L  L  W  P  V  E  E  V  E

     GCCcTcCGcTaCAACTcCACCGACcTcAGCGGCATCACTGTTgAGAACGGCTCCATCTTC
 781 ---------+---------+---------+---------+---------+---------+ 840
     A  L  R  Y  N  S  T  D  L  S  G  I  T  V  E  N  G  S  I  F

     CACCTCCCTCTCCACCAAGCCAcTCAGCTGGACATCgAGGCTTCCTTCCGCCTCGATGCT
 841 ---------+---------+---------+---------+---------+---------+ 900
     H  L  P  L  H  Q  A  T  Q  L  D  I  E  A  S  F  R  L  D  A

     TCTGATGTTGCTGCCATCAACGAGGCCGACGTCGGCTACAACTGCAGCAGCAGCGGTGGC
 901 ---------+---------+---------+---------+---------+---------+ 960
     S  D  V  A  A  I  N  E  A  D  V  G  Y  N  C  S  S  S  G  G

     GCGGCCGCTCGTGGCGCTCTCGGGCCCTTCGGCCTCCTCGTCCATGCCGCCGGAGACCTC
 961 ---------+---------+---------+---------+---------+---------+ 1020
     A  A  A  R  G  A  L  G  P  F  G  L  L  V  H  A  A  G  D  L

     CGTGGCGAGCAGACGGCGGTGTACTTCTACGTGTCCAGGGCCCTCGACGGTAGCCTcCGG
1021 ---------+---------+---------+---------+---------+---------+ 1080
     R  G  E  Q  T  A  V  Y  F  Y  V  S  R  A  L  D  G  S  L  R

     ACCAGCTTCTGCAACGACGAGACGCGGTCGTCACGGGCCAGGGACGTGACGAAGCGGGTG
1081 ---------+---------+---------+---------+---------+---------+ 1140
     T  S  F  C  N  D  E  T  R  S  S  R  A  R  D  V  T  K  R  V

     GTGGGCAGCACGGTGCCGGTGCTCGACGGCGAGGTGTTAGCGATGAGGGTGCTCGTGGAC
1141 ---------+---------+---------+---------+---------+---------+ 1200
     V  G  S  T  V  P  V  L  D  G  E  V  L  A  M  R  V  L  V  D

     CACTCGATCGTGCAGAGCTTCGCGATGGGTGGGAGGGTCACGGCGACGTCGCGGGTGTAC
1201 ---------+---------+---------+---------+---------+---------+ 1260
     H  S  I  V  Q  S  F  A  M  G  G  R  V  T  A  T  S  R  V  Y

     CCAACGGAGGCTATCTAcgcCAGGGCAGGGGTGTACcTGTTCAACAACgCCACCGGCGCC
1261 ---------+---------+---------+---------+---------+---------+ 1320
     P  T  E  A  I  Y  A  R  A  G  V  Y  L  F  N  N  A  T  G  A

     AGCGTGACGGCGGAGAGGCTCATCGTGCACGAGATGGCCTCGGCGGTATACGACGAGACC
1321 ---------+---------+---------+---------+---------+---------+ 1380
     S  V  T  A  E  R  L  I  V  H  E  M  A  S  A  V  Y  D  E  T

     GTCATGGTTAAGGACTCATAGCTGCTCACACATGAGCTATCAGACCGGTAACGTTGGGTC
1381 ---------+---------+---------+---------+---------+---------+ 1440
     V  M  V  K  D  S  *
```

FIGURE 8 CONTINUED

```
     ACTAGCATTTTCAAGCGTTGAAATAATTTACTTGGCGTAGCAAGCCCCGGGTCCGAGGTT
1441 ---------+---------+---------+---------+---------+---------+ 1500

     CCAAAAGTAAGGTgGGATATTCTTCCAAACTCCGCGAGTCCCGCAAGGTTGTCTAGGTGT
1501 ---------+---------+---------+---------+---------+---------+ 1560

     GAGTGTGATGTCGTTTGCGCACCTGCGCGTGTGCTTGTAATTTGCTGGATTTGTTGTTTC
1561 ---------+---------+---------+---------+---------+---------+ 1620

     TTTACAGAAAAAAAAGGATACTATACTATGTAAGTATCTACATTGTTGTAtmwmwrrwrw
1621 ---------+---------+---------+---------+---------+---------+ 1680

     AwmwwAArAAAAAATATATGCAAGCATGCATGCACGTTGTCGTAAAAAAAAAAAAAAAAA
1681 ---------+---------+---------+---------+---------+---------+ 1740

     AAA
1741 ---  1743
```

FIGURE 8 CONTINUED

```
     GGCACGAGCCGGCTTACTCTGCTCGGCCGACATACACGTACGCAGATCCCAACGGTCCGG
1    ---------+---------+---------+---------+---------+---------+  60
      H  E  P  A  Y  S  A  R  P  T  Y  T  Y  A  D  P  N  G  P  V

     TCTACTATGGCGGATGGTACCACCTCTTCTACCAGCACAACCCCTATGGCGACTCGTGGG
61   ---------+---------+---------+---------+---------+---------+  120
      Y  Y  G  G  W  Y  H  L  F  Y  Q  H  N  P  Y  G  D  S  W  G

     GAAACGTATCTTGGGGACATGCCGTGTCCAAGGACCTGGTGAACTGGCGCCACCTCCCGG
121  ---------+---------+---------+---------+---------+---------+  180
      N  V  S  W  G  H  A  V  S  K  D  L  V  N  W  R  H  L  P  V

     TCGCCTTGGTGCCCGATCAGTGGTACGACATCAACGGCGTCCTGACGGGCTCTATCACAG
181  ---------+---------+---------+---------+---------+---------+  240
      A  L  V  P  D  Q  W  Y  D  I  N  G  V  L  T  G  S  I  T  V

     TGCTCCCAGACGGGCGTGTCATCCTGCTATATACGGGGAACACCGACACCTTTTCGCAGG
241  ---------+---------+---------+---------+---------+---------+  300
      L  P  D  G  R  V  I  L  L  Y  T  G  N  T  D  T  F  S  Q  V

     TCCAGTGCCTCGCAGTGCCCGCCGACCCATCTGACCCGCTcCTTCGTAGCTGGATCAAGC
301  ---------+---------+---------+---------+---------+---------+  360
      Q  C  L  A  V  P  A  D  P  S  D  P  L  L  R  S  W  I  K  H

     ACCCCGcCAACCCCATCCTTTTTCCGCCACCTGGGATCGGGCTCAAGGACTTCCGTGACC
361  ---------+---------+---------+---------+---------+---------+  420
      P  A  N  P  I  L  F  P  P  P  G  I  G  L  K  D  F  R  D  P

     CGCTCACAGCCTGGTTCGAACATTCCGACAACACGTGGnGCACCATCATTGGATCCAAGG
421  ---------+---------+---------+---------+---------+---------+  480
      L  T  A  W  F  E  H  S  D  N  T  W  X  T  I  I  G  S  K  D

     ATGACGACGGCCACGCCGGCATCGkcCTTAGCTACAAGACCACCGACTTTGTGAATTATG
481  ---------+---------+---------+---------+---------+---------+  540
      D  D  G  H  A  G  I  X  L  S  Y  K  T  T  D  F  V  N  Y  E

     AGCTCATGCCAgGGAACATGCATyGTGGCCCCGACGGCACCGGCATGTACGAGTGCCTTG
541  ---------+---------+---------+---------+---------+---------+  600
      L  M  P  G  N  M  H  X  G  P  D  G  T  G  M  Y  E  C  L  D

     ACATCTACCCTGTGGGCGGCAACTCATCCGAGATGTTGGGTGGCGACTCCTCACCTGAGG
601  ---------+---------+---------+---------+---------+---------+  660
      I  Y  P  V  G  G  N  S  S  E  M  L  G  G  D  S  S  P  E  V

     TGTTGnTCGTGCTCAAGGAGAGCGCCAACGACGAGTGGCACGACTACTACGCGCTTGGGT
661  ---------+---------+---------+---------+---------+---------+  720
      L  X  V  L  K  E  S  A  N  D  E  W  H  D  Y  Y  A  L  G  W
```

FIGURE 9

```
     GGTTTGACGCTGCCGCCAACACGTGGACGCCACAGGACCCCGAGGCGGACCTTGGGATCG
721  ---------+---------+---------+---------+---------+---------+  780
      F  D  A  A  A  N  T  W  T  P  Q  D  P  E  A  D  L  G  I  G

     GCCTCAGGTACnACTGGGGCAAGTACTACGCGTnCAAGTTCTTCTACGACCCGATCAAGA
781  ---------+---------+---------+---------+---------+---------+  840
      L  R  Y  X  W  G  K  Y  Y  A  X  K  F  F  Y  D  P  I  K  N

     ACCGGCGTGTCGTTTGGGCTTTCGTCgGCgAGACCGACTCTGArCAGGCCGACAAAGCCA
841  ---------+---------+---------+---------+---------+---------+  900
      R  R  V  V  W  A  F  V  G  E  T  D  S  E  Q  A  D  K  A  K

     AGGGATGGGCGTCCCTyATGTCGATTCCCAGGACsGTGGAGCTTGACAAGAAGACCCGGA
901  ---------+---------+---------+---------+---------+---------+  960
      G  W  A  S  L  M  S  I  P  R  T  V  E  L  D  K  K  T  R  T

     CGAACCTGATCCAATGgcmAGtGgAGGAGATCGAGACCCTTCGCAGGAACGTCACAGACC
961  ---------+---------+---------+---------+---------+---------+  1020
      N  L  I  Q  W  X  V  E  E  I  E  T  L  R  R  N  V  T  D  L

     TCGGTGGCATCACCGTTGAAGCCGGCTCCGTCATTCACCTTCCCCTCCAACAAGGCGGGC
1021 ---------+---------+---------+---------+---------+---------+  1080
      G  G  I  T  V  E  A  G  S  V  I  H  L  P  L  Q  Q  G  G  Q

     AGCTTGACATCGAGGCCTCCTTCCGTCTCAACTCTTCGGACATCGATGCACTCAACGAGG
1081 ---------+---------+---------+---------+---------+---------+  1140
      L  D  I  E  A  S  F  R  L  N  S  S  D  I  D  A  L  N  E  A

     CCGACGTCGGCTTCAACTGCAGTAGCAGCGATGGGGCAGCCGTGCGTGGTGCGCTCGGCC
1141 ---------+---------+---------+---------+---------+---------+  1200
      D  V  G  F  N  C  S  S  S  D  G  A  A  V  R  G  A  L  G  P

     CCTTTGGCCTCCTCGTcTTCGCCGACGGTCGCCACGAACAGACGGCGGCGTACTTCTACG
1201 ---------+---------+---------+---------+---------+---------+  1260
      F  G  L  L  V  F  A  D  G  R  H  E  Q  T  A  A  Y  F  Y  V

     TGTCCAAGGGCCTCGACGGCAGCCTCCTGACGCACTACTGCCACGACGAGTCACGGTCGA
1261 ---------+---------+---------+---------+---------+---------+  1320
      S  K  G  L  D  G  S  L  L  T  H  Y  C  H  D  E  S  R  S  T

     CGCGAGCAAAGGACGTCGTGAGCCGGGTGGTTGGCGGCACTGTGCCAGTGCTTGACGGTG
1321 ---------+---------+---------+---------+---------+---------+  1380
      R  A  K  D  V  V  S  R  V  V  G  G  T  V  P  V  L  D  G  E

     AAACCTTTTCAGTGAGGGTGCTAGTGGACCACTCCATCGTGCAGAGCTTCGTGATGGGTG
1381 ---------+---------+---------+---------+---------+---------+  1440
      T  F  S  V  R  V  L  V  D  H  S  I  V  Q  S  F  V  M  G  G
```

FIGURE 9 CONTINUED

```
     GGAGGACCACGGTGACATCGCGGGCATACCCGACGGAGGCCATCTACGCCGCGGCAGGGG
1441 ---------+---------+---------+---------+---------+---------+ 1500
      R  T  T  V  T  S  R  A  Y  P  T  E  A  I  Y  A  A  A  G  V

     TGTACCTGTTCAACAACGCAACGAGCGCCACCATCACCGCCGAAGGGCTCGTCGTGTACG
1501 ---------+---------+---------+---------+---------+---------+ 1560
      Y  L  F  N  N  A  T  S  A  T  I  T  A  E  G  L  V  V  Y  E

     AGATGGCCTCGGCCGAGAGTCGGGCCTTCTTGGCTGACgACATGTAGATGAAAaCTAGTC
1561 ---------+---------+---------+---------+---------+---------+ 1620
      M  A  S  A  E  S  R  A  F  L  A  D  D  M  *

     AAGAACATGTCAATGGCGATCGTCAAGCTTGCTGGATGGGGATCGTGGTCACAGAGATCT
1621 ---------+---------+---------+---------+---------+---------+ 1680

     TCATTCGCAAGTTCGCGGGTATGTTGTAGCTAGGGTGGTGCCATTGCATGCTGTGGAGGG
1681 ---------+---------+---------+---------+---------+---------+ 1740

     GCTGACGGCTCTCTTTGGACTGGATTGCGATCTGGCCAAGACGGTAGATCGAGAAGCCCT
1741 ---------+---------+---------+---------+---------+---------+ 1800

     cGTCGCCCATGGCTGGGCAAAGCAGTnTGGACCAGAAGGTGTTGGTTCATGTCGTTGCAC
1801 ---------+---------+---------+---------+---------+---------+ 1860

     CTGATGACACGATGGTGCCCAACGAGGCATCCTGACTTCCACATCGTCTCTGCGCATGTC
1861 ---------+---------+---------+---------+---------+---------+ 1920

     ATGCTCCTTACTATCTACCTCTCCCCTTCTGTTAGTTTTGTTGGTCTGTCGTCCTACCTG
1921 ---------+---------+---------+---------+---------+---------+ 1980

     ATGTAGCTCCAATCTTTGTTGCCGGTGCTTTTTTGTCCCAGTTGTTCAACCGnATnTTGC
1981 ---------+---------+---------+---------+---------+---------+ 2040

     CnAnGnACGGTTAnCTAAAnTGnTTCnAACAnGnTTnGAGCnTGnAAnGnTTAAAnTTTT
2041 ---------+---------+---------+---------+---------+---------+ 2100

     TGCTGGAAAAAAAAAAAAAAAAAAAAAAAAAA
2101 ---------+---------+---------+-- 2132
```

FIGURE 9 CONTINUED

*pIp6SFT1*

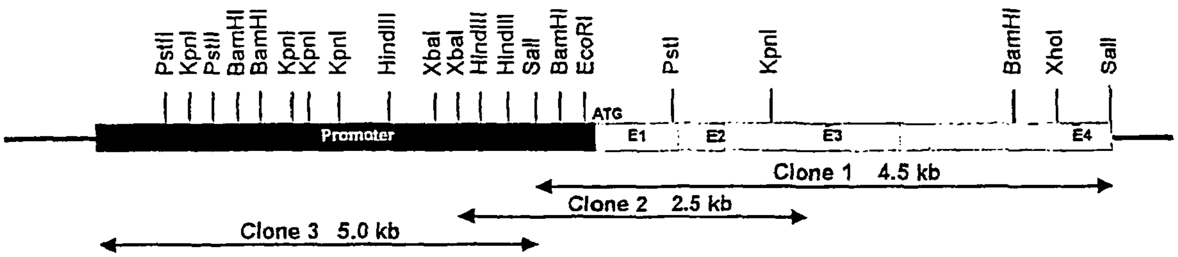

```
      CTCGTGGTTCAAGTTACGAACACCACACAACACACATCCGGATCATGATAAACATTACGG
-5702 --+---------+---------+---------+---------+---------+------- -5643

      CCCAAAAGGTGCCGAGCGGAGCCTGATTATTGGCCTACGCCACCTGGTGAACTTCTTGCT
-5642 --+---------+---------+---------+---------+---------+------- -5583

      GCTGCTGCGGCCGGTTCTGCTGAGCGAAAACCGGTTGCGCATTTGCCCCGGTTAGCGGTG
-5582 --+---------+---------+---------+---------+---------+------- -5523

      GCGGTGGTGGCAACGCCTCGAAAACTTGTTCTCTGTCATCTTTCATCATGCCTCTCTCCA
-5522 --+---------+---------+---------+---------+---------+------- -5463

      TCAACCTCTTGGTCCAGGAGCAATCTTTTTGTTAGGTGGTTTGCCGGTCTCGTTGGATTC
-5462 --+---------+---------+---------+---------+---------+------- -5403

      GGTGTGTGCGAACGGCACGGCTGATCCATAGCGGATTCCATGGTGTACTTGGCCTGGTCC
-5402 --+---------+---------+---------+---------+---------+------- -5343

      TGCCATGGTTTTTTCTCCACCCATTGTTTCTTTTGGCCAGCCCACGGCTGCGTTCCAGTT
-5342 --+---------+---------+---------+---------+---------+------- -5283

      TTCTGCCTTTGGCTTCCACCAGCGCCTGAATTGTCTTGCACTGCAGCCACTTGTTGCATT
-5282 --+---------+---------+---------+---------+---------+------- -5223

      CCATATCTCCTATCCGGGAAATCTTCCGTTGTTTTGTTATGATGGTTGTTCCGGTGCTGA
-5222 --+---------+---------+---------+---------+---------+------- -5163

      TCTGGGCGCGGTGGGAATCTTGGTGCTGGATTCGCTCCGATCGCCGGTTGCATTGGATCT
-5162 --+---------+---------+---------+---------+---------+------- -5103

      CcCAGCGCATAgGTTATCAGCCACCCAGATCATTTCGGTTAAGGTGGTTGGCATGTTTCT
-5102 --+---------+---------+---------+---------+---------+------- -5043
```

FIGURE 10

```
      TTGTAACTTTGCCAmAACGGTGAGCCTCTCCGGCATCCATTGcTGAACCAAGCAATTTCC
-5042 --+---------+---------+---------+---------+---------+------- -4983

      TGTGCTTCAATCACACCCTCGCAAGAGTTTCTTGTGGAGTTCCACCGGGTCAGATAGCCC
-4982 --+---------+---------+---------+---------+---------+------- -4923

      CGGTCTGTTTTATTCTCGCGCTGTTGGCACATGGCGAGCTGCTGCGGTCTGTTTGGCCTC
-4922 --+---------+---------+---------+---------+---------+------- -4863

      CGGTATGTACTGCTGAAGTTGCTCACGAATGCTTCTTCAAAATCAAGCCAGCCGTTTATG
-4862 --+---------+---------+---------+---------+---------+------- -4803

      CTTCCCTTTGGCAAATTGTTGAGCCAAATGCGAGTCGGTCCTACCAGCACTGACGGTATG
-4802 --+---------+---------+---------+---------+---------+------- -4743

      TATCTTACCACCCAGCGCCGGTTTCCTTCGCCAGCTGCGGTTCCTCCACCTCCAGCGACA
-4742 --+---------+---------+---------+---------+---------+------- -4683

      TATACCGTTGTGACGTAGTCTGCCAGCCAATCTTCCGGCTTTGTGGTGCCATCGTACGTT
-4682 --+---------+---------+---------+---------+---------+------- -4623

      TTTGTGTCACGGGGCAACTGAAAGTTGCGTACCGGTTGCTCTTCCCTCATGATCCGCGGG
-4622 --+---------+---------+---------+---------+---------+------- -4563

      TCAAAACATTGTGGAACCGGCGGACCCTCAGCCTCGATCATCTCaArAGAAATATACtTT
-4562 --+---------+---------+---------+---------+---------+------- -4503

      TGTCCaAGCcTATGTCGTGCATCTCTATCCgGGCaAAGCATCTTTCTCCCAAACgTTCTC
-4502 --+---------+---------+---------+---------+---------+------- -4443

      CGAGAGGGTTTCGGtrATTTCCGGTTCGCTCCCATCCGTAATCGGCTTCATCATACCGGT
-4442 --+---------+---------+---------+---------+---------+------- -4383

      TCGGTGCGACCGTGACACCCCTTGGGTACCTCAGCACTTCTGCCTCTTGTGCAGCGTGTC
-4382 --+---------+---------+---------+---------+---------+------- -4323

      CCGCCCTTGCTGGGCGATAGTTTTGCCCGGTTTCACCGTTTCCGGCACCAGCATTTCCGG
-4322 --+---------+---------+---------+---------+---------+------- -4263

      CATAACCGTTTCCGGCAGTGCCTGCCCCTTGGCTTTTTCTACCGGGATCGTGTTGCCCGG
-4262 --+---------+---------+---------+---------+---------+------- -4203

      CTCTCTGTTTTCCGGCCAAAACCGGATCATAAACAGTCATCCGTTGTGCATTTGCATCTT
-4202 --+---------+---------+---------+---------+---------+------- -4143

      TTTCTCTTCTTTTGCTCGGATGGGGGGACGAAGCATGCCCATGCGACTTGCTTCCGGCAT
-4142 --+---------+---------+---------+---------+---------+------- -4083

      TTCTTGCCGAACGCACCAATTGCGATGCAGCAGCTGCCTTGGTGTTTCGGGCCATCTCTG
-4082 --+---------+---------+---------+---------+---------+------- -4023
```

FIGURE 10 CONTINUED

```
      TATTTTGTGCCTCAATCATATCTAGCAGTTCTCCCCTAGCTTGATGTTTTGCTAAGGCAT
-4022 --+---------+---------+---------+---------+---------+-------  -3963

      CTCCTGAAAAGGAATCACATGCTTATACAGCAGCCCTAGTAGCTTTCAAAGTTTTATCCG
-3962 --+---------+---------+---------+---------+---------+-------  -3903

      GACTGCTATACTTAGGTTTCTCTACCATGATCAAAGATACCGACACGCTCTTACCGGAAA
-3902 --+---------+---------+---------+---------+---------+-------  -3843

      GAACCTCCCGGCGTAGATCCTGATCTAGGTTACGACCTCTAAGCCGGTTTCCAGCTACTC
-3842 --+---------+---------+---------+---------+---------+-------  -3783

      TAGCAGGGTTTGCGCTAACAGAAGCAAAACCATGAGCAGCGTTATACTCACGTAGGGTCA
-3782 --+---------+---------+---------+---------+---------+-------  -3723

      GGTTGAGCTCCTGCTGAGCCTTGACGATGTTTCCTGCACTGGAGAGCAGCTTCTGTCGTT
-3722 --+---------+---------+---------+---------+---------+-------  -3663

      GTGCCTCCAGTTCGGCTTGGGTGGCTGCAGCGTCGGTGTTGTGCGCGATGGGCGTGGCCA
-3662 --+---------+---------+---------+---------+---------+-------  -3603

      ACAAGCTCATGGCCGCTTGCAGTGGGGTTGCTTCCGGTGGCGCGGTAGAAGCACCGGCGA
-3602 --+---------+---------+---------+---------+---------+-------  -3543

      CGATCTCATCGCGCTCGGTCGGAGGCTTGGCCGTGCACGTGGACTTGGTTTGCCCAGGGC
-3542 --+---------+---------+---------+---------+---------+-------  -3483

      CCTCCCCTGCACTTTCTTTACCGGCGCCTCCAGCGCCAGCCATCATCACCTCCACGCTGT
-3482 --+---------+---------+---------+---------+---------+-------  -3423

      CGGCGGCGCGGTCGTAGCGCGGCCCGCGAGAAGCTGAAGACCTTGGCGGATCCGGCGCCA
-3422 --+---------+---------+---------+---------+---------+-------  -3363

      CCAGCACCAGCGATGGGTACTGGCGCTCTGGCACGGTGCCGAAGTAGATGCGGTGGGAGC
-3362 --+---------+---------+---------+---------+---------+-------  -3303

      CGGACTCGAAGATGCGGCCGTTCTTGGGGAAGCGGCCACCGTTGGTGAAGCAGCCTGCGT
-3302 --+---------+---------+---------+---------+---------+-------  -3243

      TGTTGTTgACGAAATCCAGCGAGCCGrAGACGGTGAGGAGGCCTGCCTGGATATGAACTC
-3242 --+---------+---------+---------+---------+---------+-------  -3183

      CAGCAAGCGCAGCTGCTGGCCCCATGGTGGGCGCCAACTGTCGTCGTGGTGTAACAACAG
-3182 --+---------+---------+---------+---------+---------+-------  -3123

      ATGCCATAGGATGGCTTAAGTTGGGGCCGAATGTGCGCTAGAGGATCCGGGGGAGGGTTT
-3122 --+---------+---------+---------+---------+---------+-------  -3063

      GGTTAACAGGGAAAGAGAGAAAAGAAGCTGGTATGTATTGATGAACTTGGCCGATGGCCA
-3062 --+---------+---------+---------+---------+---------+-------  -3003
```

FIGURE 10 CONTINUED

```
      GAGGTTGAAGACAGTACGGTACAGGACCTTAGCAACTTGCTACTAAACTGCCTAATTTCT
-3002 --+---------+---------+---------+---------+---------+-------  -2943

      CTATTGAATCGATCTCTTCGTGCTAGGGTGTACCCCCTCTCCTTATATAGGGGAGAGGGT
-2942 --+---------+---------+---------+---------+---------+-------  -2883

      GGCTTACAAGGGAAGAAACCCTAATGGAATCTTTGATGAGCTAAGCTACTTTATAAAGCT
-2882 --+---------+---------+---------+---------+---------+-------  -2823

      ACTCTGGCCCAGCTGACACCGGCTCTATCTTTAATCAGGGACTGATGACCTCGGCCGGTA
-2822 --+---------+---------+---------+---------+---------+-------  -2763

      TCTTTTACGTCACCTTCTGCTTTGGTGCCAGGGCTTCGATTAAAGCTGAAGTGCTTCGCT
-2762 --+---------+---------+---------+---------+---------+-------  -2703

      CATCTTTGTCCTTTAGTCCTTGGTGGAATCTTTGGCTGAAGTGCCGACAGGCTACAGTGA
-2702 --+---------+---------+---------+---------+---------+-------  -2643

      TCCAATACCGGTTTGCCGGTACCTTTACCTCTGAGTTCCGGTACCTTGGTCCTTGGTGAT
-2642 --+---------+---------+---------+---------+---------+-------  -2583

      ATGGCCTCCTTATTGCCAGGACTCCGGTATACCCCTCCTGGGATACCGGTTCGTACTAGC
-2582 --+---------+---------+---------+---------+---------+-------  -2523

      TTCGCCTAGCTAAGATTAACTTTAGAGTCCGGATCACTCTTTGATCCGGTTTATAACTAC
-2522 --+---------+---------+---------+---------+---------+-------  -2463

      CATATTATGGCTTATTTGCCATAGTCTTGGCCTACCGGGGGCCATCCCCCCGACAGCCCC
-2462 --+---------+---------+---------+---------+---------+-------  -2403

      TTACGCCGCCTGATGTTATCATTGGACGGCAGGCGTTTCCTGGCCAACTGCCATAGGAAG
-2402 --+---------+---------+---------+---------+---------+-------  -2343

      CACCTTCCCTGGGACCATGATCTGCCACAAGTCACTGAAGTGCTTGGAAGGGGTGCCCTG
-2342 --+---------+---------+---------+---------+---------+-------  -2283

      GCAGAGCTTAAGGTACAAAGACCGCACTAAGAATCTCCCCGAAGATTCTAGCGCCCAAGT
-2282 --+---------+---------+---------+---------+---------+-------  -2223

      AACCTTATCTTGCAAACCTGAGGTGGGTGGTACCGTGAACTCCCGCGTGAGGTTAGACAA
-2222 --+---------+---------+---------+---------+---------+-------  -2163

      ATCAACACGATCCCCAAAGCCCAGCCCGCGCCGAAACGGTAGATGTCAGGCCCCCCCACA
-2162 --+---------+---------+---------+---------+---------+-------  -2103

      ACGAGAGGAGTCgGGTCGAGGCCTCCTGCTCAGTCACAATGGCAAAGAGCGAGGGGAACC
-2102 --+---------+---------+---------+---------+---------+-------  -2043

      TATCGmACAGGGGTCCCGACCCCTGCCACTAGTCCTGnTAGAAGCTCGCCGTCTTACCAT
-2042 --+---------+---------+---------+---------+---------+-------  -1983
```

FIGURE 10 CONTINUED

```
      TATGCACTGTGTGTCTCGCCCCCAAGCGAAAAAGGTGTTTGAGTTTCTGGATAGAGTTCC
-1982 --+---------+---------+---------+---------+---------+------- -1923

      AGAACTGCGAGCCCGGTCGGTGTGCATCTAACATCAGGTCCTTATCCCTGAGGTACTTGT
-1922 --+---------+---------+---------+---------+---------+------- -1863

      TCCGTAGGATCTCCGCCCAGAGGCCTTGCTCCCCAGCATAAAGCCTCCAGATCCACTTAA
-1862 --+---------+---------+---------+---------+---------+------- -1803

      CCACAAGACACGCGTTCATGAGCCTGGTGTCCACAATTCCAAGCCCCCAAGCTCTTTGGC
-1802 --+---------+---------+---------+---------+---------+------- -1743

      CTACAGATCGCCGACCACCTCACCCAGTGGTATTTCCGCTTGGTACTGCTGGCTTCCCAA
-1742 --+---------+---------+---------+---------+---------+------- -1683

      TAGAAGCGTGATCGGTGTCTATCCATAATGATGTGCGGCCCCTCCCCCAGAAGGAAAACC
-1682 --+---------+---------+---------+---------+---------+------- -1623

      GTCATCGCCATGGCATGAAGCGGTAGGCTAGATAAGCAAGTGTTAGTGAGGGTCAGCCtA
-1622 --+---------+---------+---------+---------+---------+------- -1563

      cgCCGCAGAGGACATAAGCTTCCCCATCCACGGCTCGGCGCGCTTACCTACCTTGGCCAT
-1562 --+---------+---------+---------+---------+---------+------- -1503

      AAGAGGACCCCAGTCCGCGaGCAGTGAGAGCGCGATCACTGATCGGTAGCCsCATGTATG
-1502 --+---------+---------+---------+---------+---------+------- -1443

      AGAATGGAAAGGACCCAAGTTTGCAGTTGAGCATATGCGCGATCCTGGGCCCATCTTCCT
-1442 --+---------+---------+---------+---------+---------+------- -1383

      GATCCATACCTAACACCATAACCTCACTTTTGTGGAAATTGATCCTTAGCCCCGACATGC
-1382 --+---------+---------+---------+---------+---------+------- -1323

      TCTCAAAACAGAGCAGAATGTACTTCAAATTGGCCACGGCCAAATCATCAGGCTGGATCA
-1322 --+---------+---------+---------+---------+---------+------- -1263

      TAATAATGGTGTCGTCAGCATATTACAAGTGAGATACCCCCAGGTATCAAGTGTGGGATT
-1262 --+---------+---------+---------+---------+---------+------- -1203

      ACCCCCGCAGTATGACCGGCCCCTCTAGCTTTCTCTAGAATAGCAGCTAGGGCTTCGACA
-1202 --+---------+---------+---------+---------+---------+------- -1143

      ACGTAGTCGAAGAGAATAGGGGATAGGGGGTCACCCTGGCGCACCCCGCGCCAATTGCGA
-1142 --+---------+---------+---------+---------+---------+------- -1083

      AAGTATTTCCCAATGTCTCCATTAATGGAGATTGCAGTCTGGCCTACCnAGACCAGACTG
-1082 --+---------+---------+---------+---------+---------+------- -1023

      aGGsCCCTGTGCACmTaAAGTTGGCTCAAAAcCCCTTGCATATAAGAmCCTCACGGAGGA
-1022 --+---------+---------+---------+---------+---------+------- -963
```

FIGURE 10 CONTINUED

```
      AGGGcCCAGTTCACCCgGATCATAGGCTTTCTAGAAGTCTAATTTTAGGAATACTCCCCT
-962  --+---------+---------+---------+---------+---------+-------  -903

      AAGCTTCCTGGACTTGGATTCATGGATGATTTCTTgGGAGGGCCAGAACGcCCCTCGTGA
-902  --+---------+---------+---------+---------+---------+-------  -843

      ATGTGTCTCCCTTTGATAAAGGCGGATTGGGAACGACTAATGGTCATGTGCGCAATAGGG
-842  --+---------+---------+---------+---------+---------+-------  -783

      GATAGCCTAGTGGCATAAGCTTTGGCAACAAACTTAAAAATCACATTAATCAGCGCAATC
-782  --+---------+---------+---------+---------+---------+-------  -723

      GGCCTAATGTGTCACATTCCCCATCTCCTATGGTTTTCTCGCGCCACATATTTTATATGC
-722  --+---------+---------+---------+---------+---------+-------  -663

      CGGAACGGTGGCCAACCGGCTAACTGGAATTGGCCAACAATGGTGACsCATGTwAAGAGA
-662  --+---------+---------+---------+---------+---------+-------  -603

      CTaCTAGGTCATGGTCAAGACgATCATGTACgTAGAGGGGCAAAAAATTGCATGTGAGGT
-602  --+---------+---------+---------+---------+---------+-------  -543

      TAAACCGGGTCGGAGAAGAAGCGGCAGCGGCGGCGCGCCGTCGACacggtCTsGAGGTTG
-542  --+---------+---------+---------+---------+---------+-------  -483

      AAGATGAAGGGCATCTCAAGATTTCCATTGTAATTTTTATTTTCGTTCGGGAGTGTTTCT
-482  --+---------+---------+---------+---------+---------+-------  -423

      TTTAATGCTAAGGTTTTATTCGCAAAAAAAAAAGAAATGGGTTGGGGAAGAAGGGAAAAG
-422  --+---------+---------+---------+---------+---------+-------  -363

      GAATGGAGTAACAAGGCATATACAAAAAAAGATTATGTACACACGGTCACAGGAATAGGG
-362  --+---------+---------+---------+---------+---------+-------  -303

      AAGGGAAGGATAGAGAATAAAAAGTGCCTAGAAATGGATAGCAACTATATATCCAAAAAG
-302  --+---------+---------+---------+---------+---------+-------  -243

      AAAAGAAATCAACCGGGCGAGCGATAAGAGAGGATCCACCGATCTCGTAGGGTCAATGTC
-242  --+---------+---------+---------+---------+---------+-------  -183

      CATTTCACCCTCGCTGACCGCCCGGnCCCACACTCCAGCCACCCTCACCGGCCTACGCAC
-182  --+---------+---------+---------+---------+---------+-------  -123

      GCGCTTGCATCCCGCGCCCTGTTTCCATTTnGGGnnCCCGCGCAGCTATAAATCCCGCTC
-122  --+---------+---------+---------+---------+---------+-------  -63

      GTTGGCTCGCTCGGGAAGCCACATCCATCAGAATCTGCTCCATTTGTTTTGGAATTCGCC
-62   --+---------+---------+---------+---------+---------+-------  -3

      CATGGAGTCTCGGTCCATTCCCGGCGCGTACGCGTACGAGCCGCTGCCCCACTCCTACGA
-2    --+---------+---------+---------+---------+---------+-------  57
        M  E  S  R  S  I  P  G  A  Y  A  Y  E  P  L  P  H  S  Y  D
```

FIGURE 10 CONTINUED

```
     CGACGCCCATGGCCACGACGACCGCCGGAGCACCGGCGGCGTGAGGTGGCGCGCGTGCGC
 58  --+---------+---------+---------+---------+---------+-------  117
      D  A  H  G  H  D  D  R  R  S  T  G  G  V  R  W  R  A  C  A

     GGCCGTTCTTGCGGCGTCGGCCCTGGTCGTCTTCGTGGTCGCCAGCACGCTCGCCGGGTC
118  --+---------+---------+---------+---------+---------+-------  177
      A  V  L  A  A  S  A  L  V  V  F  V  V  A  S  T  L  A  G  S

     GAGGGTGGACCGCGTGGyCGTCGACGTGGCCGCCATGCCGGCGCTGTCGGAGACGGCGAG
178  --+---------+---------+---------+---------+---------+-------  237
      R  V  D  R  V  X  V  D  V  A  A  M  P  A  L  S  E  T  A  R

     GAGCCGCGGGAGGGACGCGGGCGTGTCGGAGAAGACGTCCGGCGCGGCGGACGAGATGGG
238  --+---------+---------+---------+---------+---------+-------  297
      S  R  G  R  D  A  G  V  S  E  K  T  S  G  A  A  D  E  M  G

     GTTCCTCGGCGCCGGCGCCGGCGCCGACGCCGnCGGGTTCCCGTGGAGCAACGCCATGCT
298  --+---------+---------+---------+---------+---------+-------  357
      F  L  G  A  G  A  G  A  D  A  X  G  F  P  W  S  N  A  M  L

     GCAGTGGCAGCGCACGGGTTTCCATTTCCAGCCCGAGATGAACTGGATGAACGGTACGTG
358  --+---------+---------+---------+---------+---------+-------  417
      Q  W  Q  R  T  G  F  H  F  Q  P  E  M  N  W  M  N

     CCACGATCCATATCCATTACTCCTTTCCTTTTCCCGTCCGATTCAGGCTCAGATGTATAT
418  --+---------+---------+---------+---------+---------+-------  477

     ATCTTGCTTTCATATCTATCTATACATCTCTCGCGCGTGGnTGwTTTGATCGACATATAT
478  --+---------+---------+---------+---------+---------+-------  537

     AAGCTGACGCTGTTGCCATTGCTTTCTTTCCTGTTTGCTCGmTGCTGCGGCCGkCGGCGT
538  --+---------+---------+---------+---------+---------+-------  597

     ACCTTCTyCGGCGACGACATGCATGCAGATCCCAACGGTTAGTACCGATTAACCGATCTC
598  --+---------+---------+---------+---------+---------+-------  657
                                 D  P  N

     TATCCCATGGAATATTCTTGTTCAATTGTCCGCTTGCCCsrTCnCCGCCTGTCTCGCGCG
658  --+---------+---------+---------+---------+---------+-------  717

     CGCGCGCGGAAGGGAAACCATATCTGCATCTATTTTGACCACGCGCCATTGGTTGCCGCA
718  --+---------+---------+---------+---------+---------+-------  777

     AAACTGAAACCGGTGTAGATGnATATAGAGAGATCCAGATTACCTCGnTCCCnnTnTCTC
778  --+---------+---------+---------+---------+---------+-------  837

     ATTGGTACACACGATTAATCACGTCCCCACTGCAATAATGTGCCAGCCGTAACCACAAAT
838  --+---------+---------+---------+---------+---------+-------  897

     GATTATTATCCTTTATTTnGCCATAAnCTTAnGCATACATAAATCCnCCTAATCACCTAT
898  --+---------+---------+---------+---------+---------+-------  957
```

FIGURE 10 CONTINUED

```
      CCACACCTTCCTTAnCTGACTCTAGTTTTAGTATAnATTTGCATCTCTTATAACTAATCC
 958  --+---------+---------+---------+---------+---------+-------  1017

      TTGTTTTCATCTATnTACGGCCTGGATTnATCTAATCTTrAATTrTCyrTGcAGGTCCGG
1018  --+---------+---------+---------+---------+---------+-------  1077
                                                          G  P  V

      TkTATTACCGmGGATGGTACCACCTcTTCTaCCAGTACAACCCygAGGGGrCGGTGTGGg
1078  --+---------+---------+---------+---------+---------+-------  1137
        Y  Y  R  G  W  Y  H  L  F  Y  Q  Y  N  P  E  G  X  V  W  G

      GCAACATCGCGTGGgGCCACGCyGTsTCyCGGGACCTrGTCCACTGGCGCCACCTCCCGC
1138  --+---------+---------+---------+---------+---------+-------  1197
        N  I  A  W  G  H  A  V  S  R  D  L  V  H  W  R  H  L  P  L

      TCGCmATGGTGCCyGACCAATGGTAcgACATCAAmGGTGTCTGGACrGGCTCCGCCACyG
1198  --+---------+---------+---------+---------+---------+-------  1257
        A  M  V  P  D  Q  W  Y  D  I  X  G  V  W  T  G  S  A  T  V

      TGTTCCCyGAyGGGACmCTCAACATGCTCTACACGGGGTCCACCAACGCCTCCGTGCAGG
1258  --+---------+---------+---------+---------+---------+-------  1317
        F  P  D  G  T  L  N  M  L  Y  T  G  S  T  N  A  S  V  Q  V

      TyCAGTGCCTCGCCGTgCCCGAGGACCCCAwsGACTCCyTCCTCCGCAacTGGACCAAGC
1318  --+---------+---------+---------+---------+---------+-------  1377
        Q  C  L  A  V  P  E  D  P  X  D  S  X  L  R  N  W  T  K  H

      ACgAAGCCAAycCCGTGCTCCTCCCGCCrCCCGGGATCGGwGACAAGraCTTCCGtGaCC
1378  --+---------+---------+---------+---------+---------+-------  1437
        E  A  N  P  V  L  L  P  P  P  G  I  G  D  K  X  F  R  D  P

      CgACCaCCGCmTGGTTcGAyGAGTCCGACCAGACGTGGCGCACCGTCATCGGGTCCAAGG
1438  --+---------+---------+---------+---------+---------+-------  1497
        T  T  A  W  F  D  E  S  D  Q  T  W  R  T  V  I  G  S  K  D

      ACAACAACGrCCAyGCCGGyATsrCCATGGTGTACAAGaCCmargACTTCCTcAACTAsG
1498  --+---------+---------+---------+---------+---------+-------  1557
        N  N  X  H  A  G  X  X  M  V  Y  K  T  X  D  F  L  N  X  E

      AGCTCATCysAggAtACTTGCATCGtGTCGATGGCACTGGCATGTGGGAGTGCATCGACT
1558  --+---------+---------+---------+---------+---------+-------  1617
        L  I  X  G  Y  L  H  R  V  D  G  T  G  M  W  E  C  I  D  F

      TCTACCCCGTTGGAGGCAAGAACGGCAGCGAGGAGTTGTACGTGATCAAGGAGAgCAgCG
1618  --+---------+---------+---------+---------+---------+-------  1677
        Y  P  V  G  G  K  N  G  S  E  E  L  Y  V  I  K  E  S  S  D

      ACGACGACCGACATGACTGGTACACGCTAGGGAAATACGACGCGGCAGCCAACACGTTca
1678  --+---------+---------+---------+---------+---------+-------  1737
        D  D  R  H  D  W  Y  T  L  G  K  Y  D  A  A  A  N  T  F  T

      CGGCCGCGGACCCGGAGAACGACCTAGGGATTGGGCTGAGGTACGACTGGGGCAAGTTTT
1738  --+---------+---------+---------+---------+---------+-------  1797
        A  A  D  P  E  N  D  L  G  I  G  L  R  Y  D  W  G  K  F  Y
```

FIGURE 10 CONTINUED

```
     ACGCGTCCAAGACCTTnTACGATCCGGCCAAgAACCGGCGAGTGCTCTGGGGATGGATCG
1798 --+---------+---------+---------+---------+---------+------- 1857
      A  S  K  T  X  Y  D  P  A  K  N  R  R  V  L  W  G  W  I  G

     GCGAGACCGACTCTGAGCGCGCCGATGTCGCCAAgGGATGGGCATCCCTCATGGTATGCT
1858 --+---------+---------+---------+---------+---------+------- 1917
      E  T  D  S  E  R  A  D  V  A  K  G  W  A  S  L  M

     CGCTTTTCCCTTACTGCTTCTCATCTTTGTTTCGTTATGCATATGTTAGTTCCATCTCAT
1918 --+---------+---------+---------+---------+---------+------- 1977

     ACATCCTGCAATTGATCAGACCTTCAACCTGCTTAATCGAAATGTTGATGCAAGCATGCA
1978 --+---------+---------+---------+---------+---------+------- 2037

     TATAgATGCTGACGGATCGGCCCGCCGACACATACGTTGGCAGAGAACTGTTAATCGCAT
2038 --+---------+---------+---------+---------+---------+------- 2097

     TGTCAATGGGATGAGAATGGATTTATGTCTGCTAATTGGTCGTGGGGATTGGCGACGTTG
2098 --+---------+---------+---------+---------+---------+------- 2157

     TCACGCATCGATTAATTGATACACAAGTCGCAGTCATGCCGTTTAACGtTTTCtTTTCCT
2158 --+---------+---------+---------+---------+---------+------- 2217

     GTTTAACCACCTACCTACCTATAGGTCGCATGTCGCCAGCTATATCGCTGTTGAGAAGAT
2218 --+---------+---------+---------+---------+---------+------- 2277

     TGAAATCCAAGAGCAAGTACAATAAGATCTAGTCAGCTGGCTACAAGGATTAAAATAATA
2278 --+---------+---------+---------+---------+---------+------- 2337

     TATTTGTGTCTAGTTGGAGGAGAGATAGGAGGAGAGAGAATGTGAGTATGCTCTTATGCA
2338 --+---------+---------+---------+---------+---------+------- 2397

     AGAGCTAGCTCTAGCACGTGCTCCTAGGCAAGGTGTGTGAATGAAAGGTGGGTCATCCAT
2398 --+---------+---------+---------+---------+---------+------- 2457

     TGAAAAAATAGTACATTCTAATAGCCAACTATTGTACTTGTTGGCTACATGTTGACTATA
2458 --+---------+---------+---------+---------+---------+------- 2517

     GATGACATGGCATCTTGCTTATAGCCCAACAACCGGCTATACTATTGGAGTTGCTCTTAA
2518 --+---------+---------+---------+---------+---------+------- 2577

     GATGACAACTGGGATTTAAAACGTGCATGCATGTTCCGTGAGATCTTTAGTTAATCCCAA
2578 --+---------+---------+---------+---------+---------+------- 2637

     CTCATGCACCTAATTAAGATGTACCAGTTGACCTGACTGTGCAAACGTACGTACCCATAC
2638 --+---------+---------+---------+---------+---------+------- 2697

     CCTTCTCGAAGCTATTAGTATAATGCATGTAACCCTTTTTGGTGATCCTCTCCTGTGGTA
2698 --+---------+---------+---------+---------+---------+------- 2757

     GGTTCTATACTAGTATTCAATTGAAAGGCTAGCTGAATTTCAAGAGTACTTTTTCTCTGA
2758 --+---------+---------+---------+---------+---------+------- 2817
```

FIGURE 10 CONTINUED

```
     CCAGTTCCATATTCTCCGTTGCATCTTCCAAACTTTGGTCAACGGGTGCAAGCCAAGTGT
2818 --+---------+---------+---------+---------+---------+-------  2877

     CATTTCTCAACAACATGTTATAGCAAAGACTATATCCAACCCAACTGGCATGCATGTGCC
2878 --+---------+---------+---------+---------+---------+-------  2937

     CTAGCTAGACACCACATGTGCACGCCACGTCGATCCCACGTGGAACCACGTGGATGCCTA
2938 --+---------+---------+---------+---------+---------+-------  2997

     AATAAATGTATCGATGGCTTCTGATGCTGACCGTTATGATTGGCAACGGTATCTTAATTT
2998 --+---------+---------+---------+---------+---------+-------  3057

     ATCTGCTCCCAGCTAACCACCAAATTTCAACTTTCTCCTACCTTCCTGTCTGGAATAGAC
3058 --+---------+---------+---------+---------+---------+-------  3117

     AGGATCTGCATGGTAATATTATGTATTTGATTAGTCGTGCCAAACATGGATCCGACTAAT
3118 --+---------+---------+---------+---------+---------+-------  3177

     CGTTCTTATCGAGTTTGAACATTCTTTACTCTTGTGCATATGTGACACCAATTTGTTCTG
3178 --+---------+---------+---------+---------+---------+-------  3237

     CTCTTGTATTTTTCTTTTCCAAGATGTTGATGTGCATAATGCGTGATCGATCATTGGACC
3238 --+---------+---------+---------+---------+---------+-------  3297

     TACCTCTGCTTGAATTATTTTAACTAAGAAAATGATTGATTGATGTGTGCTTGCAGTCGA
3298 --+---------+---------+---------+---------+---------+-------  3357
                                                            S  I

     TTCCGAGGACGGTGGAACTCGACGAGAAGACCCGGnCCAACCTCATCCAATGGCCGGTGG
3358 --+---------+---------+---------+---------+---------+-------  3417
       P  R  T  V  E  L  D  E  K  T  R  X  N  L  I  Q  W  P  V  X

     AnGAGCTCGAGACCCTCCGCATCAAGTCCACCGACCTCGGTGGCGTCACCATCGACCACG
3418 --+---------+---------+---------+---------+---------+-------  3477
       E  L  E  T  L  R  I  K  S  T  D  L  G  G  V  T  I  D  H  G

     GCAGCGTCTACCCACTCCCTCTCCACCGCGCCACACAACTCGACATTGAGGCCTCCTTCC
3478 --+---------+---------+---------+---------+---------+-------  3537
       S  V  Y  P  L  P  L  H  R  A  T  Q  L  D  I  E  A  S  F  R

     GCATCGACACTGCCACCGTCnCTGCCCTCAATGAGGCTGACGTTGGCTACAATTGCAGCA
3538 --+---------+---------+---------+---------+---------+-------  3597
       I  D  T  A  T  V  X  A  L  N  E  A  D  V  G  Y  N  C  S  T

     CCAGCGGTGGCTCTGCCAACCGTGGCGCACTCGGCCCCTTTGGCCTCCTCGTCCTCGCCG
3598 --+---------+---------+---------+---------+---------+-------  3657
       S  G  G  S  A  N  R  G  A  L  G  P  F  G  L  L  V  L  A  D

     ACGGTAAGGCAGAGCAGACGGCAGTGTACTTCTATGTGGCCAAGGGCCTCGACGGGACCC
3658 --+---------+---------+---------+---------+---------+-------  3717
       G  K  A  E  Q  T  A  V  Y  F  Y  V  A  K  G  L  D  G  T  L
```

FIGURE 10 CONTINUED

```
      TCCAAACCCACTTCTGCCACGACGAGTCACGGTCGACGGTATCGATAAGCCnTGATATCG
3718  --+---------+---------+---------+---------+---------+-------   3777
        Q  T  H  F  C  H  D  E  S  R  S  T

      AATTCCTGCAGCCCGGGGGATCCACTAGTTCTAGAGCGGCCGCCACCGCGGTGGAGCTC
3778  --+---------+---------+---------+---------+---------+------ 3836
```

FIGURE 10 CONTINUED pIp6SFT3

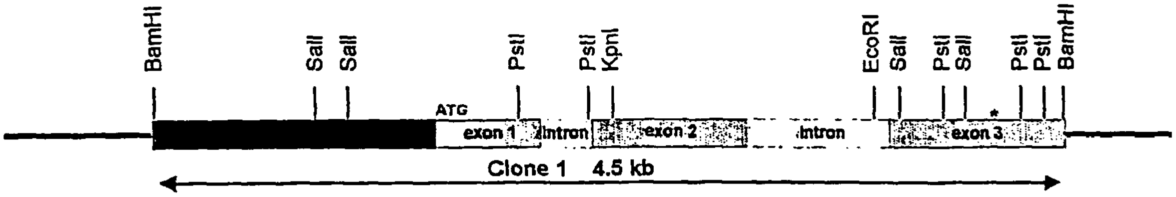

```
      GGATCCAGATGTGTAGCAGCATTATTGTCCTACAGTACTTAATTAACTCTTATGTGGACC
-1619 ---------+---------+---------+---------+---------+---------+ -1560

      TTTCCAGTTTGATATTTCCGGCTCATGTGGAGTATCAGCGGTCGTGATAGGAGATCCCAA
-1559 ---------+---------+---------+---------+---------+---------+ -1500

      AAGCAACCAATGGCCAAATCTCTTGGGCCCCAAATTCTGGCCATTAGTGTACTAAACTAG
-1499 ---------+---------+---------+---------+---------+---------+ -1440

      GCACCTTGTGGTATAGAGTCCAAATGATGGAGAACCGTCCTTTATAAAAAAAAACCCCAC
-1439 ---------+---------+---------+---------+---------+---------+ -1380

      ATGTCCTGCGTCATTCCCAATAATTGTGCCACGGCAGCATGAACTTCGCATGTGCGTAAC
-1379 ---------+---------+---------+---------+---------+---------+ -1320

      AAAGATCAGCGGACAACGGCAATATCGCAAGCTCCATGCCTCACGCGATTGCTCCGTTTT
-1319 ---------+---------+---------+---------+---------+---------+ -1260

      GTAGAGTAAcGAGTGTTAAAATTGATTGATGGTGCTTTATTCACGCGATGTAACAATGTT
-1259 ---------+---------+---------+---------+---------+---------+ -1200

      GGTAAATTCATATTTTTTGGGTAAAAAAAAAAAGTGCTTCAATAGCATGAAACACATGTA
-1199 ---------+---------+---------+---------+---------+---------+ -1140

      TGCTCTTTCTATGAGCTATATATATATACCCTGTGGTAAGCCCTCCGTTGGATTGTTTCAAA
-1139 ---------+---------+---------+---------+---------+---------+ -1080

      CTAAAACAAAAAACTTGCTGTAGCAGTTCAGTAAGAAAACTGAATTTCTGAACCAGTTTT
-1079 ---------+---------+---------+---------+---------+---------+ -1020

      CAGTTTTCTGAATCTGTTCCATATAGTGTTATCCACGTCGAGTTTTGGGCTTTTATATAT
-1019 ---------+---------+---------+---------+---------+---------+ -960

      ACATCTACAAATGTGTGCTACAATTACATGTGTACTTTTTGAATAGGTCGATTGTGAATG
 -959 ---------+---------+---------+---------+---------+---------+ -900
```

FIGURE 11

```
      CTTTGGCAAGCACCTCTAAAAAATTAGATTAGAAGGCAACCCCGTTACAGTACACCCTCA
-899  ---------+---------+---------+---------+---------+---------+  -840

      TTGTTGGTCGTCGACCTATTATCTCCCTACGGCCTCTTGTACCGTCTATAGAACGGTCmC
-839  ---------+---------+---------+---------+---------+---------+  -780

      ATTTGACATCTACAAATTcaCCTTTGTAATcaGACACTATATCATTCTTAAAGATTCAAT
-779  ---------+---------+---------+---------+---------+---------+  -720

      GGTAAcGCTCAAGGGCAATCAATTTCAACCGCAACGAACTCGGACGGTTTGCTGATGATG
-719  ---------+---------+---------+---------+---------+---------+  -660

      ACCTCTTCTCCGGCCTCTAGGATTCTCCCCGACCATAAGTTGATGCTTTCAAACAACCAG
-659  ---------+---------+---------+---------+---------+---------+  -600

      CTGGGTCGACAACACCCATTGCTAGAGAGACACTaTATGTTTTGTTTcCCAGCTAATTTA
-599  ---------+---------+---------+---------+---------+---------+  -540

      CTGCACGGCAACTATCTGTACTGGATTTCCTGtgGGTATATATAGTAGTATTTCTTCAAT
-539  ---------+---------+---------+---------+---------+---------+  -480

      TAATGGCATTTGAAAAATAAATATGTTTGGTGAGGCTTGAAGCACATATAGGATGGAGAA
-479  ---------+---------+---------+---------+---------+---------+  -420

      GAGAGTGTGTCCACAAATATAGATCTACTGCTACCTCGCCCACCCTAGTAAGTAAGTAGA
-419  ---------+---------+---------+---------+---------+---------+  -360

      GTGATGGAATCAGCTGAGCGAGCCCGTCCAGAGCTGGGATATGCGATCTCACATGGCCAA
-359  ---------+---------+---------+---------+---------+---------+  -300

      TGTCGGCCTTCTCCGTCGCTGACCCGTGGGCCCCACGAGCCAGACGTGTCCGTGCTGGCG
-299  ---------+---------+---------+---------+---------+---------+  -240

      CACCCTGCCATTTTAATCTTTAGCGCGATCAACGGACGGGAGCGCTCGACGGAGACGCGT
-239  ---------+---------+---------+---------+---------+---------+  -180

      ACGTACGTACGTACAGGCTGTTCAAAACTAGTCTATTTGACGCAACGGGCCAAAACCCCT
-179  ---------+---------+---------+---------+---------+---------+  -120

      GCGAAAACCCCTGCTATAAATCGCGCCCGCTCGCTCCTCCGTCCATCCATCCATCCACCG
-119  ---------+---------+---------+---------+---------+---------+  -60

      CCCAGATCAGCCTTCCTCGGAACCATCGACCGGGCCGCCGCCGACGCGACGCGACGCCAT
-59   ---------+---------+---------+---------+---------+---------+  0
                                                                M
```

FIGURE 11 CONTINUED

```
     GGAGTCCCCAAGCGCCGTCGTCCCCGGCACCACGGCGCCGCTGCTTCCTTATGCGTACGC
  1  ---------+---------+---------+---------+---------+---------+  60
      E  S  P  S  A  V  V  P  G  T  T  A  P  L  L  P  Y  A  Y  A

     GCCGCTGCCGTCGTCCGCCGACGACGCCCGTCAAAACCGGAGTGGCGGGAGGTGGCGCGC
 61  ---------+---------+---------+---------+---------+---------+  120
      P  L  P  S  S  A  D  D  A  R  Q  N  R  S  G  G  R  W  R  A

     GTGCGCCGCCGTGCTGGCCGCATCGGCGTTGGCGGTGGTCGTCGTGGTCGGGCTCCTCGC
121  ---------+---------+---------+---------+---------+---------+  180
      C  A  A  V  L  A  A  S  A  L  A  V  V  V  V  V  G  L  L  A

     GGGCGGCAGGGTGGATCGGGTCCCGGCCGGCGGAGACGTGGCGTCGGCCACGGTGCCGGC
181  ---------+---------+---------+---------+---------+---------+  240
      G  G  R  V  D  R  V  P  A  G  G  D  V  A  S  A  T  V  P  A

     CGTGCCGATGGAGTTCCCGAGG     GGGCAAGGACTTCGGnGTGTCGGAGAAGTCCTC
241  ---------+---------+---------+---------+---------+---------+  300
      V  P  M  E  F  P  R  S  R  G  K  D  F  G  V  S  E  K  S  S

     CGGTGCCTACTCCACCGACGGCGGGTTCCCGTGGAGCAACGCCATGCTGCAGTGGCAGCG
301  ---------+---------+---------+---------+---------+---------+  360
      G  A  Y  S  T  D  G  G  F  P  W  S  N  A  M  L  Q  W  Q  R

     CACCGGGTTCCATTTCCAGCCGGAGCAGCACTACATGAACGGTACgGsGCATGCAGTTGT
361  ---------+---------+---------+---------+---------+---------+  420
      T  G  F  H  F  Q  P  E  Q  H  Y  M  N

     TGCTATCTAGTAGTGTTTcAGATTCAGATTTCGtTTTTCCCCTTGATCTGACGTACGTAC
421  ---------+---------+---------+---------+---------+---------+  480

     GTGGGTCTGATTCTGATcaTGGATCGTTCGAGGAAACCAGCTAATCGATTTcCTGTTTGT
481  ---------+---------+---------+---------+---------+---------+  540

     CTGTTGCCGGCGGCGTATTCTGCAGATCCCAACGGCCCCgTGTaCTACGGCGGATGGTAC
541  ---------+---------+---------+---------+---------+---------+  600
                                D  P  N  G  P  V  Y  Y  G  G  W  Y

     CACCTCTTCTACCAGCACAACCCCAAGGGCGACAGCTGGGGCAACATCGCGTGGGCCCAC
601  ---------+---------+---------+---------+---------+---------+  660
     H  L  F  Y  Q  H  N  P  K  G  D  S  W  G  N  I  A  W  A  H

     GCCGTCTCCAAGGACATGGTCAACTGGCGCCACCTCCCTCTCGCCATGGTTCCCGACCAG
661  ---------+---------+---------+---------+---------+---------+  720
     A  V  S  K  D  M  V  N  W  R  H  L  P  L  A  M  V  P  D  Q

     TGGTACGACAGCAACGGCGTCCTCACCGGCTCCATCACCGTGCTCCCCGACGGCCAGGTC
721  ---------+---------+---------+---------+---------+---------+  780
     W  Y  D  S  N  G  V  L  T  G  S  I  T  V  L  P  D  G  Q  V

     ATCCTGCTCTACACCGGCAACACCGACACCCTAGCCCAGGTCCAGTGCCTCGCCACGCCC
781  ---------+---------+---------+---------+---------+---------+  840
     I  L  L  Y  T  G  N  T  D  T  L  A  Q  V  Q  C  L  A  T  P
```

FIGURE 11 CONTINUED

```
     GCCGACCCGTCCGACCCGCTCCTCCGCGAGTGGGTCAAGCACCCCGCCAACCCCATCCTC
841  ---------+---------+---------+---------+---------+---------+  900
     A  D  P  S  D  P  L  L  R  E  W  V  K  H  P  A  N  P  I  L

     TACCCTCCCCCCGGCATCGGCCTCAAGGACTTCCGCGACCCCCTCACCGCCTGGTTCGAC
901  ---------+---------+---------+---------+---------+---------+  960
     Y  P  P  P  G  I  G  L  K  D  F  R  D  P  L  T  A  W  F  D

     CACTCCGACCACACCTGGCGCACCGTCATCGGCTCCAAGGACGACGACGGCCACGCCGGC
961  ---------+---------+---------+---------+---------+---------+  1020
     H  S  D  H  T  W  R  T  V  I  G  S  K  D  D  D  G  H  A  G

     ATCATCCTCAGCTACAAGACCAAGGACTTCGTCAACTACGAGCTCATGCCGGGGAACATG
1021 ---------+---------+---------+---------+---------+---------+  1080
     I  I  L  S  Y  K  T  K  D  F  V  N  Y  E  L  M  P  G  N  M

     CACCGCGGGCCCGACGGCACCGGAATGTACGAGTGCATCGACCTCTACCCCGTCGGCGGC
1081 ---------+---------+---------+---------+---------+---------+  1140
     H  R  G  P  D  G  T  G  M  Y  E  C  I  D  L  Y  P  V  G  G

     AACTCGTCCGAGATGCTCGGCGGCGACGACTCGCCCGGCGTGCTCTTCGTGCTCAAGGAG
1141 ---------+---------+---------+---------+---------+---------+  1200
     N  S  S  E  M  L  G  G  D  D  S  P  G  V  L  F  V  L  K  E

     AGCAGCGACGACGAGCGCCACGACTACTACGCGCTCGGAAGGTTCGACGCCGTCGCCAAC
1201 ---------+---------+---------+---------+---------+---------+  1260
     S  S  D  D  E  R  H  D  Y  Y  A  L  G  R  F  D  A  V  A  N

     GTTTGGACGCCCATCGACCGGGAGCTGGACCTTGGGATCGGGCTCAGATACGACTGGGGA
1261 ---------+---------+---------+---------+---------+---------+  1320
     V  W  T  P  I  D  R  E  L  D  L  G  I  G  L  R  Y  D  W  G

     AAGTACTACGCCTCCAAGTCCTTCTACGACCAGAAGAAGAACCGCCGCATCGTATGGGCA
1321 ---------+---------+---------+---------+---------+---------+  1380
     K  Y  Y  A  S  K  S  F  Y  D  Q  K  K  N  R  R  I  V  W  A

     TACATCGGCGAGACCGACTCCGAGCAGGCCGACATCACCAAGGGATGGGCCAATCTCATG
1381 ---------+---------+---------+---------+---------+---------+  1440
     Y  I  G  E  T  D  S  E  Q  A  D  I  T  K  G  W  A  N  L  M

     GTATGCACTTGTACAAATCCACATCATTCTTCTTGTACTTAGTATTAGTACCTTATTTGC
1441 ---------+---------+---------+---------+---------+---------+  1500

     ATATATTCTGTCATTATCATCCTCAtkGyTyCATCGCCGGCATAAGCATGGAGGACGACT
1501 ---------+---------+---------+---------+---------+---------+  1560

     AGCTAACACTATTAGACGGACGTCTTGTCGCTTGTTTCTTTCTTGTTTAACGGTCACCTC
1561 ---------+---------+---------+---------+---------+---------+  1620

     TCGGTTCTACTGTAGGCAGGTCACTATCGTAATTAGCTGCTAGCTGCCTTGTTGACACAC
1621 ---------+---------+---------+---------+---------+---------+  1680
```

FIGURE 11 CONTINUED

```
     ATGGTGTGCCCGTCCCCTTTGGCTCTGCCTGCCTGCATGCATGTCGCATTCAGTCCCTAG
1681 ---------+---------+---------+---------+---------+---------+ 1740

     TTAAAATCGCAGATCTACCATCGACTACTCATATGCCTAGTGTAGTAGTGTGTCCTTTCC
1741 ---------+---------+---------+---------+---------+---------+ 1800

     CCCAGTATAGAATTTGCTTGTATTTTTGTTAATCGCCATGGTAGGTGCTTGATGCTGAAC
1801 ---------+---------+---------+---------+---------+---------+ 1860

     TAATCTTTTATTTACTTACCGATCGGGACATAGGCCGGCTGAATTTCAACGGCTTGTTTT
1861 ---------+---------+---------+---------+---------+---------+ 1920

     CTTTTGGTCACTTTCATCATTGATCTCACACTGCACCTCTCAAGTGTCCATTTTCAGTCT
1921 ---------+---------+---------+---------+---------+---------+ 1980

     AGTGGAAAATTAGCTAGCATTGCTCCACAATCGTACTCATCAACtTGTTGCTTATTAAAT
1981 ---------+---------+---------+---------+---------+---------+ 2040

     TGTTTATGTGAAGACTACGATATCTTCTTTGTTCGTGCCGTTGTTTCTTTAAGAGAATTC
2041 ---------+---------+---------+---------+---------+---------+ 2100

     GGTGGAGGGCGCAGGCCCTTTATATTGATTACATAGACAAGAGTAGTTGTTtGCAGTCAA
2101 ---------+---------+---------+---------+---------+---------+ 2160

     GTTAAATAATTGATTCATTATAACGGTAAATGTATCATCGTGTGTGCAGACGATTCCAAG
2161 ---------+---------+---------+---------+---------+---------+ 2220
                                                      T  I  P  R

     AACGGTGGAGCTTGACAGGAAGACCCGCACAAACCTCATCCAATGGCCAGTGGAGGAGGT
2221 ---------+---------+---------+---------+---------+---------+ 2280
      T  V  E  L  D  R  K  T  R  T  N  L  I  Q  W  P  V  E  E  V

     CGACACCCTCCGCAGGAACTCCACGGACCTCGGTCGCATCACCGTCAACGCCGGCTCCGT
2281 ---------+---------+---------+---------+---------+---------+ 2340
      D  T  L  R  R  N  S  T  D  L  G  R  I  T  V  N  A  G  S  V

     CATTCGCCTCCCCCTCCACCAGGGCGCTCAACTCGACATCGAGGCCTCCTTCCAACTCAA
2341 ---------+---------+---------+---------+---------+---------+ 2400
      I  R  L  P  L  H  Q  G  A  Q  L  D  I  E  A  S  F  Q  L  N

     CTCTTCCnACGTGGATGCTATCAACGAGGCCGACGTCGGCTACAACTGCAGCACCAGTGG
2401 ---------+---------+---------+---------+---------+---------+ 2460
      S  S  X  V  D  A  I  N  E  A  D  V  G  Y  N  C  S  T  S  G

     TGCCGCCGTACGGGGGGCGCTCGGCCCCTTTGGCCTCCTCGTCCTTGCCAACGGCCGCAC
2461 ---------+---------+---------+---------+---------+---------+ 2520
      A  A  V  R  G  A  L  G  P  F  G  L  L  V  L  A  N  G  R  T

     CGAACAGACGGCTGTGTACTTCTACGTGTCCAAGGGCGTCGACGGTGCCCTCCAGACCCA
2521 ---------+---------+---------+---------+---------+---------+ 2580
      E  Q  T  A  V  Y  F  Y  V  S  K  G  V  D  G  A  L  Q  T  H
```

FIGURE 11 CONTINUED

```
     CtTTTGCCACGACGAGTCACGGTCAACGCGGGCAAAGGATGTCGTGAATAGrATGATTGG
2581 ---------+---------+---------+---------+---------+---------+ 2640
      F  C  H  D  E  S  R  S  T  R  A  K  D  V  V  N  R  M  I  G

     CAGCATCGTGCCGGTGCTTGACGGT AGACCTTTTCGGTGAGGGTGCTAGTGGACCACTC
2641 ---------+---------+---------+---------+---------+---------+ 2700
      S  I  V  P  V  L  D  G  X  T  F  S  V  R  V  L  V  D  H  S

     CATCGTGCAGAGCTTCGCGATGGGCGGGAGGATCACGGCGACGTCGCGGGCGTACCCGAC
2701 ---------+---------+---------+---------+---------+---------+ 2760
      I  V  Q  S  F  A  M  G  G  R  I  T  A  T  S  R  A  Y  P  T

     GGAGGCCATCTACGCGGCCGCGGGGGTCTACCTCTTCAACAACGCCACGGGCGCCACCGT
2761 ---------+---------+---------+---------+---------+---------+ 2820
      E  A  I  Y  A  A  A  G  V  Y  L  F  N  N  A  T  G  A  T  V

     CACCGCCnAGAGGCTCGTCGTGCACnAnATGGCCTCAGCTGACAACCATATCTTCACGAA
2821 ---------+---------+---------+---------+---------+---------+ 2880
      T  A  X  R  L  V  V  H  X  M  A  S  A  D  N  H  I  F  T  N

     CGACGACTTGTAGATGAAACCAAGTTTAGCTCGTGTTGCATTCTTGTTAACGGCCGGTGA
2881 ---------+---------+---------+---------+---------+---------+ 2940
      D  D  L  *

     TTGCCTATCTACACATTCATTTGGCGTTCGATTGGTGGGTTCCTTGATCTTGTCATGGAT
2941 ---------+---------+---------+---------+---------+---------+ 3000

     GGGGATCGTACAATAGTTTTTGATTTGGTTTTTTTTTTTGTATCGGGGTGATGTATGAAA
3001 ---------+---------+---------+---------+---------+---------+ 3060

     TTAnATGACTGTCCTACCCCCAAGTCGTAACTATCTGCAGGAGCCCTTCTGCAGTGACTA
3061 ---------+---------+---------+---------+---------+---------+ 3120

     TGATGACAGTGTCATCTATCAACTGTATCAGATTACTTAATTTCCAAAGGGGGTTTCCTT
3121 ---------+---------+---------+---------+---------+---------+ 3180

     TTAATCGAGTCATGGGATCC
3181 ---------+---------+ 3200
```

FIGURE 11 CONTINUED

```
       GGATCCGGAGCTGACGGCGGGGTGGAAGGGAGAGAAGCGATCGATACTTTCACCGCGTTG
-966   ------+---------+---------+---------+---------+---------+---   -907

       CTAGGTTTTCGCCTCCACCATGCGAAACAAGCGATGTGCAGGATCAAAATGTAAAATCGA
-906   ------+---------+---------+---------+---------+---------+---   -847

       TCGGACGATGGAGAGGTGGAGGTGAAGCAAGGCCAGTGTCCTGCCCGTGCGTGCCAGGAG
-846   ------+---------+---------+---------+---------+---------+---   -787

       TCTATCATGGATAGAATGAGAGGGCGCCCCGGGTGTCGCTCTTGCTTGTTCTAATTTAGC
-786   ------+---------+---------+---------+---------+---------+---   -727

       CACTTGTTCACCTTTTGTTTTTCTCATTGCATGGTTGGAATTCATGATTAATTTCACTAT
-726   ------+---------+---------+---------+---------+---------+---   -667

       CAGTTACAGTTTTGGTTATCTAATAATTTTATGAAACCCCATATCTATAGACGGCTTCAT
-666   ------+---------+---------+---------+---------+---------+---   -607

       CAAGGTTGTGGTGTGCGTTATCAAGGTTCCATTACTTTTCCCCAAAAAAAAAGGTTCCAT
-606   ------+---------+---------+---------+---------+---------+---   -547

       TGCGTTGTTATATTCATGTTTTGGACCGGGTCGTAATTCAATACTCGAATGACCATTAGT
-546   ------+---------+---------+---------+---------+---------+---   -487

       CCATCGATTACCAGATTTCATGAAAGGAGTTAAATGAAGCAGTATACATACATGCATGTA
-486   ------+---------+---------+---------+---------+---------+---   -427

       TTTTACTATATATACAGTTGTATTTTACTATATATACTATGTAATAGGGACTTTATGCGC
-426   ------+---------+---------+---------+---------+---------+---   -367

       ACGTGTCCTTCTTGATGGTTAATTCACACCGCAATCAAATTTACTGAGATGGCAGCTTGT
-366   ------+---------+---------+---------+---------+---------+---   -307

       AGTACCCTGACTGACATTACATGAATGCGATGGCCGGCCAGTCCTCTACCTTCTTGTTTT
-306   ------+---------+---------+---------+---------+---------+---   -247

       TGACACTTGGcCCGGTCCCCArCATTGTACGATGTGTTCGTGTCgGACAATCACAATGCA
-246   ------+---------+---------+---------+---------+---------+---   -187

       TGCATGTCTCTTygGGGACATCCGATACGATACAGGTAcCAGaAGAATGCATGTCTAGTC
-186   ------+---------+---------+---------+---------+---------+---   -127

       TTGACGGTTCACACTkrCATCCGATATGTTCGTTTGTGGACGTAATATTTCTGAAATATC
-126   ------+---------+---------+---------+---------+---------+---   -67
```

FIGURE 14

```
     TTTTTTCAGTATATTATTTATGAAATTTGGTTAAATAAATTCCGGGATTTACACCGAATT
-66  ---------+---------+---------+---------+---------+---------+   -7

     AATGCATGGTTGCTGACAGTCAAGCATGCATATATCCCGTCTTGATGGTTCACACTGAGG
-6   ---------+---------+---------+---------+---------+---------+   53
         M  V  A  D  S  Q  A  C  I  Y  P  V  L  M  V  H  T  E  A

     CCGGTCCCACAAACCAGCCAAGGCATCGCCCAACTATAAATCACGCTCGCTCCTCAAGAG
54   ---------+---------+---------+---------+---------+---------+   113
      G  P  T  N  Q  P  R  H  R  P  T  I  N  H  A  R  S  S  R  V

     TGAGATCGTCCATCCATCAACTTTCCTCTATTTTTTCGAACACGATGAAGTCACGCGCCA
114  ---------+---------+---------+---------+---------+---------+   173
      R  S  S  I  H  Q  L  S  S  I  F  S  N  T  M  K  S  R  A  T

     CCCCGCCTCGTCTGATCCAGTGCGTGTCGCTGCACCTCCACCGTACTAGCGGCGGCGCGA
174  ---------+---------+---------+---------+---------+---------+   233
      P  P  R  L  I  Q  C  V  S  L  H  L  H  R  T  S  G  G  A  T

     CGAGGTGGCGCGCGTGCACAACCACCGTGCTGGCCGTGGGCGTGCTCGCCCACGCGCTCG
234  ---------+---------+---------+---------+---------+---------+   293
      R  W  R  A  C  T  T  T  V  L  A  V  G  V  L  A  H  A  L  A

     CAGGGGCCGGCGAAATAATGGCGTGGTGGCTCGGCGCCGGGAAGGGCGCGGATGGGTTCC
294  ---------+---------+---------+---------+---------+---------+   353
      G  A  G  E  I  M  A  W  W  L  G  A  G  K  G  A  D  G  F  P

     CGTGGACCAGCGCGATGCTGCAGTGGCAGCGCACCGGGTTCCATTTCCAGCCCGAGAAGA
354  ---------+---------+---------+---------+---------+---------+   413
      W  T  S  A  M  L  Q  W  Q  R  T  G  F  H  F  Q  P  E  K  N

     ATTTTATGAGCGGTAGTACAGGAGTAGTTGATTATTTATTTTTCTCTGGCAATCTGTACG
414  ---------+---------+---------+---------+---------+---------+   473
      F  M  S

     TGCAGAAACTGACTGACTGACTGGCTTTCTTGTTTGTTTGCTCGTGGCAGATCCCAGCGG
474  ---------+---------+---------+---------+---------+---------+   533
                                                    D  P  S

     TTAGTACGTACATCACTTTCTTTGTTTTTGTTGAACTGGGAAGTTTATATTGATTAGTAA
534  ---------+---------+---------+---------+---------+---------+   593

     CAACATCTTACAGAGTATTAATTAAGGGGAGTGCTGGGCGTCCCCCGGCGGATTAGAAAT
594  ---------+---------+---------+---------+---------+---------+   653

     CTAATCCCACGGGTCCCCAACCATCCGATCAACAGATCTGGAACGTTTTCGGCCGTCAGA
654  ---------+---------+---------+---------+---------+---------+   713
```

FIGURE 14 CONTINUED

```
714   TCAAACCAACCAGCCCTCTCTTCCACTTTTACTACCATGATGAACCAAAGTAGCAAAAAA   773
      ------+---------+---------+---------+---------+---------+---

774   CGGTTCAATTGTAGCAAAATCTATTTTCACCTAAAAACACAGACCTCGCCGGAGATGTCG   833
      ------+---------+---------+---------+---------+---------+---

834   CCGGAGACCTCGCCGGAGAACTTGTAGCAAAAAACATATACTATTATAGCTAAAACCTAG   893
      ------+---------+---------+---------+---------+---------+---

894   AACAAATGTAGCAAAACCTGATTCCGCCGGATACTCGCAGGAGACATAGTAGCAAAGAAA   953
      ------+---------+---------+---------+---------+---------+---

954   ATATGGTATAGTAGCAAGAAAACAAAAATATTGTAGCAAATTTTTTTTGCTATTGTAGCA   1013
      ------+---------+---------+---------+---------+---------+---

1014  AACTATGCATTGATGAAAAATATAATTGTAGTAAGACAAATTTCGCCAAAAAGAATTGTA   1073
      ------+---------+---------+---------+---------+---------+---

1074  GCAAACAATGTATACTATATTAACATAAATGCCAAACTAAAGTAGCAAAAACAATATATT   1133
      ------+---------+---------+---------+---------+---------+---

1134  ATTGTAGCATCACGCCCCGAAGCAAAAACGCCCAGGAGCCGTTGGCAGCAGGCGGCCGTT   1193
      ------+---------+---------+---------+---------+---------+---

1194  GACTTGCAGCTAGAGGGTAGGGGGGAGAGGAGGATGACsGCCATGGCTGGGCGTGCTTGC   1253
      ------+---------+---------+---------+---------+---------+---

1254  AGTGGGAGGAATAGGCGGAGGAAGTAGGAGGCGGCTGCCGCCGCGCGTAGGGGAGGCGGC   1313
      ------+---------+---------+---------+---------+---------+---

1314  ACGCGGAGCTCGCTATGAGGGCTGACGACGGAGTCGGCGGAGGAGGTCAGGGGAGGGCGG   1373
      ------+---------+---------+---------+---------+---------+---

1374  CGGCCGCCGTTCGCAGAGGGTGCTCGAGGCAGCTCGCGGACCTTGGCGTGGCGGCGGGCG   1433
      ------+---------+---------+---------+---------+---------+---

1434  GCGGCTGCTGCAGTGGGGTTGGCGGCAGTGGCGCCGCACAGCAGAATCGCGTGTAGGTGG   1493
      ------+---------+---------+---------+---------+---------+---

1494  TCGCGGGACGCCGCCGGTCGCCCGGGGATGCAGGGTGGAGGCGCGGGACGCCGCCGTAGT   1553
      ------+---------+---------+---------+---------+---------+---

1554  TCGGGATGCAGGGGAGGAGGCGGAGTGGCACGCTATGGAGGAAGTTGCGGCGGCACGCCG   1613
      ------+---------+---------+---------+---------+---------+---
```

FIGURE 14 CONTINUED

```
     GGTCAGCGGCAcCCGGCACGTGGCTTGCGCGGCGGGCTGGCTCGACGCGTTGCTGGGTTG
1614 ------+---------+---------+---------+---------+---------+---  1673

     GCGGTGGCTCGTGGCAGGGCGACgACGGCGGCGCGACAGCCTACCTGTGCGGTTGCTCGA
1674 ------+---------+---------+---------+---------+---------+---  1733

     TTTGGGGATGAGATTGAAACCAGAAAAAAAGGGATGAAGGGGAAGACGATAACGTGGGTG
1734 ------+---------+---------+---------+---------+---------+---  1793

     GGTCCCACGGGACACGTGGCATACGGGGGAATCGGAGGAATGGAGCGCTGATCCCCCGGG
1794 ------+---------+---------+---------+---------+---------+---  1853

     GGTTCGGCAGCGTTTCCCATTAATTAATTGACTTGATGATGCAGGTCCGGTGTACTACCG
1854 ------+---------+---------+---------+---------+---------+---  1913
                                                  G  P  V  Y  Y  R

     TGGATGGTACCACCTATTCTACCAATACAACCCGGAGGGCACCGTGGGGGCCAACATCAC
1914 ------+---------+---------+---------+---------+---------+---  1973
      G  W  Y  H  L  F  Y  Q  Y  N  P  E  G  T  V  G  A  N  I  T

     GTGGGGCCACGCCGTGTCCCGGGATCTCGTCCACTGGCGCCACCTCCCTCTCGCCATGCT
1974 ------+---------+---------+---------+---------+---------+---  2033
      W  G  H  A  V  S  R  D  L  V  H  W  R  H  L  P  L  A  M  L

     CCCTGACCGGTGGTACGACATCAACGGCGTTTGGACCGGCTCCGCCACCATGCTCCCCAA
2034 ------+---------+---------+---------+---------+---------+---  2093
      P  D  R  W  Y  D  I  N  G  V  W  T  G  S  A  T  M  L  P  N

     CGGGACGCTCACAATGCTCTACACGGGGTCCACCAATGCCTCTACCCAGGTCCAGTGCCT
2094 ------+---------+---------+---------+---------+---------+---  2153
      G  T  L  T  M  L  Y  T  G  S  T  N  A  S  T  Q  V  Q  C  L

     CGCCGTCCCCGCAAACCCCAACGACTCCCTCCTCCGCAACTGGACAAAGCACCCTGCCAA
2154 ------+---------+---------+---------+---------+---------+---  2213
      A  V  P  A  N  P  N  D  S  L  L  R  N  W  T  K  H  P  A  N

     CCCCGTCCTCCTCCCGCCCCCCGGCATCGGCGATAAGGACTTCCGTGACCCCACCACCGC
2214 ------+---------+---------+---------+---------+---------+---  2273
      P  V  L  L  P  P  P  G  I  G  D  K  D  F  R  D  P  T  T  A

     CTGGTTCCACAAGTCAGACTCCACCTGGCACATCGCCATCGGGTCCAAGGATGACCACGG
2274 ------+---------+---------+---------+---------+---------+---  2333
      W  F  H  K  S  D  S  T  W  H  I  A  I  G  S  K  D  D  H  G

     CCACTCCGGCATCGCCATCACGTACAAGACCAAAGACTTTGTTAGCTACGAGCTCATCCC
2334 ------+---------+---------+---------+---------+---------+---  2393
      H  S  G  I  A  I  T  Y  K  T  K  D  F  V  S  Y  E  L  I  P
```

FIGURE 14 CONTINUED

```
      GGGATTCTTGCATCGTGTCGAGAGCACTGGCATGTGGGAGTGCGTTGACTTCTACCCCGT
2394  ------+---------+---------+---------+---------+---------+---  2453
       G  F  L  H  R  V  E  S  T  G  M  W  E  C  V  D  F  Y  P  V

      CGGCAGCCGCGACCAAGACGCCGAGAACTCGTCGGAGGAGCTGTTGTACGTGATGAAGGC
2454  ------+---------+---------+---------+---------+---------+---  2513
       G  S  R  D  Q  D  A  E  N  S  S  E  E  L  L  Y  V  M  K  A

      GAGCATGGACGACCACCGGCACGACTGCTACGCATTGGGGAGGTACGACGCTGAGGCAAA
2514  ------+---------+---------+---------+---------+---------+---  2573
       S  M  D  D  H  R  H  D  C  Y  A  L  G  R  Y  D  A  E  A  N

      CATATGGACGCCGGTGGACCCTGAGGCGGACGTGGGGATCGGGCTGAGGTACGACTGGGG
2574  ------+---------+---------+---------+---------+---------+---  2633
       I  W  T  P  V  D  P  E  A  D  V  G  I  G  L  R  Y  D  W  G

      AAGGTTTTTTGCGTCCAAAACGTTCTATGATCCGGCGAAGCGGCGGCGCGTGCTGTTGGG
2634  ------+---------+---------+---------+---------+---------+---  2693
       R  F  F  A  S  K  T  F  Y  D  P  A  K  R  R  R  V  L  L  G

      GTATGTCGCCGAGGCCGACTCCGAGTTGGCCGACGTGGCCAAGGGATGGGCTTGCCTCCA
2694  ------+---------+---------+---------+---------+---------+---  2753
       Y  V  A  E  A  D  S  E  L  A  D  V  A  K  G  W  A  C  L

      GGTATCTCTATACTATACATCGCTATGATTGTGTTTTACCTTGCATTTTGCATCAATAGC
2754  ------+---------+---------+---------+---------+---------+---  2813

      TCCATCCTTCATTTCGTTACTCATGTTAGATTGATACATCAGTGCATCGCCTCTTGGGGA
2814  ------+---------+---------+---------+---------+---------+---  2873

      TTGAAATGCTATCTGTTGTTATATCAGTGCATGCATGCATCATACAATCCATCTTCTCTT
2874  ------+---------+---------+---------+---------+---------+---  2933

      TTGTGCAATACAACCTGCTTAAAATGTTGATTAATGCATGGCTGATGGCTTTCTGGGAAA
2934  ------+---------+---------+---------+---------+---------+---  2993

      ACTTGTTAATCACATTGTTAATATATTCTAATGCGAGAAGAGAGGAACTTGTGGCTGCTA
2994  ------+---------+---------+---------+---------+---------+---  3053

      ATTAGTCGTGGATGGTGTCGCAGTCATGGACGAGTACTAGTTGCACTCGCTCCGTATGGT
3054  ------+---------+---------+---------+---------+---------+---  3113

      CCGCTGGTATTTTTTTTTTTTTAAAATTGACCATCAATTTGATCAACAAAATATGAGTTAT
3114  ------+---------+---------+---------+---------+---------+---  3173
```

FIGURE 14 CONTINUED

```
      ATTTTACAAAAATTATACCGTTAGAAACTCTTTTTAAATATGAATCCAATGTTATATTTT
3174  ------+---------+---------+---------+---------+---------+---  3233

      TTTACAGTATTACTCATATATGGTTGACAAAATTTGTGGTCAGAGTTTTTCTTAAAATAC
3234  ------+---------+---------+---------+---------+---------+---  3293

      GTGCATGCTTTATAAACCCATACGGAGGTAGTACATCGCTACATCGCAGTCTCATCGTTT
3294  ------+---------+---------+---------+---------+---------+---  3353

      CAGGTTTCTATCTTTTTTCTTTTGGGAAAATTCTTTCTTGTTTAACGGCCAATAATAGCT
3354  ------+---------+---------+---------+---------+---------+---  3413

      GCATGATGCATGATAATATTTTTTTATTAATCCTCGTGGAAGGTATAGGCCGGCCGGGTG
3414  ------+---------+---------+---------+---------+---------+---  3473

      AATTTCAAGGGTACCTTTCTTTGATCACTTTCATCATGTCTTTGCATCTTCCAAGAACCA
3474  ------+---------+---------+---------+---------+---------+---  3533

      ATGAGTGCCCATCAAGTGTCCATTTTCCGCGTAATTCCAAATTAAcTAGTACGTGCCACG
3534  ------+---------+---------+---------+---------+---------+---  3593

      TATCGTGCGGAAAGCACGATACCAGCTATCTaCaAACCACCtkrATGTTATGGTGAATCA
3594  ------+---------+---------+---------+---------+---------+---  3653

      TGCATGTAGTCAAAAAACTAGTACGTGCCACGTCAGTCGCACTTGGAACCATGTATTTAA
3654  ------+---------+---------+---------+---------+---------+---  3713

      GGCTCAGTTTGCGGTTCCTAAACTGTGCTATGCTGGACTTATTTTATAATCATCTCTGAA
3714  ------+---------+---------+---------+---------+---------+---  3773

      ACAATAGATTGACCACAAGATATCAGGACTTTCTTCCTTAATTCCCTCTTTCCTTCCTAT
3774  ------+---------+---------+---------+---------+---------+---  3833

      CTGTTACGGTACATGGTCGTGCCGACGTGGGACTGACTCATCAACCTCGAGTTTTGGAAG
3834  ------+---------+---------+---------+---------+---------+---  3893

      TTGCTTATGTAAAGTGTTCGATTCTTTTAGGCTAGCCATAGTGGTAGTATCTTAGCTAGT
3894  ------+---------+---------+---------+---------+---------+---  3953

      ATCATGCACATTGGTTCCACAAAAATACTGATGtGGCAGCTAATTAAGGAGGAkAsATrA
3954  ------+---------+---------+---------+---------+---------+---  4013

      GAkkmGaGyATCATAGGTGGATACCGTATCATAGCGCATATCACGAGAAAAGTTAATGTC
4014  ------+---------+---------+---------+---------+---------+---  4073
```

FIGURE 14 CONTINUED

```
      AAACAAATCTTGTACATCAATTTGCATTGAGATTCTAAATAGCAATAAATATAGCATAAC
4074  ------+---------+---------+---------+---------+---------+---  4133

      TATGATACTACTTCATGATACTACCCACTATAGGGATAATATCATACACAAGTATCATAT
4134  ------+---------+---------+---------+---------+---------+---  4193

      GCATGATACTACTATATGATACTTAGCACTATGGCCAGCCTTATGGAAATTGGTGGAGGA
4194  ------+---------+---------+---------+---------+---------+---  4253

      CGCCAGCACCTTTATTAATTGAATAACAATAATTTTTATCATGTTTTTTTTTCAAGTTCA
4254  ------+---------+---------+---------+---------+---------+---  4313

      TTATGTCAATGTGCATTCATAATCGATGGACTTACCTCGCTTGAATTATTGAACTAACTA
4314  ------+---------+---------+---------+---------+---------+---  4373

      ATTAATGGTCTATGACATGTGTGCAGTCGATTCCGAGGACGGTGGCGTTGGATGAGAAGA
4374  ------+---------+---------+---------+---------+---------+---  4433
                                S  I  P  R  T  V  A  L  D  E  K  T

      CCCGGATGAATCTCCTCCAATGGCCGGTGgaAGGAATCGAGACCCTCCGCCTCAATACCA
4434  ------+---------+---------+---------+---------+---------+---  4493
        R  M  N  L  L  Q  W  P  V  E  G  I  E  T  L  R  L  N  T  I

      TCGACCTTGGCAACATCACCATCGGCACCGGCTCCATCTTCCCCCTCCCCCTCCGGCAAG
4494  ------+---------+---------+---------+---------+---------+---  4553
        D  L  G  N  I  T  I  G  T  G  S  I  F  P  L  P  L  R  Q  A

      CCACTCAGCTCGACAtGgAGGCCTCCTTCCGCCTAGACGCwTCCGCCATAGCTGCCTTCA
4554  ------+---------+---------+---------+---------+---------+---  4613
        T  Q  L  D  M  E  A  S  F  R  L  D  A  S  A  I  A  A  F  N

      ATGAGGTCGACGTTAGCTACAACTGCAGCACCAGTGGCGGTGCCGCTAGCCGTGGCACGC
4614  ------+---------+---------+---------+---------+---------+---  4673
        E  V  D  V  S  Y  N  C  S  T  S  G  G  A  A  S  R  G  T  L

      TCGGCCCCTTCGGCCTCCTAGTCCTCACCACCGCCGACAGTCGCAGCGAACAAATGGCAG
4674  ------+---------+---------+---------+---------+---------+---  4733
        G  P  F  G  L  L  V  L  T  T  A  D  S  R  S  E  Q  M  A  V

      TGTACTTCTACGTGTCCAAGAGCATCGACGGCACGCTCCAGACCAGCTTCTGCCACGACG
4734  ------+---------+---------+---------+---------+---------+---  4793
        Y  F  Y  V  S  K  S  I  D  G  T  L  Q  T  S  F  C  H  D  E

      AGTCCCGCTCGTCTCGGGCCTGGGACGTGGTGAAGCGGGTGGTGGGCAGCACCGTGCCGG
4794  ------+---------+---------+---------+---------+---------+---  4853
        S  R  S  S  R  A  W  D  V  V  K  R  V  V  G  S  T  V  P  V
```

FIGURE 14 CONTINUED

```
      TGCTCCACGGTGAGGCTTTATCTGTCAGGGTGCTCGTGGATCATTCGATCGTAGAGAGCT
4854  ------+---------+---------+---------+---------+---------+---  4913
       L  H  G  E  A  L  S  V  R  V  L  V  D  H  S  I  V  E  S  F

      TCGCGATGGGCGGGAGGTCAACGGTGACGTCGCGGGTATACCCGACGGAGGCCATCTACG
4914  ------+---------+---------+---------+---------+---------+---  4973
       A  M  G  G  R  S  T  V  T  S  R  V  Y  P  T  E  A  I  Y  E

      AGGCGGCGAGGGCGTATGTTTTCAACAACGCCACCGGCTCCACTGTCACCGTCGAGAGAC
4974  ------+---------+---------+---------+---------+---------+---  5033
       A  A  R  A  Y  V  F  N  N  A  T  G  S  T  V  T  V  E  R  L

      TCGTGGTGCACGATATGGACTCGGCATTCATCAAATAAAGAGAACAATAATTTTCTGAGC
5034  ------+---------+---------+---------+---------+---------+---  5093
       V  V  H  D  M  D  S  A  F  I  K  *

      CTAGTATcCaCATGATCATGATATAGTAAGGGAAAAATCATATCTATAAGTTTCCGAACT
5094  ------+---------+---------+---------+---------+---------+---  5153

      TAGTGAAAAAAAAACCTGTAAAAGATATGCAGTCATATACACATGTGAAATTAGGTAGGAA
5154  ------+---------+---------+---------+---------+---------+---  5213

      AATATGATAATCTCGTAGATGAGGAAAAAATATTGTACACCAAACTATTGTAAGTTACAG
5214  ------+---------+---------+---------+---------+---------+---  5273

      TAATGTAATGTAAAAAAAGTTTTTAAGTTACAGAAGGTACATACCGCAAATAATCATATT
5274  ------+---------+---------+---------+---------+---------+---  5333

      ATTTTACCAAGATATTTTTTTCTGGAGTATTCCTTTCAAGTATCTTTTATCTCTAGAATC
5334  ------+---------+---------+---------+---------+---------+---  5393

      TTCTCCAATCATGAGTGGCAACCGAAATGGAGCTCCTGTGTTGCTCCCCGTGTCTCACCC
5394  ------+---------+---------+---------+---------+---------+---  5453

      CTTTCGGCCCCACTGTCATTGGGTGGACCTATTCTCACGGCGGCTGTCCTGAGAAACAAA
5454  ------+---------+---------+---------+---------+---------+---  5513

      AATAGCAGCTGAAATGAAGACACGGCGACACGCAAGCCAGCATCTCTCATTGAACCTGCG
5514  ------+---------+---------+---------+---------+---------+---  5573

      GAGTGAGATAGCTCTCGTGGCGCTGCTCTACTTGACGCGTTTGTCTCATACAACAGCGCA
5574  ------+---------+---------+---------+---------+---------+---  5633

      TGGCTCCTTCATGTCAGGTCCATGATCCACAGATGGTATGATTGGGTTTGGAACATTTTT
5634  ------+---------+---------+---------+---------+---------+---  5693
```

FIGURE 14 CONTINUED

```
     TGGGTTTGTGATATGTCGTAGATACAAAGGGAAATGTCTGAAGCATGCATGGATgGGGTT
5694 ------+---------+---------+---------+---------+---------+---  5753

     CCCTGCTCATGTACTCaAtGTTGATGGATCTGAAwCCGGG ATAGGTTTTGCTTCTGTCt
5754 ------+---------+---------+---------+---------+---------+---  5813

     TGnATTTCTCTTCATGGATTTTCTCCAATGATTTTTTAATGATTTGTTTATCATGGACTT
5814 ------+---------+---------+---------+---------+---------+---  5873

     GTAGGTTAGTTCATGGAATATATTTTTTGCATTGGTTTGCTAGATTTATCAATTTTCATC
5874 ------+---------+---------+---------+---------+---------+---  5933

     TGCTGATAGTCCATATGAACAATGGGTTTGGTACAGATCGAAATTCAAATTCATGGTGTT
5934 ------+---------+---------+---------+---------+---------+---  5993

     TTTGTAAAAAATATCTTTTCCTTCCCAGTTTTTCTATGATGTTAATAATGCATGTATGCT
5994 ------+---------+---------+---------+---------+---------+---  6053

     CATGGAACCGGTGGACTGATGCAGGTATGCAGATTCGTTGCAAACAGAATTGGCTTCATC
6054 ------+---------+---------+---------+---------+---------+---  6113

     ATTGCTTAGAATTTGAGGAAGCATGGTTCCGAGTTGATGTCATTTCTTAGAATCTGATCT
6114 ------+---------+---------+---------+---------+---------+---  6173

     AATGCATACAAGAAAAGGTCTACTAAATTTTTTGACGTTTCAACAAGGTAGAATCCAACG
6174 ------+---------+---------+---------+---------+---------+---  6233

     GTTGGACGCCCAGTTGGTTGTGGTTTTGCAGTTTTGGCTACCTCTAGGCGATCGCTGCTT
6234 ------+---------+---------+---------+---------+---------+---  6293

     GTCCTCTTCATTTTTGTTCCTCGGGGGGTTTCGCGGCGGCTTTTTGCGGTGCGCGGCTGG
6294 ------+---------+---------+---------+---------+---------+---  6353

     GTGCGGTAGATTTGTTGGCGAGCGTAGATTGTTTACTGAGTTTTTTTCTTCTTTGAATTG
6354 ------+---------+---------+---------+---------+---------+---  6413

     TGAGCTACAACTGTTTGTTGAGGTGCATAGTTATCATTGATCAGTTTTGTGTTTGGTGCA
6414 ------+---------+---------+---------+---------+---------+---  6473

     GTTCGGGTAGAGAACAAGATGCCAGGTGCTCTATAGCTTCTTCATTTTGAGACATTATGG
6474 ------+---------+---------+---------+---------+---------+---  6533

     CTTTGGGGTCGACCCCGGTAACAAAAAAGGGATGCATAAAAACTTGGGATCC
6534 ------+---------+---------+---------+---------+------  6585
```

MODIFICATION OF FRUCTAN BIOSYNTHESIS

The present invention relates to the modification of fructan biosynthesis in plants and, more particularly, to enzymes involved in the fructan biosynthetic pathway and nucleic acids encoding such enzymes.

The present invention also relates to regulatory elements and, more particularly, to promoters capable of causing expression of an exogenous gene in plant cells, such promoters being from a gene encoding an enzyme involved in the fructan biosynthetic pathway in plants.

The invention also relates to vectors including the nucleic acids and regulatory elements of the invention, plant cells, plants, seeds and other plant parts transformed with the regulatory elements, nucleic acids and vectors, and methods of using the nucleic acids, regulatory elements and vectors.

Fructans are a class of highly water-soluble polysaccharides which consist of linear or branched fructose chains attached to sucrose. They represent the major non-structural carbohydrate in many plant species.

Fructan synthesis in grasses is complex. Three enzymes (fructosyltransferases) are involved; sucrose:sucrose 1-fructosyltransferase (1-SST); fructan:fructan 1-fructosyltransferase (1-FFT); and sucrose:fructan 6-fructosyltransferase (6-SFT) which synthesise the more complex fructans that prevail in grasses and cereals.

High amounts of fructans have been found to accumulate in ryegrasses (*Lolium* species) and fescues (*Festuca* species) in response to environmental stresses such as drought and cold.

Fructans are associated with various advantageous characters in forage grasses, such as cold and drought tolerance, increased tiller survival, enhanced persistence, good regrowth after cutting or grazing, improved recovery from stress and early spring growth.

Furthermore, fructans in forage grasses contribute significantly to the readily available energy in the feed for grazing ruminant animals. The fermentation processes in the rumen require considerable readily available energy. The improvement of the readily available energy in the rumen can increase the efficiency of rumen digestion. An increased efficiency in rumen digestion leads to an improved conversion of the forage protein fed to the ruminant animal into milk or meat, and to a reduction in nitrogenous waste as environmental pollutant.

Thus, it would be desirable to have methods of manipulating fructan biosynthesis in plants, including grass species such as ryegrasses (*Lolium* species) and fescues (*Festuca* species), thereby facilitating the production of eg. pasture grasses with enhanced tolerance to abiotic stresses, enhanced persistence and improved herbage quality, leading to improved pasture production, improved animal production and reduced environmental pollution.

While nucleic acid sequences encoding some of the enzymes involved in the fructan biosynthetic pathway have been isolated for certain species of plants, there remains a need for materials useful in the modification of fructan biosynthesis in plants, particularly grass species such as ryegrasses and fescues, and also to engineer fructan accumulation in plants species which are naturally fructan-devoid.

Other phenotypic traits which may be improved by transgenic manipulation of plants include disease resistance, mineral content, nutrient quality and drought tolerance.

However, transgenic manipulation of phenotypic traits in plants requires the availability of regulatory elements capable of causing the expression of exogenous genes in plant cells.

It is an object of the present invention to overcome, or at least alleviate, one or more of the difficulties or deficiencies associated with the prior art.

In one aspect, the present invention provides substantially purified or isolated nucleic acids or nucleic acid fragments encoding fructosyl transferase homologues from a ryegrass or fescue species.

The ryegrass (*Lolium*) or fescue (*Festuca*) species may be of any suitable type, including Italian or annual ryegrass, perennial ryegrass, tall fescue, meadow fescue and red fescue. Preferably the ryegrass or fescue species is a ryegrass, more preferably perennial ryegrass (*Lolium perenne*).

The nucleic acid or nucleic acid fragment may be of any suitable type and includes DNA (such as cDNA or genomic DNA) and RNA (such as mRNA) that is single- or double-stranded, optionally containing synthetic, non-natural or altered nucleotide bases, and combinations thereof.

The term "isolated" means that the material is removed from its original environment (eg. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

In a preferred embodiment of this aspect of the invention, the substantially purified or isolated nucleic acid or nucleic acid fragment encodes a sucrose:fructan 6-fructosyltransferase (6-SFT) homologue from a ryegrass (*Lolium*) or fescue (*Festuca*) species. More preferably the substantially purified or isolated nucleic acid includes a nucleotide sequence selected from the group consisting of (a) the sequences shown in FIGS. 1, 10 and 14 hereto (Sequence ID Nos: 1, 9 and 13, respectively); (b) complements of the sequences shown in FIGS. 1, 10 and 14; (c) sequences antisense to the sequences recited in (a) and (b); and (d) functionally active fragments and variants of the sequences recited in (a), (b) and (c).

In a further preferred embodiment of this aspect of the invention, the substantially purified or isolated nucleic acid or nucleic acid fragment encodes a fructan:fructan 1-fructosyltransferase (1-FFT) homologue from a ryegrass (*Lolium*) or fescue (*Festuca*) species. More preferably the substantially purified or isolated nucleic acid or nucleic acid fragment includes a nucleotide sequence selected from the group consisting of (a) the sequence shown in FIG. 2 hereto (Sequence ID No:3); (b) a complement of the sequence shown in FIG. 2 (Sequence ID No:3); (c) sequences antisense to the sequences recited in (a) and (b); and (d) functionally active fragments and variants of the sequences recited in (a), (b) and (c).

In a further preferred embodiment of this aspect of the invention, the substantially purified or isolated nucleic acid or nucleic acid fragment encodes a sucrose:sucrose 1-fructosyltransferase (1-SST) homologue from a ryegrass (*Lolium*) or fescue (*Festuca*) species. More preferably the substantially purified or isolated nucleic acid or nucleic acid fragment includes a nucleotide sequence selected from the group consisting of (a) the sequence shown in FIG. 11 hereto (Sequence ID No: 11); (b) a complement of the sequence shown in FIG. 11 (Sequence ID No: 11); (c) sequences antisense to the sequences recited in (a) and (b); and (d) functionally active fragments and variants of the sequences recited in (a), (b) and (c).

By "functionally active" is meant that the fragment or variant (such as an analogue, derivative or mutant) is capable of modifying fructan biosynthesis in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, more preferably at least approximately 90% identity, most preferably at least approximately 95% identity. Such functionally active variants and fragments include, for example, those having nucleic acid changes which result in conservative amino acid substitutions of one or more residues in the corresponding amino acid sequence. Preferably the fragment has a size of at least 10 nucleotides, more preferably at least 15 nucleotides, most preferably at least 20 nucleotides.

In a second aspect of the present invention there is provided a vector including a nucleic acid or nucleic acid fragment according to the present invention.

In a preferred embodiment of this aspect of the invention, the vector may include a regulatory element such as a promoter, a nucleic acid or nucleic acid fragment according to the present invention and a terminator; said regulatory element, nucleic acid or nucleic acid fragment and terminator being operatively linked.

By "operatively linked" is meant that said regulatory element is capable of causing expression of said nucleic acid or nucleic acid fragment in a plant cell and said terminator is capable of terminating expression of said nucleic acid or nucleic acid fragment in a plant cell. Preferably, said regulatory element is upstream of said nucleic acid or nucleic acid fragment and said terminator is downstream of said nucleic acid or nucleic acid fragment.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or and viable in the plant cell.

The regulatory element and terminator may be of any suitable type and may be endogenous to the target plant cell or may be exogenous, provided that they are functional in the target plant cell.

Preferably the regulatory element is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the plant cell to be transformed (eg. monocotyledon or dicotyledon). Particularly suitable promoters include the Cauliflower Mosaic Virus 35S (CaMV 35S) promoter, the maize Ubiquitin promoter, the rice Actin promoter, the ryegrass endogenous 6-SFT, 1-FFT, 1-SST and invertase promoters.

A variety of terminators which may be employed in the vectors of the present invention are also well known to those skilled in the art. The terminator may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to the regulatory element, the nucleic acid or nucleic acid fragment of the present invention and the terminator, may include further elements necessary for expression of the nucleic acid or nucleic acid fragment, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (npt2) gene, the hygromycin phosphotransferase (hph) gene, the phosphinothricin acetyltransferase (bar or pat) gene], and reporter genes (such as beta-glucuronidase (GUS) gene (gusA)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical GUS assays, thin layer chromatography (TLC), northern and Western blot hybridisation analyses.

Those skilled in the art will appreciate that the various components of the vector are operatively linked, so as to result in expression of said nucleic acid or nucleic acid fragment. Techniques for operatively linking the components of the vector of the present invention are well known to those skilled in the art. Such techniques include the use of linkers, such as synthetic linkers, for example including one or more restriction enzyme sites.

The vectors of the present invention may be incorporated into a variety of plants, including monocotyledons (such as grasses from the genera *Lolium, Festuca, Paspalum, Pennisetum, Panicum* and other forage and turf grasses, corn, oat, sugarcane, wheat and barley), dicotyledons (such as *arabidopsis*, tobacco, legumes, white clover, red clover, subterranean clover, alfalfa, oak, eucalyptus, canola, maple, soybean and chickpea) and gymnosperms. In a preferred embodiment, the vectors are used to transform monocotyledons, preferably grass species such as ryegrasses (*Lolium* species) and fescues (*Festuca* species), more preferably perennial ryegrass (*Lolium perenne*) including forage and turf type cultivars and tall fescue (*Festuca arundinacea*). In an alternative preferred embodiment, the vectors may be used to transform dicotyledons, preferably forage legume species such as clovers (*Trifolium* species) and medics (*Medicago* species), more preferably white clover (*Trifolium repens*), red clover (*Trifolium pratense*), subterranean clover (*Trifolium subterraneum*) and lucerne (*Medicago sativa*). Other key target plants include plants which are naturally fructan devoid, such as potato, sugarbeet and maize.

Techniques for incorporating the vectors of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Cells incorporating the vector of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, eg transformed with, a vector of the present invention.

The plant cell, plant, plant seed or other plant part may be from any suitable species, including monocotyledons, dicotyledons and gymnosperms. In a preferred embodiment the plant cell, plant, plant seed or other plant part may be from a monocotyledon, preferably a grass species, more preferably a ryegrass (*Lolium* species) or fescue (*Festuca* species), even more preferably a ryegrass, most preferably perennial ryegrass including forage- and turf-type cultivars. In an alternate preferred embodiment the plant cell, plant, plant seed or other plant part is from a dicotyledon, preferably forage legume species such as clovers (*Trifolium* species) and medics (*Medicago* species), more preferably white clover (*Trifolium repens*), red clover (*Trifolium pratense*), subterranean clover (*Trifolium subterraneum*) and lucerne (*Medicago sativa*). Other key target plants include plants which are naturally fructan devoid, such as tobacco, potato, sugarbeet and maize.

The present invention also provides a plant, plant seed or other plant part derived from a plant cell of the present invention.

The present invention also provides a plant, plant seed or other plant part derived from a plant of the present invention.

In a further aspect of the present invention there is provided a method of modifying fructan biosynthesis in a plant, said method including introducing into said plant an effective amount of a nucleic acid or nucleic acid fragment and/or a vector according to the present invention.

By "an effective amount" is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

Using the methods and materials of the present invention, plant fructan biosynthesis may be increased, decreased or otherwise modified relative to an untransformed control plant. It may be increased or otherwise modified, for example, by incorporating additional copies of a sense nucleic acid or nucleic acid fragment of the present invention. It may be decreased, for example, by incorporating an antisense nucleic acid or nucleic acid fragment of the present invention. In addition, the number of copies of genes encoding for different enzymes in the fructan biosynthetic pathway may be manipulated to modify the relative amount of each molecule synthesized, thereby altering the composition of fructans produced. Also, the materials and methods of the present invention may be used to engineer fructan accumulation in fructan-devoid plants, particularly forage plants, such as clovers and lucerne. This may in turn provide enhanced quality and/or tolerance to abiotic stresses.

In a still further aspect of the present invention there is provided use of a nucleic acid or nucleic acid fragment according to the present invention, and/or nucleotide sequence information thereof, as a molecular genetic marker.

More particularly, nucleic acids or nucleic acid fragments according to the present invention and/or nucleotide sequence information thereof, may be used as a molecular genetic marker for qualitative trait loci (QTL) tagging, QTL mapping, DNA fingerprinting and in marker assisted selection, and may be used as candidate genes or perfect markers, particularly in ryegrasses and fescues. Even more particularly, nucleic acids or nucleic acid fragments according to the present invention, and/or nucleotide sequence information thereof, may be used as molecular genetic markers in forage and turf grass improvement, eg tagging QTLs for dry matter digestibility, herbage quality, palatability, regrowth after cutting and grazing, cold tolerance, drought tolerance, tiller survival and plant persistence.

In a still further aspect of the present invention there is provided a substantially purified or isolated fructosyl transferase homologue from a ryegrass (*Lolium*) or fescue (*Festuca*) species. Preferably, the fructosyl transferase homologue is a polypeptide selected from the group consisting of the enzymes 6-SFT, 1-SST and 1-FFT, and homologues thereof.

The ryegrass (*Lolium*) or fescue (*Festuca*) species may be of any suitable type, including Italian or annual ryegrass, perennial ryegrass, tall fescue, meadow fescue and red fescue. Preferably the species is a ryegrass, more preferably perennial ryegrass (*L. perenne*).

In a preferred embodiment of this aspect of the invention, the substantially purified or isolated 6-SFT homologue includes an amino acid sequence selected from the group consisting of sequences shown in FIGS. 1, 10 and 14 hereto (Sequence ID Nos: 2, 10 and 14 respectively); and functionally active fragments and variants thereof.

In a further preferred embodiment of this aspect of the invention, the substantially purified or isolated 1-FFT homologue includes an amino acid sequence selected from the group consisting of the sequence shown in FIG. 2 hereto (Sequence ID No: 4); and functionally active fragments and variants thereof.

In a still further preferred embodiment of this aspect of the invention, the substantially purified or isolated 1-SST homologue includes an amino acid sequence selected from the group consisting of the sequence shown in FIG. 11 hereto (Sequence ID No: 12); and functionally active fragments and variants thereof.

By "functionally active" in this context is meant that the fragment or variant has one or more of the biological properties of the proteins 6-SFT, 1-SST and 1-FFT, and homologues thereof, respectively. Additions, deletions, substitutions and derivatizations of one or more of the amino acids are contemplated so long as the modifications do not result in loss of functional activity of the fragment or variant. Preferably the fragment or variant has at least approximately 60% identity to the relevant part of the above mentioned sequence, more preferably at least approximately 80% identity, most preferably at least approximately 90% identity. Such functionally active variants and fragments include, for example, those having conservative amino acid substitutions of one or more residues in the corresponding amino acid sequence. Preferably the fragment has a size of at least 10 amino acids, more preferably at least 15 amino acids, most preferably at least 20 amino acids.

In a further embodiment of this aspect of the invention, there is provided a polypeptide recombinantly produced from a nucleic acid or nucleic acid fragment according to the present invention. Techniques for recombinantly producing polypeptides are well known to those skilled in the art.

In a still further aspect of the present invention there is provided a fructan or modified fructan substantially or partially purified or isolated from a plant, plant seed or other plant part of the present invention.

Such fructans may be modified from naturally occurring fructans in terms of length, the degree of polymerisation (number of fructose units), degree of branching and/or nature of linkages between fructose units.

Such fructans may be isolated from plants, plant seeds or other plant parts of plants which are naturally fructan-accumulators but have manipulated fructan accumulation (such as ryegrass, onion, artichoke) or from plants, plant seeds or other plant parts of plants which are naturally fructan-devoid but have been manipulated to produce fructans (such as tobacco, sugarbeet, potato, maize, clovers, lucerne).

These fructans may have important industrial uses, for example as low-calorie sweeteners.

In a still further aspect, the present invention provides an isolated regulatory element capable of causing expression of an exogenous gene in plant cells.

The regulatory element may be a nucleic acid molecule, including DNA (such as cDNA or genomic DNA) and RNA (such as mRNA) that is single- or double-stranded, optionally containing synthetic, non-natural or altered nucleotide bases, and combinations thereof.

Preferably the regulatory element includes a promoter, more preferably a fructosyl transferase homologue promoter, even more preferably a promoter from 1-FFT, 1-SST, 1-FFT or homologues thereof. Preferably, the promoter is from a ryegrass (*Lolium*) or fescue (*Festuca*) species, more preferably a ryegrass, most preferably perennial ryegrass (*Lolium perenne*).

In a particularly preferred embodiment of this aspect of the invention, the regulatory element includes a promoter from the 6-SFT cDNA homologues Lp6SFT1 and Lp6SFT3 from perennial ryegrass.

Preferably the regulatory element includes a nucleotide sequence including the first approximately 5700 nucleotides of the sequence shown in FIG. 10—hereto (Sequence ID No: 9); the first approximately 1600 nucleotides of the sequence shown in FIG. 11 hereto (Sequence ID No: 11); or a functionally active fragment or variant thereof.

By "functionally active" in this context is meant that the fragment or variant (such as an analogue, derivative or mutant) is capable of causing expression of a transgene in plant cells. Such variants include naturally occurring allelic variants and non-naturally occurring variants. Additions, deletions, substitutions and derivatizations of one or more of the nucleotides are contemplated so long as the modifications do not result in loss of functional activity of the regulatory element. Preferably the functionally active fragment or variant has at least approximately 80% identity to the relevant part of the above sequence, more preferably at least approximately 90% identity, most preferably at least approximately 95% identity. Preferably the fragment has a size of at least 100 nucleotides, more preferably at least 150 nucleotides, most preferably at least 200 nucleotides.

In a particularly preferred embodiment of this aspect of the invention, the regulatory element includes a nucleotide sequence selected from the group consisting of the HindIII-EcoRI fragment of Lp6SFT1 shown in FIG. 12 hereto; and the XbaI-EcoRI fragment of Lp6SFT1 shown in FIG. 12 hereto; or a functionally active fragment or variant thereof.

By an "exogenous gene" is meant a gene not natively linked to said regulatory element. In certain embodiments of the present invention the exogenous gene is also not natively found in the relevant plant or plant cell.

The exogenous gene may be of any suitable type. The exogenous gene may be a nucleic acid such as DNA (e.g. cDNA or genomic DNA) or RNA (e.g. mRNA) that is single- or double-stranded, optionally containing synthetic, non-natural or altered nucleotide bases, and combinations thereof. The exogenous gene may correspond to a target gene, for example a gene capable of influencing disease resistance, herbage digestibility, nutrient quality, mineral content or drought tolerance or be a fragment or variant (such as an analogue, derivative or mutant) thereof which is capable of modifying expression of said target gene. Such variants include nucleic acid sequences which are antisense to said target gene or an analogue, derivative, mutant or fragment thereof. The transgene may code for a protein or RNA sequence depending the target condition and whether down or up-regulation of gene expression is required. Preferably, the target gene is selected from exogenous coding sequences coding for mRNA for a protein, this protein may be of bacterial origin (such as enzymes involved in cell wall modification and cell wall metabolism, cytokinin biosynthesis), or eukaryotic origin (such as pharmaceutically active polypeptides) or of plant origin (such as enzymes involved in the synthesis of phenolic compounds, synthesis of fructans cell wall metabolism, sugar metabolism, lignin biosynthesis). Preferably, the target gene is selected from the group comprising 1-SST, 1-FFT, 6-SFT, O-methyltransferase, 4 coumarate CoA-ligase, cinnamoyl CoA reductase, cinnamyl alcohol dehydrogenase, cinnamate 4 hydroxylase, phenolase, laccase, peroxidase, coniferol glucosyl transferase, coniferin beta-glucosidase, phenylalanine ammonia lyase, ferulate 5-hydroxylase, chitinase, glucanase, isopentenyltransferase, xylanase.

The plant cells, in which the regulatory element of the present invention is capable of causing expression of an exogenous gene, may be of any suitable type. The plant cells may be from monocotyledons (such as grasses from the genera *Lolium, Festuca, Paspalum, Pennisetum, Panicum* and other forage and turf grasses, corn, oat, sugarcane, wheat and barley), dicotyledons (such as *arabidopsis*, tobacco, legumes, alfalfa, oak, eucalyptus and maple) and gymnosperms. Preferably the plant cells are from a monocotyledon, more preferably a grass species such as a ryegrass (*Lolium*) or fescue (*Festuca*) species, even more preferably a ryegrass, most preferably perennial ryegrass (*Lolium perenne*). Other key target plants include plants which are naturally fructan devoid, such as tobacco, potato, sugarbeet and maize.

The regulatory element according to the present invention may be used to express exogenous genes to which it is operatively linked in the production of transgenic plants.

Accordingly, in a further aspect of the present invention there is provided a vector including a regulatory element according to the present invention.

In a preferred embodiment of this aspect of the invention, the vector may include a regulatory element according to the present invention, an exogenous gene as hereinbefore described, and a terminator; said regulatory element, exogenous gene and terminator being operatively linked, such that said regulatory element is capable of causing expression of said exogenous gene in plant cells. Preferably, said regulatory element is upstream of said exogenous gene and said terminator is downstream of said exogenous gene.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*; derivatives of the Ri plasmid from *Agrobacterium rhizogenes*, phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the plant cell.

The terminator may be of any suitable type and includes for example polyadenylation signals, such as the Cauliflower Mosaic Virus 35S polyA (CaMV 35S polyA) and other terminators from the nopaline synthase (nos) and the octopine synthase (ocs) genes.

The vector, in addition to the regulatory element, the exogenous nucleic acid and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (npt2) gene, the hygromycin phosphotransferase (hph) gene, the phosphinothricin acetyltransferase (bar or pat) gene], and reporter genes (such as beta-glucuronidase (GUS) gene (gusA)]. The vector may also contain a ribosome binding site for translation initiation. The vector may also include appropriate sequences for amplifying expression.

The regulatory element of the present invention may also be used with other full promoters or partial promoter elements.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical GUS assays, northern and Western blot hybridisation analyses.

Those skilled in the art will appreciate that the various components of the vector are operatively linked, so as to result in expression of said transgene. Techniques for operatively linking the components of the vector of the present invention are well known to those skilled in the art. Such techniques include the use of linkers, such as synthetic linkers, for example including one or more restriction sites.

The vectors of the present invention may be incorporated into a variety of plants, including monocotyledons, dicotyledons and gymnosperms. In a preferred embodiment the vectors are used to transform monocotyledons, preferably grass species such as ryegrasses (*Lolium* species) and fescues (*Festuca* species), more preferably perennial ryegrass (*Lolium perenne*) including forage- and turf-type cultivars.

Techniques for incorporating the vectors of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Cells incorporating the vector of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, eg. transformed with, a vector of the present invention.

The plant cell, plant, plant seed or other plant part may be from any suitable species, including monocotyledons, dicotyledons and gymnosperms. In a preferred embodiment the plant cell, plant, plant seed or other plant part is from a monocotyledon, preferably a grass species, more preferably a ryegrass (*Lolium* species) or fescue (*Festuca* species), even more preferably perennial ryegrass (*Lolium perenne*), including forage- and turf-type cultivars.

The present invention also provides a plant, plant seed, or other plant part derived from a plant cell of the present invention.

The present invention also provides a plant, plant seed or other plant part derived from a plant of the present invention.

In a still further aspect of the present invention there is provided a recombinant plant genome including a regulatory element according to the present invention.

In a preferred embodiment of this aspect of the invention the recombinant plant genome further includes an exogenous gene operatively linked to said regulatory element.

In a further aspect of the present invention there is provided a method for expressing an exogenous gene in plant cells, said method including introducing into said plant cells an effective amount of a regulatory element and/or a vector according to the present invention.

By "an effective amount" is meant an amount sufficient to result in an identifiable phenotypic change in said plant cells or a plant, plant seed or other plant part derived therefrom. Such amounts can be readily determined by an appropriately skilled person, taking into account the type of plant cell, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

The present invention will now be more fully described with reference to the accompanying Examples and drawings. It should be understood, however, that the description following is illustrative only and should not be taken in any way as a restriction on the generality of the invention described above.

IN THE FIGURES

FIG. 1 shows the nucleotide (Sequence ID No: 1) and amino acid (Sequence ID No: 2) sequences of Lp6SFT1.

FIG. 2 shows the nucleotide (Sequence ID No: 3) and amino acid (Sequence ID No: 4) sequences of Lp6SFT2.

Figure 3:
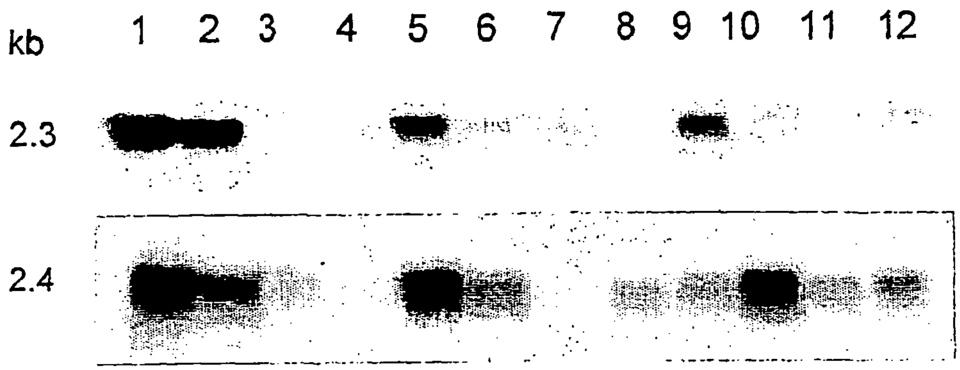

FIG. 3 shows a northern hybridisation analysis of total RNA isolated from different organs and developmental stages of perennial ryegrass and probed with Lp6SFT1 (upper blot) and Lp6SFT2 (lower blot). Lanes 1-10 contain RNA from: 1 cm seedlings—roots (lane 1), shoots (lane 5); 4-6 cm seedlings—roots (lane2), shoots (lane 6); 6 week plantlets—roots (lane 3), shoots (lane 7), stem (lane 9); 10 week plantlets—roots (lane 4), shoots (lane 8), stem (lane 10). Lanes 11 and 12 contain RNA from mature, whole plant tissue from *Phalaris* and *Festuca.*

Figure 4:
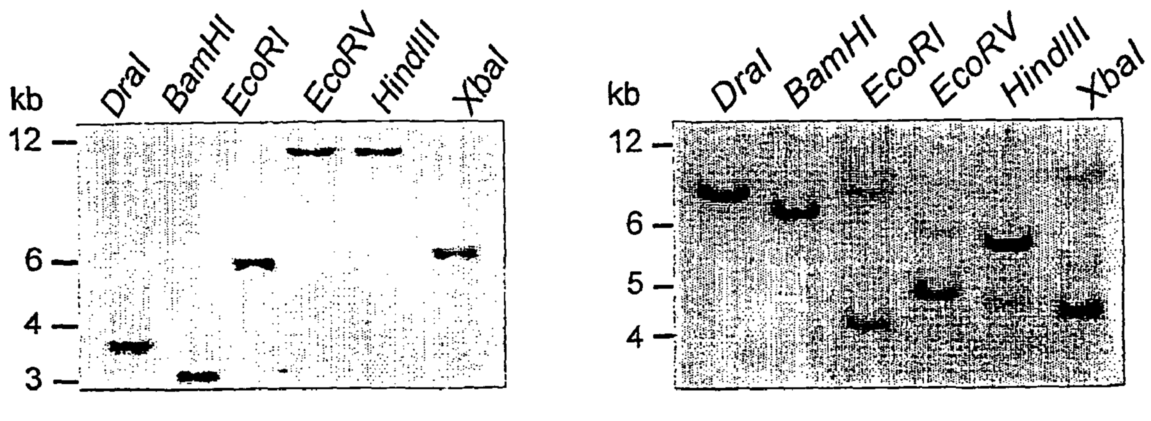

FIG. 4 shows Southern hybridisation analysis. 10 μg of digested perennial ryegrass genomic DNA was separated on a 1.0% agarose gel, transferred to Hybond N membrane and then hybridised with an Lp6SFT1 (left blot) and Lp6SFT2 (right blot) probe respectively.

Figure 5:
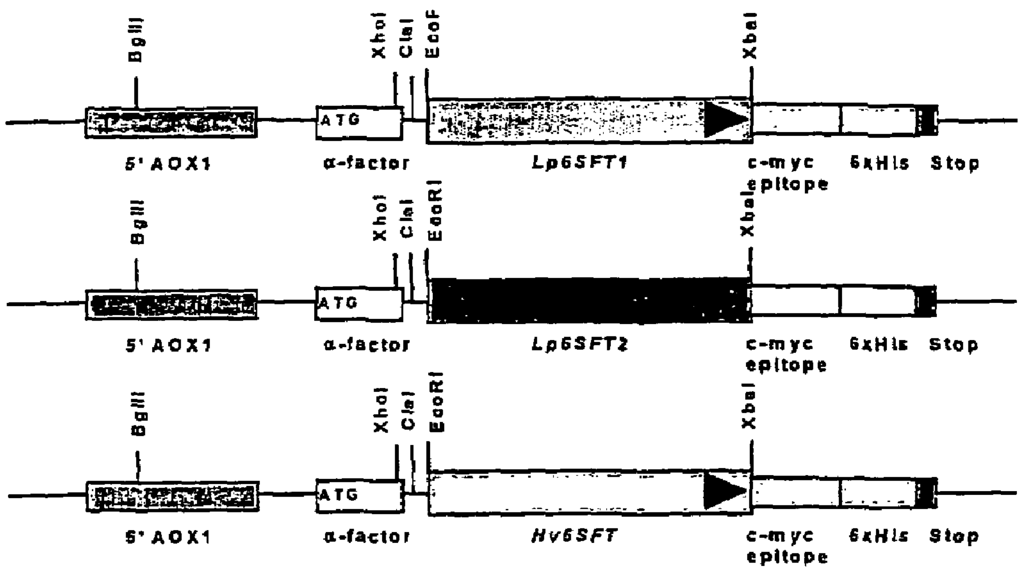

FIG. 5 shows the cDNAs encoding Lp6SFT1, Lp6SFT2 and the barley Hv6SFT minus the 5' targeting signal cloned into the yeast transformation secretory plasmid pPICZαC.

Figure 6:
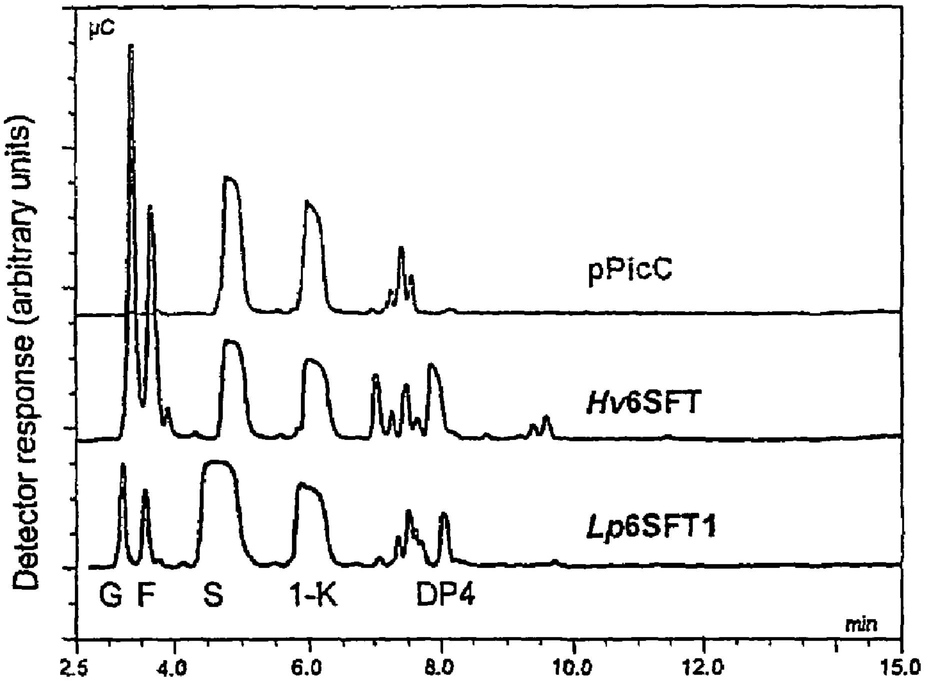

FIG. 6 shows high performance anion exchange chromatography (HPAEC) traces of empty vector, Hv6SFT positive control corresponding to barley 6-SFT (Hv6SFT), and Lp6SFT1 incubated with 50 mM sucrose and 50 mM 1-kestose for 48 h at 4° C. Peaks represent Glucose (G), Fructose (F), Sucrose (S), 1-Kestose (1-K), and DP4 fructan.

Figure 7A:
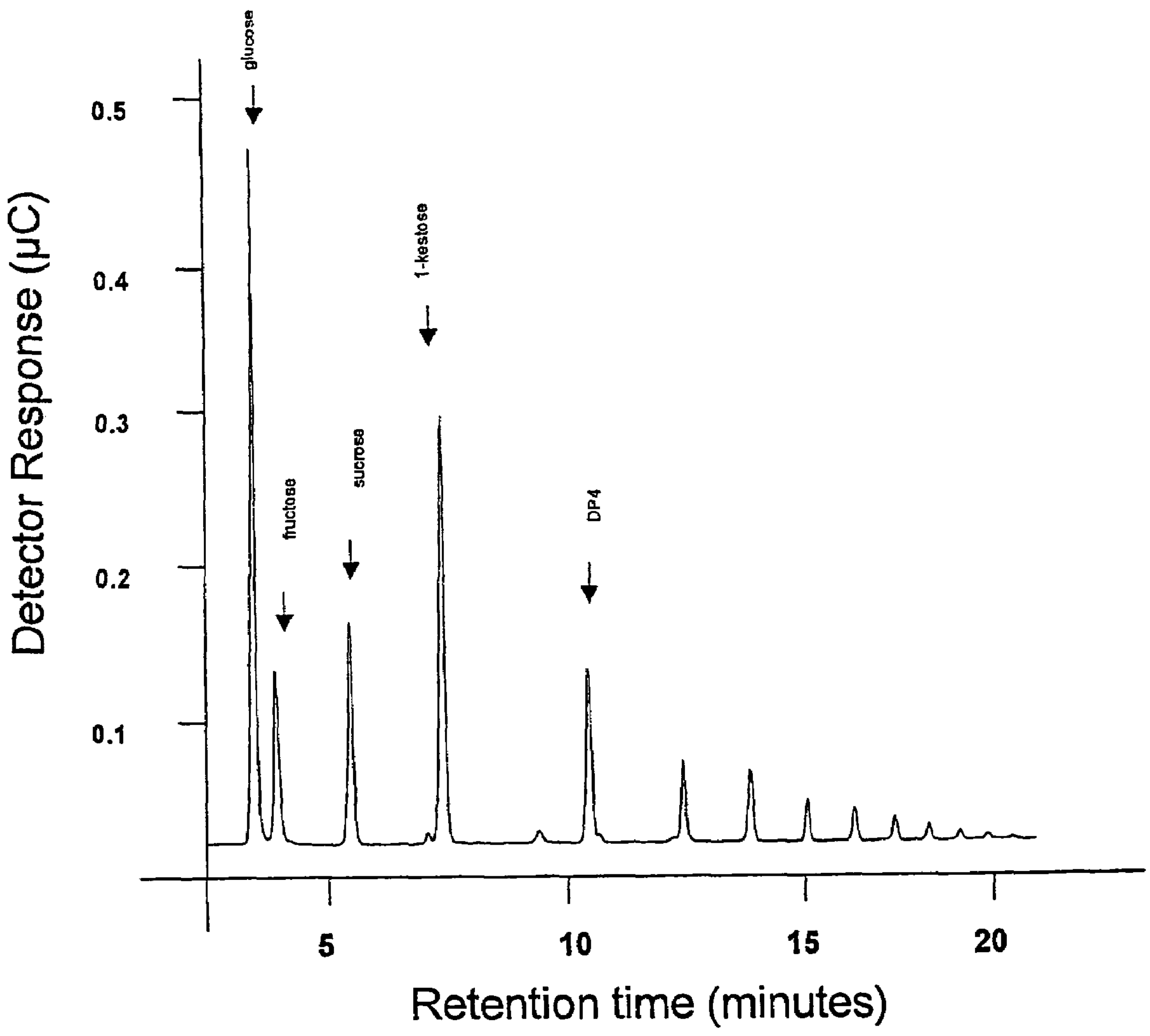
Figure 7B:
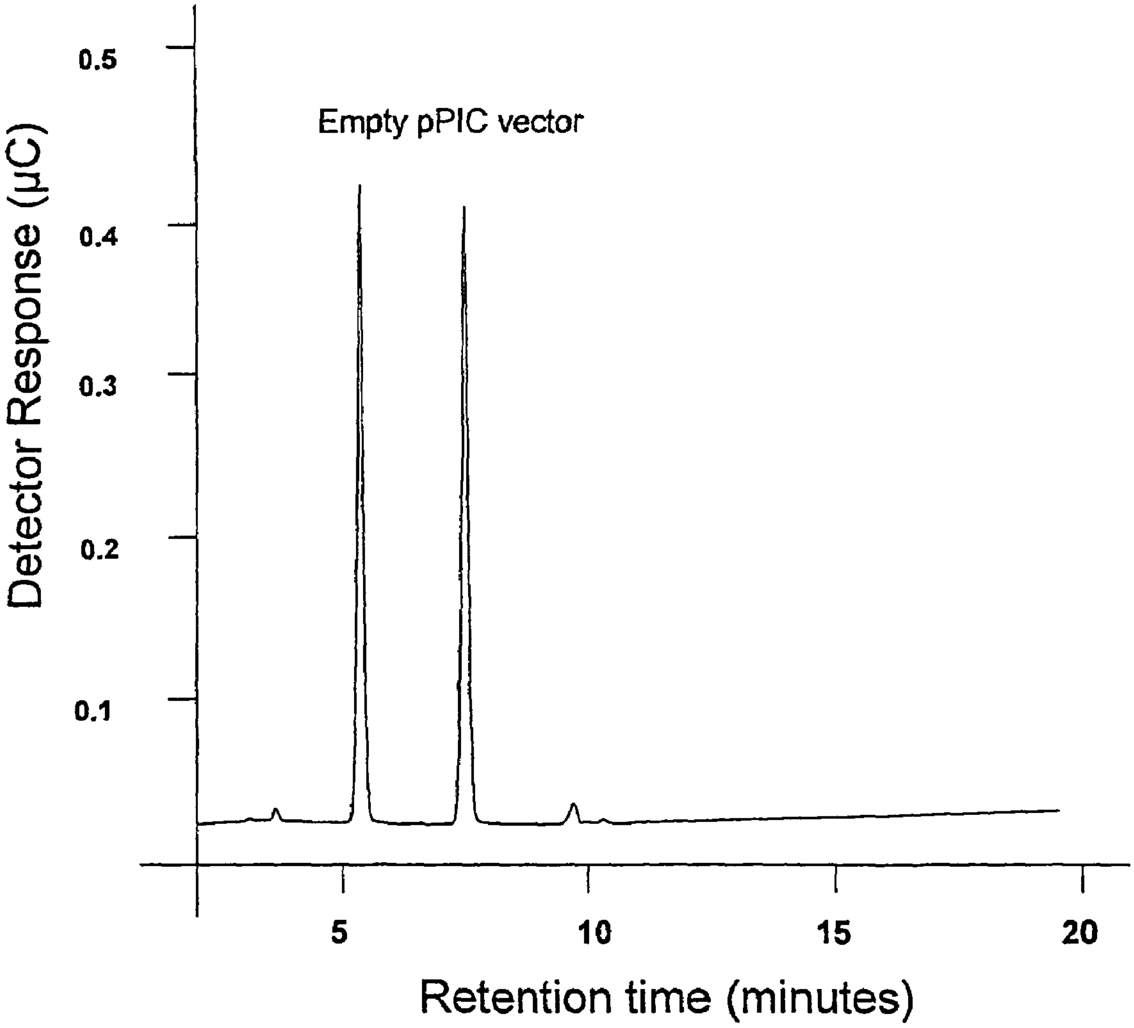

FIG. 7 shows A) pPicαLp6SFT2 (yeast transformation vector for Lp6SFT2 from FIG. 5) expressed in *Pichia pastoris* over 48 hours, 15 μg total protein was added to 50 mM sucrose and 50 mM 1-Kestose and incubated 6 hours at 4° C. The sample was diluted 4×, filtered and analysed using HPAEC. B) pPicα (empty vector) expressed in *Pichia pastoris* over 48 hours, an aliquot of supernatant was added to 50 mM sucrose and 50 mM 1-Kestose and incubated 6 hours at 4° C. The sample was diluted 4×, filtered and analysed using HPAEC.

FIG. 8 shows the nucleotide (Sequence ID No: 5) and amino acid (Sequence ID No: 6) sequences of partial cDNA clone Lp4Ad.

FIG. 9 shows the nucleotide (Sequence ID No: 7) and amino acid (Sequence ID No: 8) sequences of partial cDNA clone Lp6Cb.

FIG. 10 shows the nucleotide (Sequence ID No: 9) and amino acid (Sequence ID No: 10) sequences of genomic clone Lp6SFT1 from perennial ryegrass.

FIG. 11 shows the nucleotide (Sequence ID No: 11) and amino acid (Sequence ID No: 12) sequences of genomic clone Lp6SFT3 from perennial ryegrass.

Figure 12:
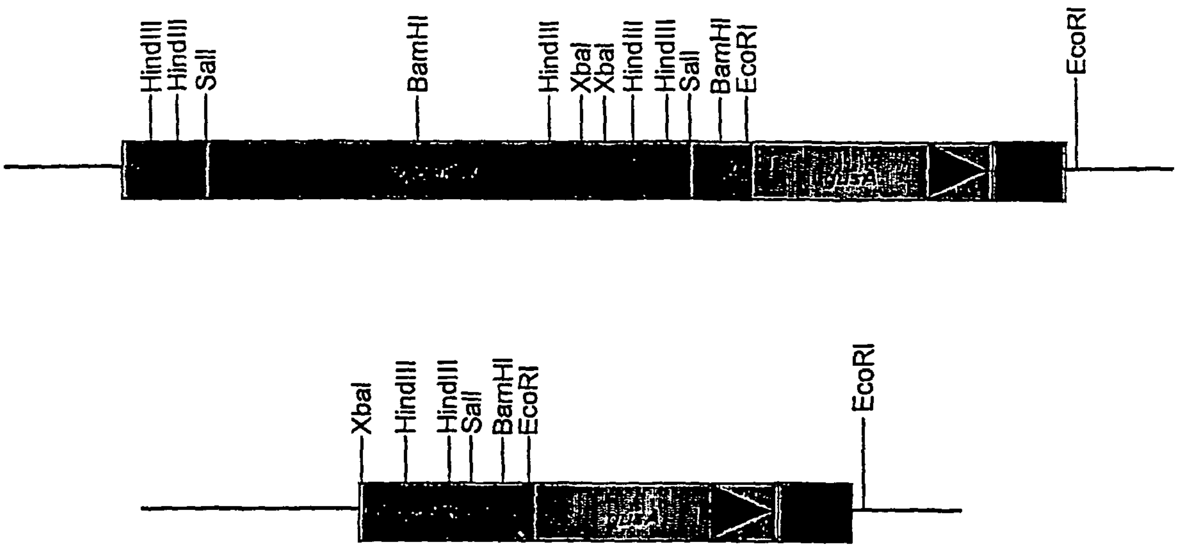

FIG. 12 shows a chimeric gusA gene under the control of the Lp6SFT1 promoter (promoter sequence from Sequence ID No: 9).

Figure 13:
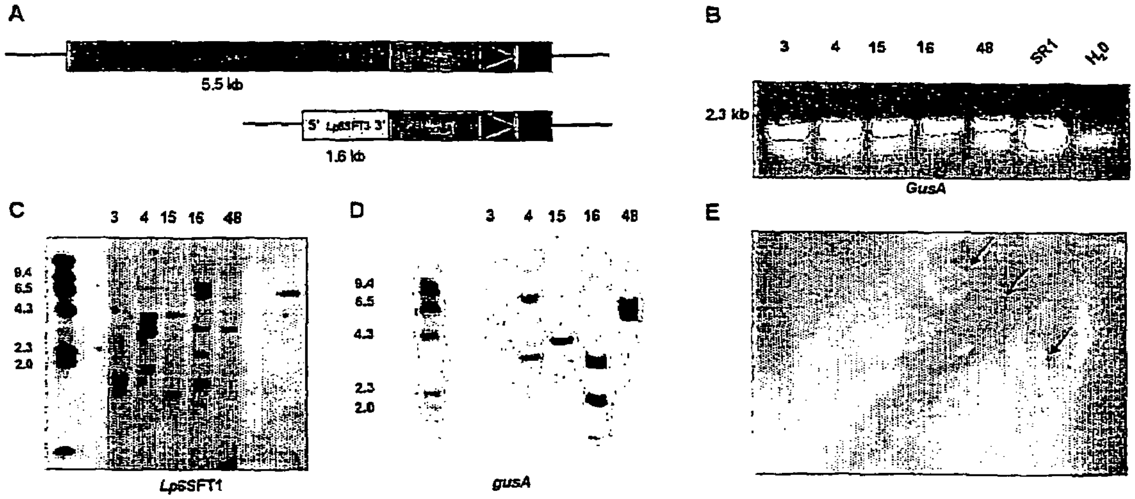

FIG. 13 shows A) Tobacco protoplasts were transformed with the vectors carrying the Lp6SFT1 or Lp6SFT3 promoter fused to the gusA gene. B) PCR analysis of 5 transformants and positive (SR1) and negative ($H_2O$) controls. C) Southern hybridisation analysis of DNA from 5 transformants using part of the Lp6SFT1 promoter as the probe. D) Southern hybridisation analysis of DNA from 5 transformants using part of the gusA gene as the probe. E) Histochemical staining of plant tissue for activity of the gusA protein to assess the expression of the Lp6SFT1 promoter.

FIG. 14 shows the nucleotide (Sequence ID No: 13) and amino acid (Sequence ID No: 14) sequences of Lp6SFT4.

Figure 15:
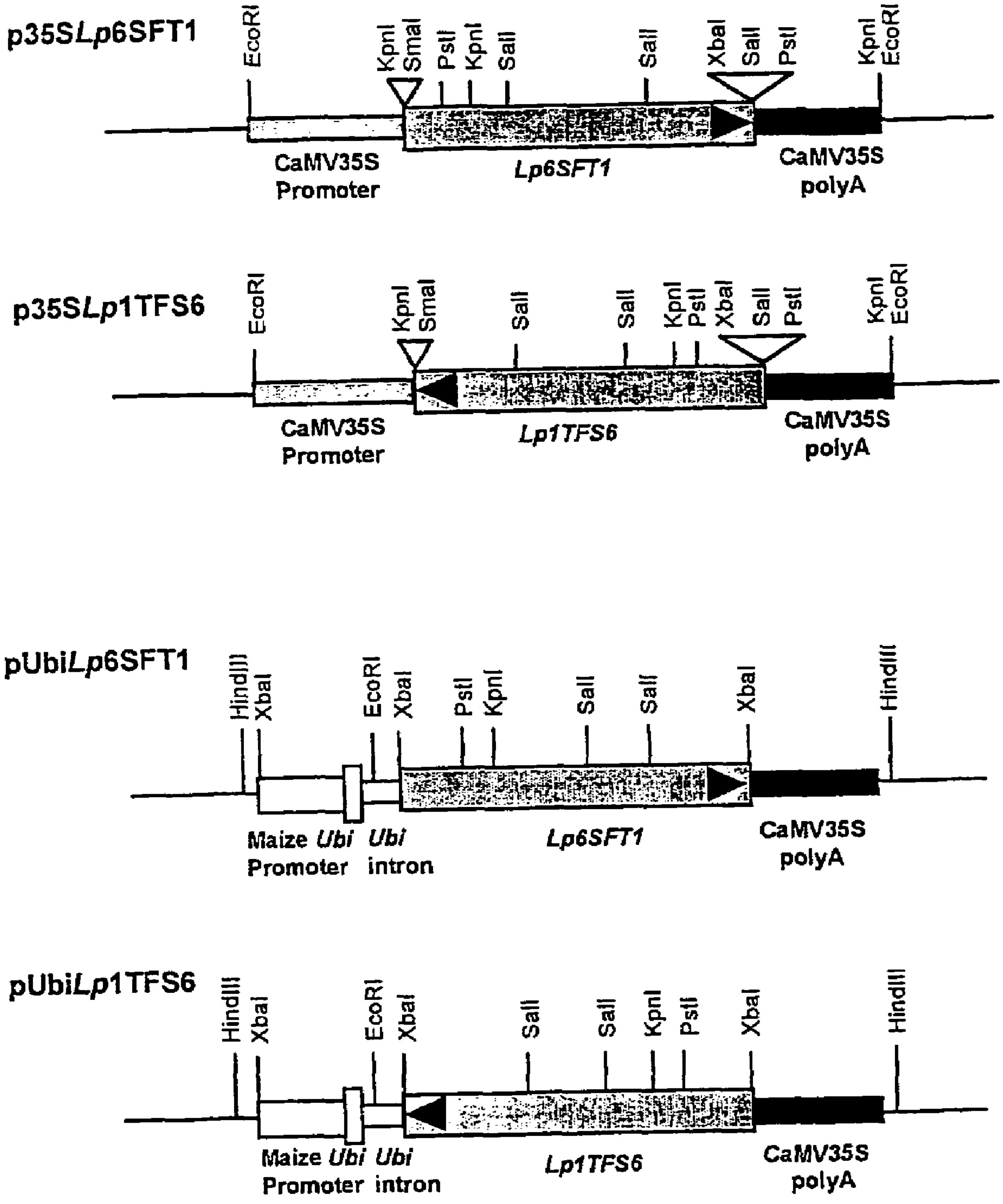
Figure 15:
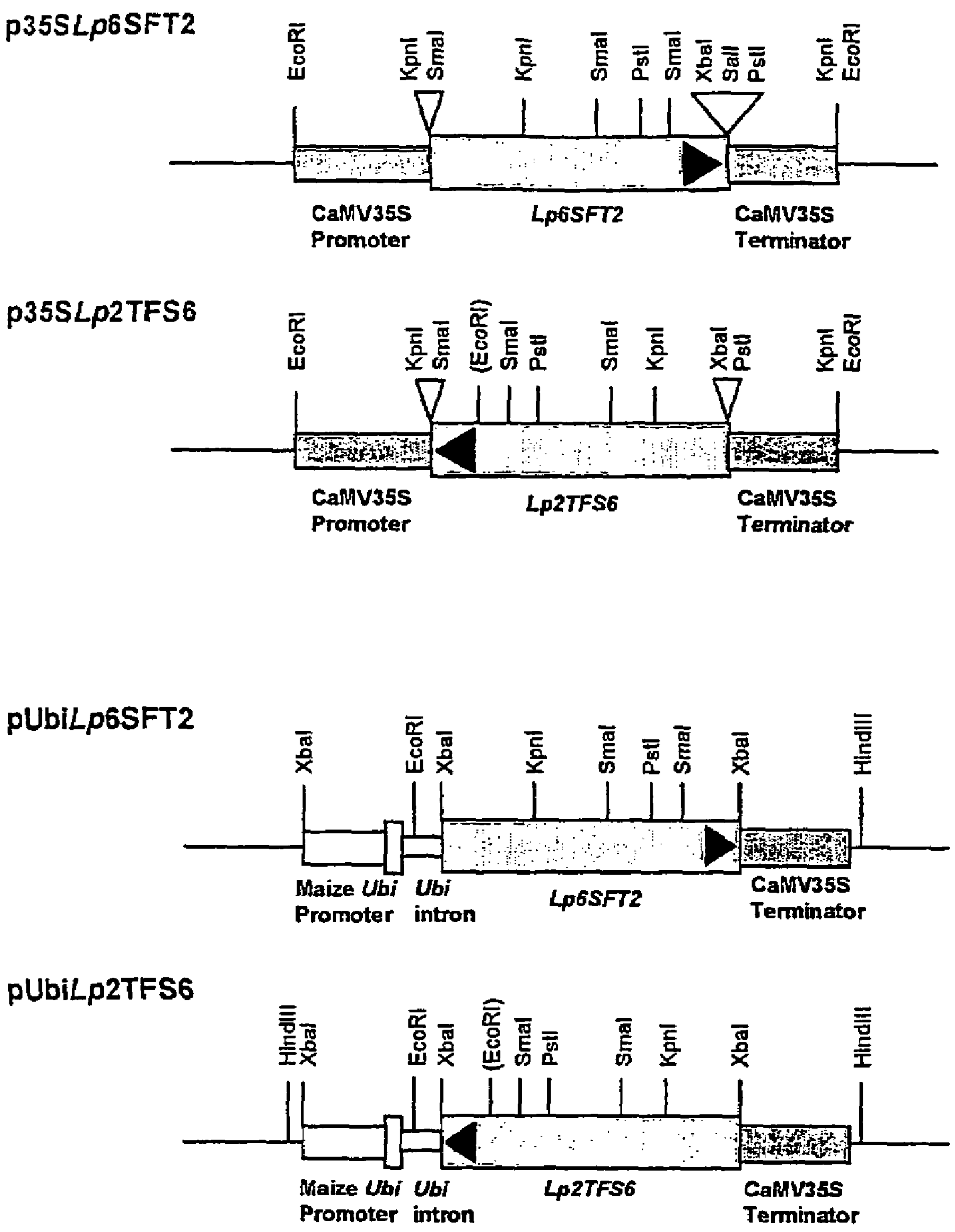

FIG. 15 shows sense and antisense Lp6SFT1 and Lp6FT2 transformation vectors under the control of the CaMV 35S promoter and the maize Ubiquitin promoter.

Figure 16:
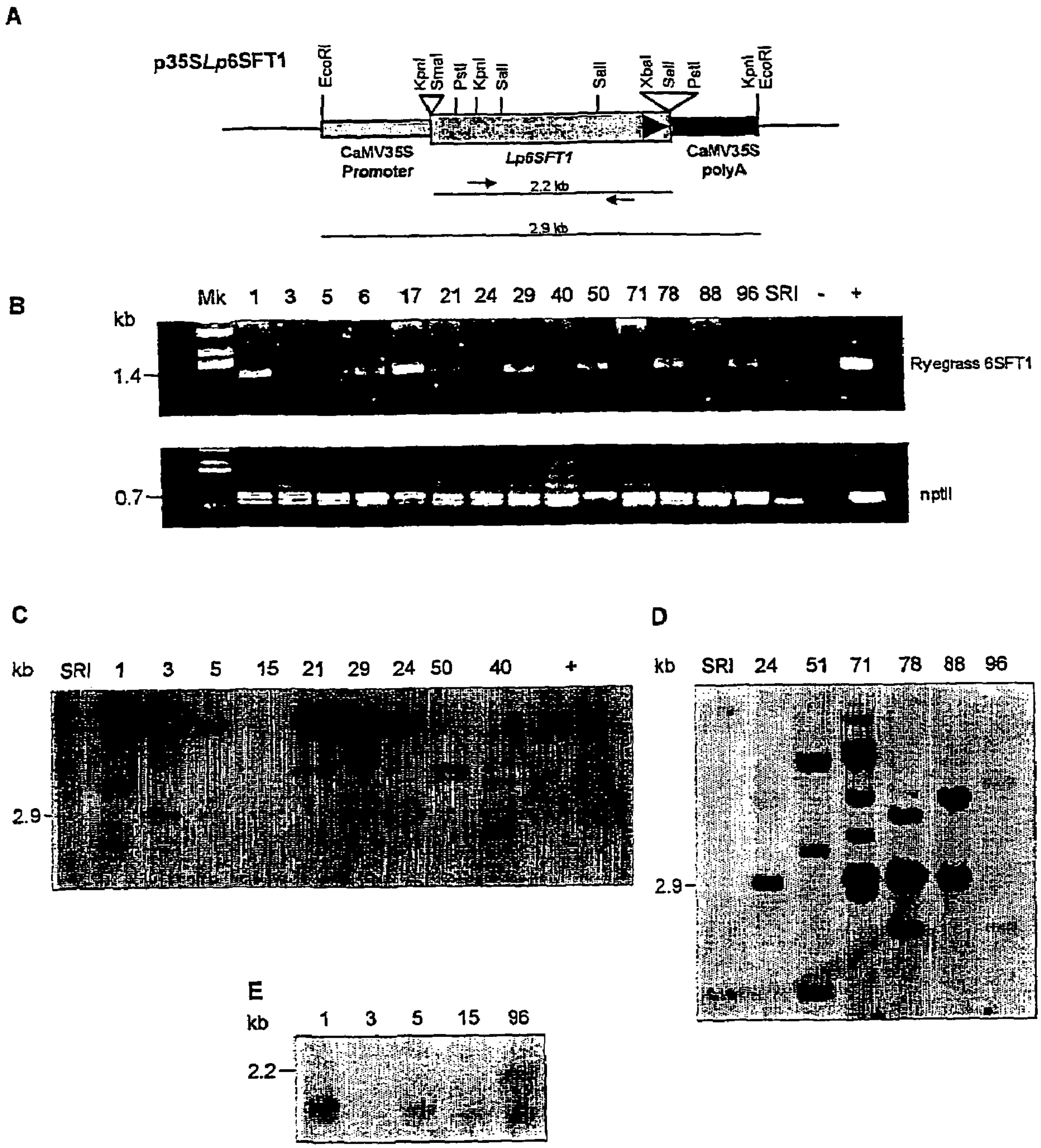

FIG. 16 shows molecular analysis of transgenic tobacco carrying the sense Lp6SFT1 transgene. A) Plasmid map of transformation vector carrying a chimeric sense Lp6SFT1 gene under the control of the CaMV 35S promoter; B) PCR analysis of 14 independent transgenic tobacco clones cotransformed with a chimeric neomycin phosphotransferase (npt2) gene and a chimeric Lp6SFT1 gene; C-D) Southern hybridization analysis of 14 independent transgenic tobacco plants from B) using an Lp6SFT1-specific hybridization probe; E) Northern hybridization analysis of 5 independent transgenic tobacco plants from CD) using an LpSSFT1-specific hybridization probe. SRI=untransformed tobacco negative control, +=plasmid DNA positive control, −=water negative control.

Figure 17:
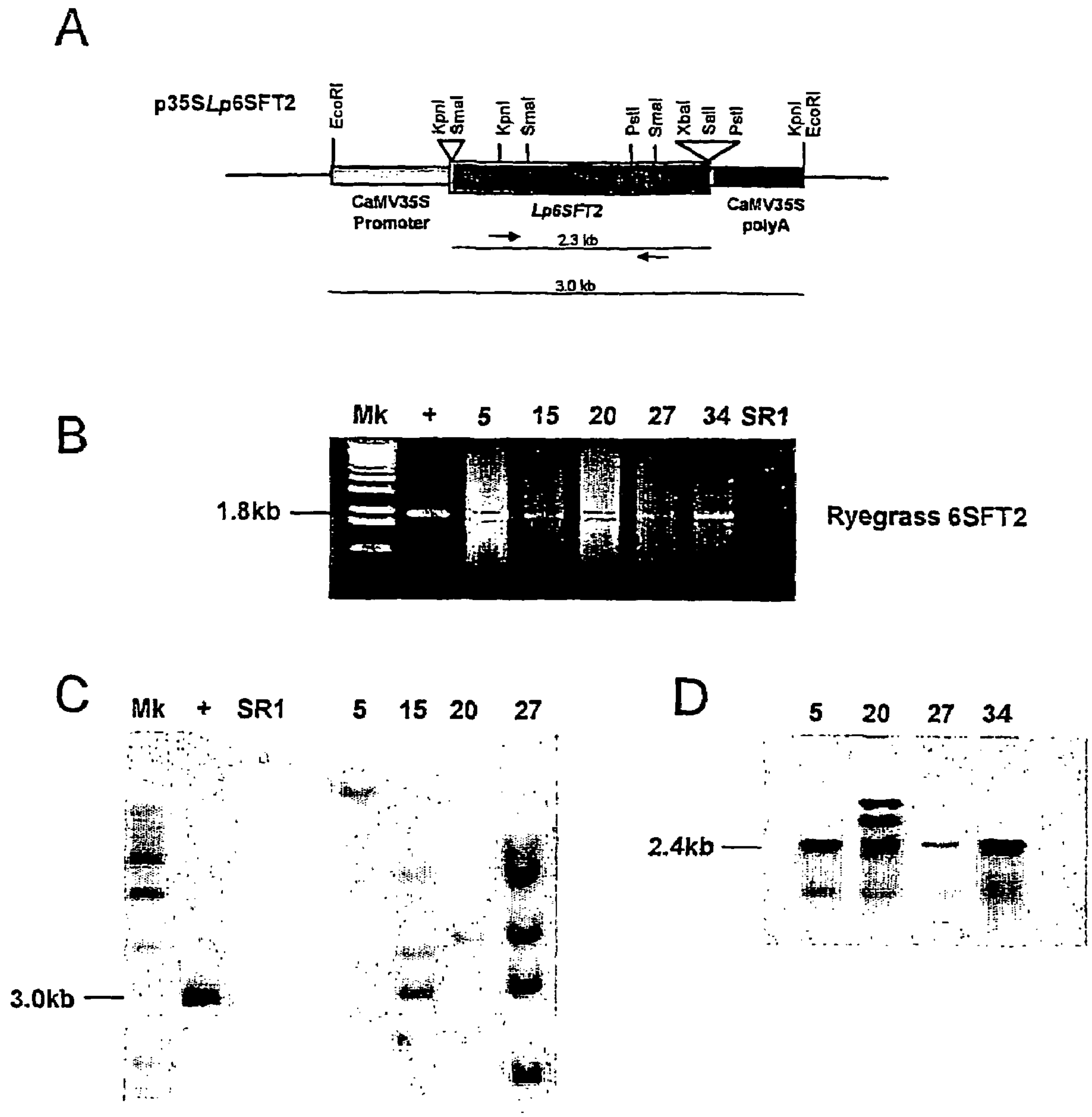

FIG. 17 shows molecular analysis of transgenic tobacco carrying the sense Lp6SFT2 transgene. A) Plasmid map of transformation vector carrying a chimeric sense Lp6SFT2 gene under the control of the CaMV 35S promoter; B) PCR anaylsis of independent transgenic tobacco clones transformed with the chimeric Lp6SFT2 gene from A); C) Southern hybridization analysis of independent transgenic tobacco plants from B) using an Lp6SFT2-specific hybridization probe; D) Northern hybridization analysis of independent transgenic tobacco plants using an Lp6SFT2-specific hybridization probe. SRI=untransformed tobacco negative control, +=plasmid DNA positive control, −=water negative control.

Figure 18:
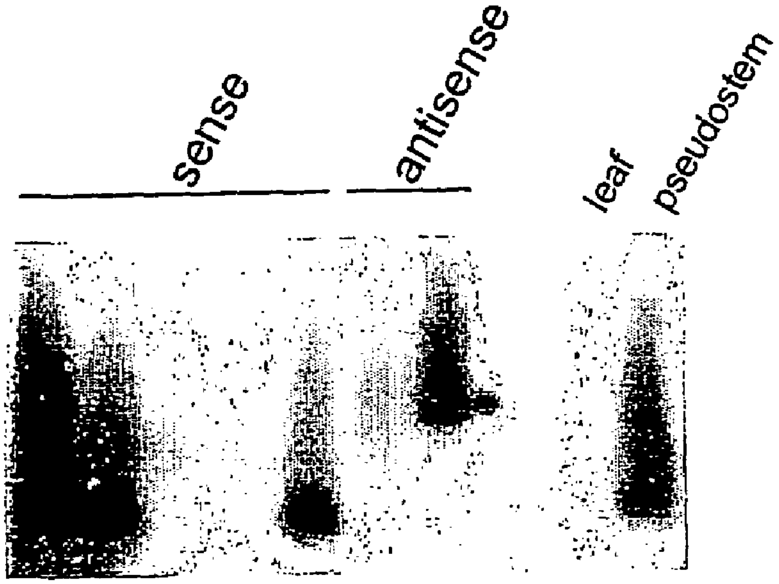
Figure 18:
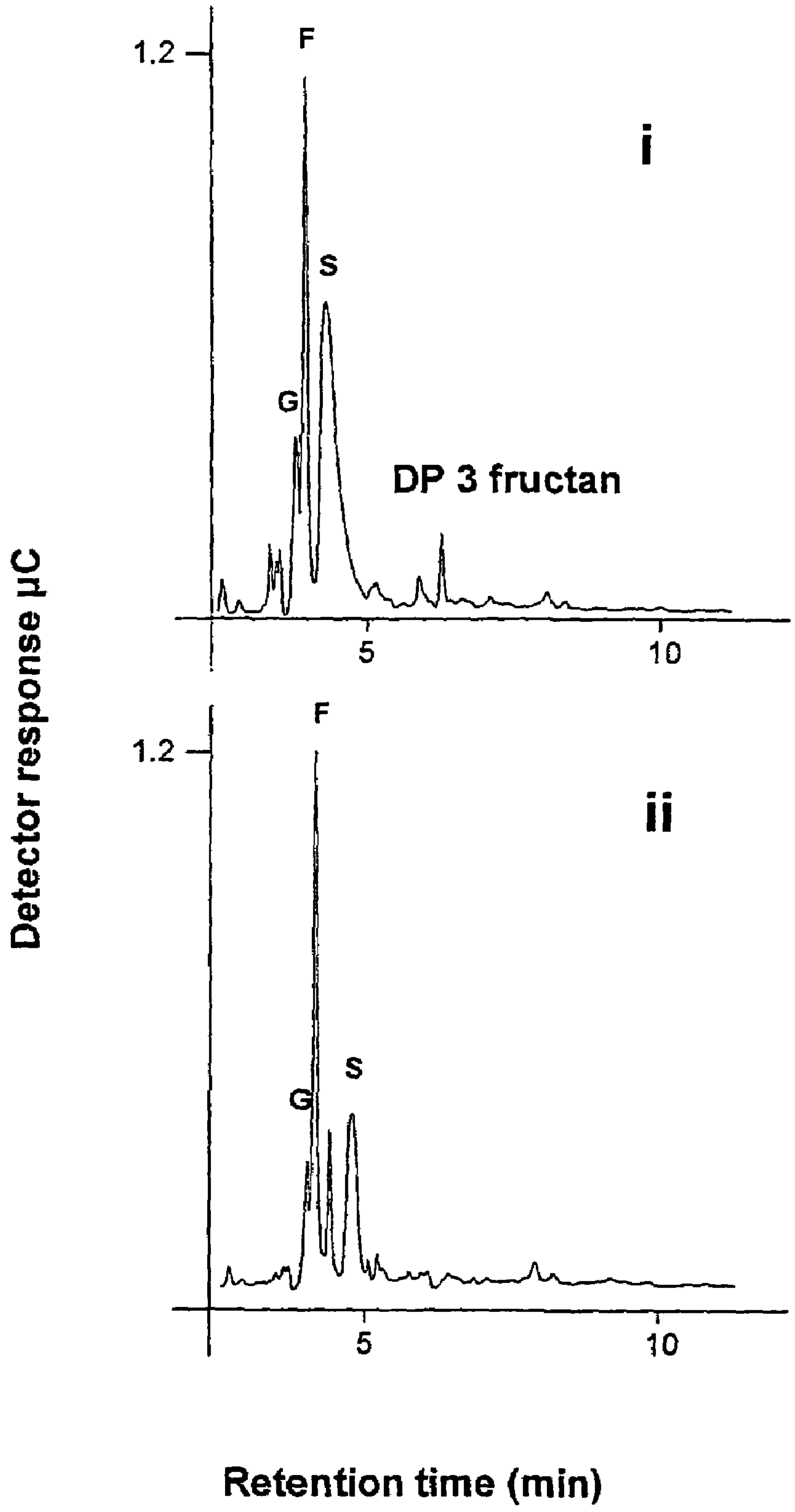

FIG. 18 shows A) Northern hybridisation analysis of T1 tobacco transgenic plants using a 2 kb Lp6SFT2-specific hybridization probe and RNA isolated from ryegrass pseudostems as positive control; B) Water soluble carbohydrates were isolated from callus from Lp6SFT2 sense and antisense transgenic T1 tobacco plants grown in the dark for 1 month: (i) sugars extracted from a northern positive sense transgenic tobacco plant, (ii) sugars extracted from an antisense control transgenic tobacco plant. The extracts were analysed by HPAEC and retention times checked against pure standards and fructan preparations from ryegrass.

Figure 19:
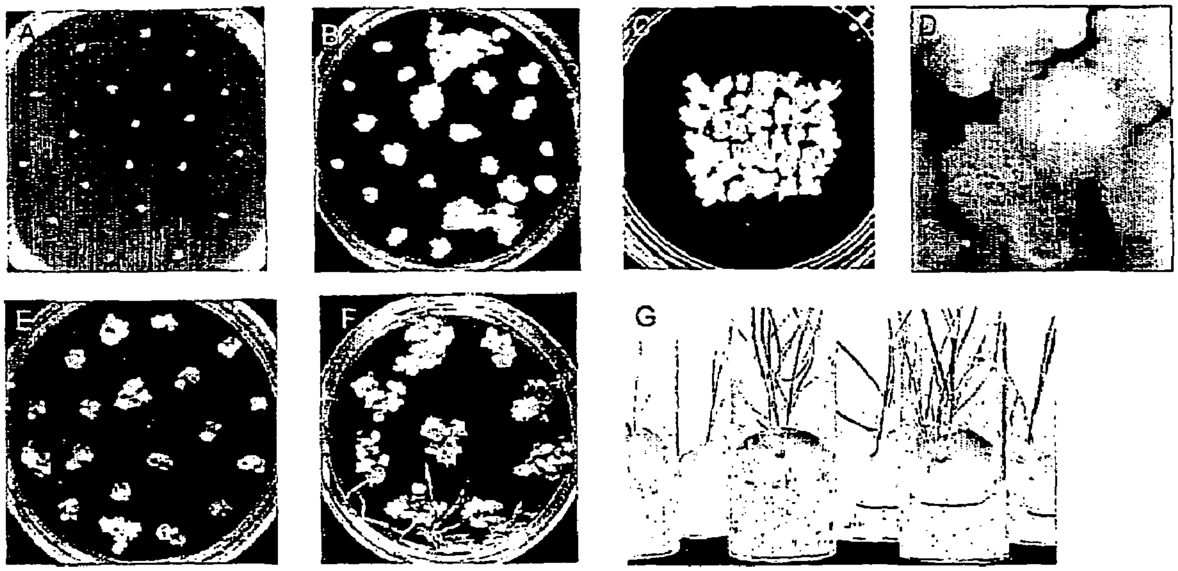

FIG. 19 shows the protocol for suspension culture-independent production of transgenic perennial ryegrass plants. A) Isolated zygotic embryos, plated on MSM5 medium, day 0; B) Embryogenic callus formation and proliferation, 6-8 weeks after embryo isolation; C) Embryogenic calli arranged on high osmotic MSM3Plus medium prior to biolistic transformation; D) Histochemical GUS assay showing GUS-expressing foci 3-4 days post-bombardment of chimeric gusA gene; E) Selection of embryogenic calli on MSM3 medium containing 100 mg/l paromomycin (Pm), 2 weeks after microprojectile bombardment; F) Regeneration of Pm resistant shoots on MSK medium containing 100 mg/l Pm, 4 weeks after microprojectile bombardment; G) In vitro plant regeneration from PM resistant embryogenic calli, 6 weeks after microprojectile bombardment; H) Transgenic perennial ryegrass plants 28 weeks after embryo isolation.

Figure 20:
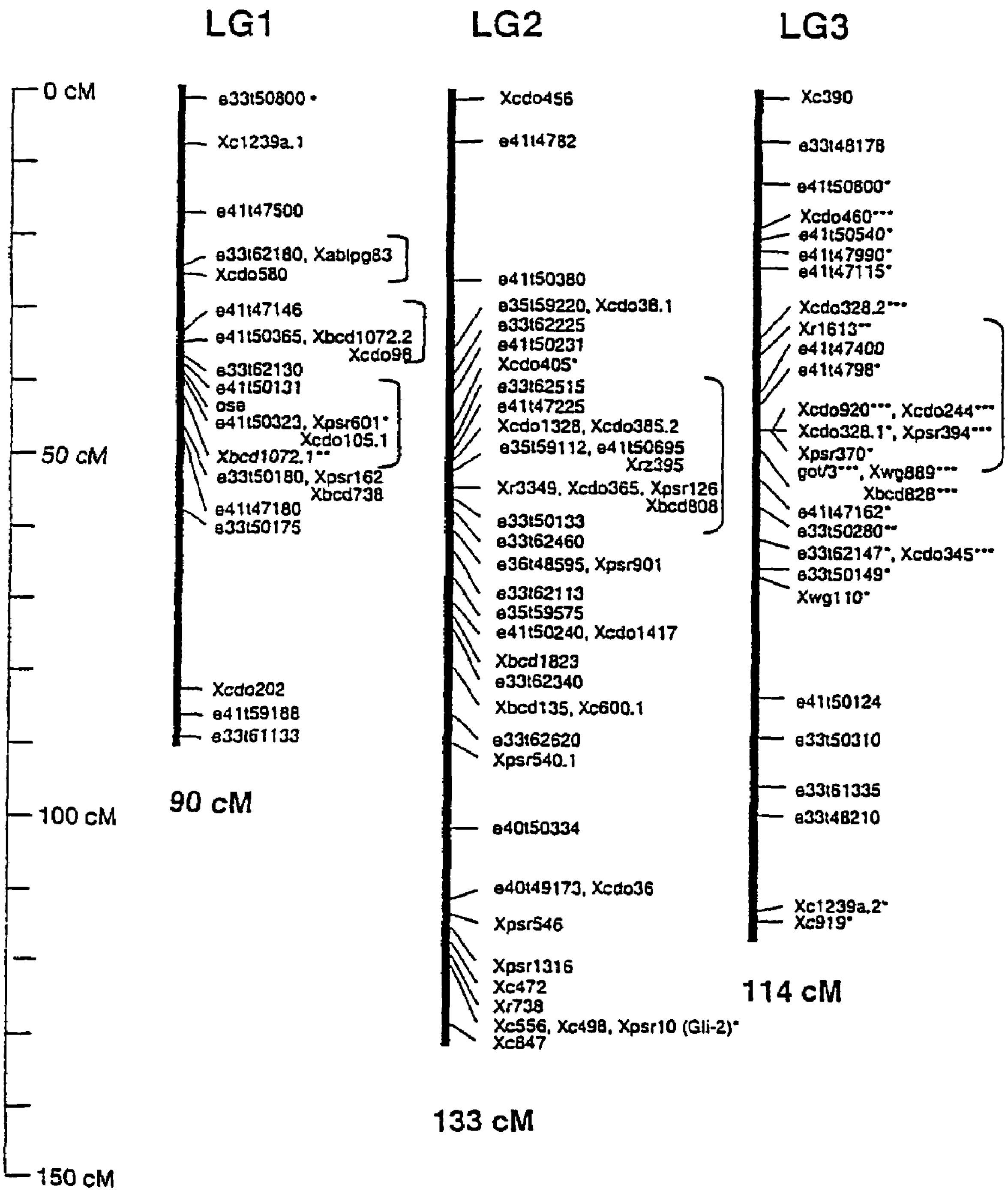
Figure 20:
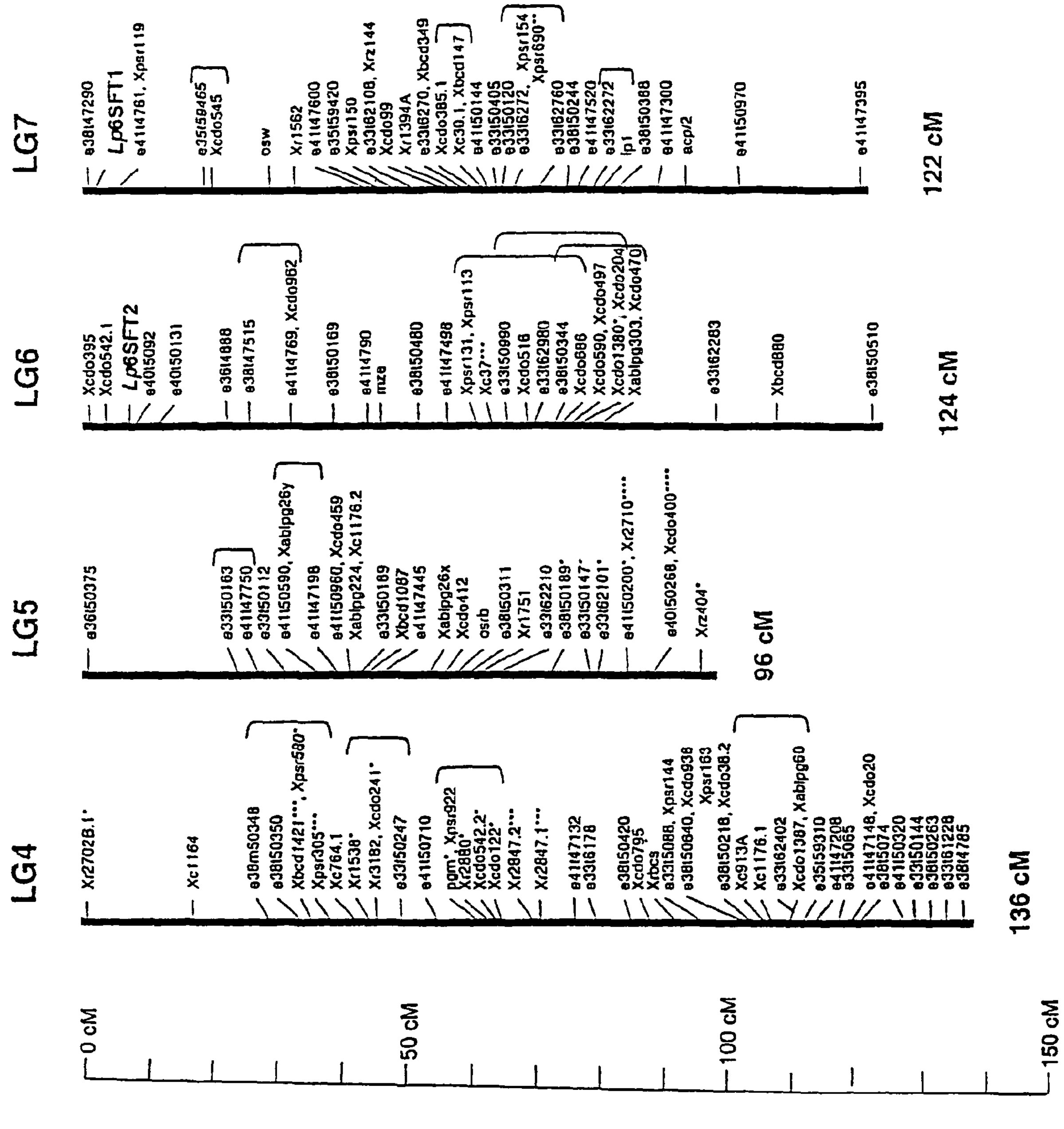

FIG. 20 shows the map location of Lp6SFT1 and Lp6SFT2 (in bold) within the genetic linkage map of perennial ryegrass.

EXAMPLE 1

The Isolation of cDNA Clones Encoding for Fructan Biosynthetic Enzymes from Perennial Ryegrass A cDNA library prepared from RNA extracted from perennial ryegrass seedlings was used to isolate fructosyltransferase homologues Lp6SFT1 and Lp6SFT2. These cDNA clones were isolated from the perennial ryegrass cDNA library using the barley 6SFT gene as a probe. The complete gene sequences of the isolated perennial ryegrass fructosyltransferase homologues are shown in FIGS. 1 and 2.

More particularly, a perennial ryegrass seedling cDNA library was screened with a 1,200 bp PstI fragment isolated from a barley 6-SFT cDNA clone. Twelve cDNAs were isolated and separated into four groups by restriction digest analysis. Two full length clones Lp6SFT1 and Lp6SFT2 were selected for further characterisation.

The complete sequence of clone Lp6SFT1 was determined. The cDNA clone had a typical poly(A) tail, start and stop codon. The open reading frame (ORF) of the clone encoded for a putative protein of 651 amino acids.

The complete sequence of the second *L. perenne* 6SFT cDNA homologue (Lp6SFT2) was determined. The full length cDNA clone had a typical poly(A) tail, start and stop codon and the 2013 bp ORF coded for a protein of 671 amino acids.

A northern hybridization analysis with RNA samples isolated from perennial ryegrass at different developmental stages hybridised to Lp6SFT1 (FIG. 3, upper blot) and Lp6FST2 (FIG. 3, lower blot) was performed to determine patterns of organ and developmental expression. Both probes hybridised to a single mRNA species of approximately 2.3 kb and 2.4 kb respectively. The Lp6SFT1 and Lp6SFT2 transcript was found to accumulate in young shoots and roots and mature stem tissue (FIG. 3).

A Southern hybridisation analysis using DNA, isolated from a perennial ryegrass double haploid plant, digested with DraI, BamHI, EcoRI, EcoRV, HindIII and XbaI was hybridised at high stringency with an Lp6SFT1 and Lp6SFT2 probe respectively. The hybridisation pattern revealed that both Lp6SFT1 (FIG. 4, left blot) and Lp6SFT2 (FIG. 4, right blot) correspond to a single copy gene in perennial ryegrass (FIG. 4).

EXAMPLE 2

Functional Analysis of Ryegrass Fructosyltransferases

The functionality of the ryegrass fructosyltransferase cDNA homologues Lp6SFT1 and Lp6SFT2 have been determined by expression in the yeast strain *Pichia pastoris*. The enzyme activity of the secreted Lp6SFT1 and Lp6SFT2 recombinant proteins were both found to have fructosyltransferase activity when incubated with sucrose and the trisaccharide 1-kestose. These functional data demonstrate Lp6SFT1 and Lp6SFT2 are fructosyltransferases suitable for manipulating fructan pools in transgenic ryegrass.

To determine the functionality of the ryegrass fructosyltransferase cDNA homologues the cDNAs encoding Lp6SFT1, Lp6SFT2 and the control barley Hv6SFT minus the 5' targeting signal sequence have been cloned into the yeast transformation secrectory plasmid pPICZαC (vectors available for the production of recombinant protein) (FIG. 5). The yeast strain *Pichia pastoris* has been transformed with the above plasmids and the corresponding empty parent vector as a control. The enzyme activity of the secreted Lp6SFT1, Lp6SFT2 and Hv6SFT recombinant protein was analysed for fructosyltransferase activity by incubating with sucrose and the trisaccharide 1-kestose.

*Pichia pastoris* transformed with Lp6SFT1 produced and secreted a functional protein that had fructosyltransferase activity, similar to the activity of the recombinant HV6SFT protein. Both produced a DP4 fructan and small amounts of higher DP fructans with were absent in the control vector (FIG. 6).

*Pichia pastoris* transformed with Lp6SFT2 produced and secreted a functional protein that had both fructosyltransferase and some invertase activity. The activity of Lp6SFT2 recombinant protein in the presence of sucrose and 1-kestose produced DP4 and greater fructans, which were absent in the control vector when incubated under the same conditions (FIG. 7).

EXAMPLE 3

Partial cDNA clones were isolated as previously described for Lp6SFT1 and Lp6SFT2 using the Barley 6SFT (Hv6SFT) as a probe. These partial fructosyltransferases (4Ad and 6Cb; see FIGS. 8 and 9, respectively) have high amino acid homology to both Lp6SFT1 and Lp6SFT2 (see table below). They have been used to isolate additional fructosyltransferases such as the genomic clones Lp6SFT3 and Lp6SFT4. The high homology of these partial nucleotide sequences to other fructosyltransferases makes them excellent candidates for the isolation of additional cDNA and genomic clones encoding fructosyltransferases in plants.

TABLE

% Amino acid homology of partial ryegrass fructosyltransferases to Lp6SFT1 and Lp6SFT2.

| | 4Ad | 6Cb |
|---|---|---|
| Lp6SFT1 | 69% | 70% |
| Lp6SFT2 | 64% | 64% |

EXAMPLE 4

The Isolation and Characterisation of Fructosyltransferase Genomic Clones and Promoters Genomic clones and promoters of Lp6FST1 and Lp6SFT3 have been isolated from a perennial ryegrass genomic library. Both clones have been fully sequenced (FIGS. 10 and 11).

More particularly, a *Lolium perenne* genomic library was screened with a partial cDNA fragment designated Lp6SFT3. A 4819 bp genomic fragment was isolated, cloned into pBluescript and fully sequenced. The 4.8 kb fragment was found to contain the entire Lp6SFT3 gene and 1.6 kb of promoter sequence. The Lp6SFT3 genomic sequence including exon-intron organisation is illustrated in FIG. 11.

EXAMPLE 5

Analysis of Expression Patterns from Ryegrass Fructosyltransferase Promoters

Genomic clones and promoters of Lp6FST1 and Lp6SFT3 have been isolated from a perennial ryegrass genomic library. Both clones have been fully sequenced. Promoters have been fused to the gusA (FIG. 12) reporter gene and introduced into tobacco by direct gene transfer for in planta expression pattern analysis. Plant material was histochemically assayed for β-glucuronidase (GUS) activity to determine patterns of expression from the Lp6SFT1 promoter in the heterologous system, tobacco. Weak GUS activity was detected in the leaf base and in leaf vascular tissue (FIG. 13).

This example demonstrates the use of ryegrass fructosyltransferase promoter sequences for targeted gene expression in plants.

EXAMPLE 6

Isolation of Genomic Clone for the Ryegrass Fructosyltransferase Lp6SFT4

Lp6SFT4 was isolated from a perennial ryegrass genomic library using the fructosyltransferase partial clone 4Ad (from FIG. 8) as a hybridisation probe. The genomic clone Lp6SFT4 contains 966 bp of promoter sequence and the entire gene coding sequence. The Lp6SFT4 genomic sequence including exon-intron organisation is illustrated in FIG. 14.

EXAMPLE 7

Development of Sense and Antisense Vectors with Fructosyltransferase Sequences

To determine the functionality of the Lp6SFT1 and Lp6SFT2 fructosyltransferase homologues and to regulate the expression of these key enzymes in the biosynthesis of fructans in *L. perenne* a set of sense and antisense vectors have been generated. Transformation vectors with Lp6SFT1 and Lp6SFT2 cDNA sequences in sense and antisense orientation under the control of either the CaMV 35S and maize ubiquitin promoter have been generated (FIG. 15).

EXAMPLE 8

Production and Characterisation of Transgenic Tobacco Plants Expressing the Ryegrass Fructosyltransferase Lp6SFT1 Gene Transformation experiments, using vectors carrying the chimeric ryegrass fructosyltransferase genes Lp6SFT1 in sense and antisense orientation under the control of the CaMV 35S promoter, have been performed in tobacco, a fructan-devoid plant, to assess the functionality of Lp6SFT1.

A set of transgenic tobacco plants generated using the Lp6SFT1 sense transformation vector were screened by PCR and analysed by Southern and northern hybridizations (FIGS. 16A, B, C, D, E).

PCR screening was undertaken using npt2 and Lp6SFT1 specific primers for the identification of the transgenic plants (FIG. 16B). Independent transgenic plants were identified which were cotransformed with both the selectable marker (neomycinphosphotransferase npt2) and the ryegrass fructosyltransferase Lp6SFT1 gene.

Southern hybridization analysis was performed with DNA samples from the PCR positive transgenic plants in order to demonstrate the integration of the Lp6SFT1 transgene. Genomic DNA was digested with EcoRI and analysed by Southern hybridization analysis (FIG. 16C, D). Hybridization to a band of the expected size (transgene plus promoter and terminator) was observed in transformed plants. Additional larger and smaller bands corresponding to multiply rearranged transgene copies were also found in individual transgenic plants (FIG. 16C, D). No hybridizing bands were detected in the untransformed tobacco negative control (SR1).

Northern hybridization analysis of total RNA isolated from Southern positive Lp6SFT1 transgenic tobacco plants and probed with an Lp6SFT1 specific fragment revealed that the transgene was expressed in 1 out of the 5 Lp6SFT1 transgenic plants tested (FIG. 16E).

EXAMPLE 9

Production and Characterisation of Transgenic Tobacco Plants Expressing the Ryegrass Fructosyltransferase Lp6SFT2 Gene Transformation experiments, using vectors carrying the chimeric ryegrass fructosyltransferase genes Lp6SFT2 in sense and antisense orientation under the control of the CaMV 35S promoter, have been performed in tobacco, a fructan-devoid plant, to assess the functionality of Lp6SFT2.

A set of transgenic tobacco plants generated using the Lp6SFT2 sense transformation vector were screened by PCR and analysed by Southern and northern hybridizations (FIG. 17A, B, C, D).

PCR screening was undertaken using npt2 and Lp6SFT2 specific primers for the identification of the transgenic plants (FIG. 17A). Independent transgenic plants were identified which were cotransformed with both the selectable marker (neomycinphosphotransferase npt2) and the ryegrass fructosyltransferase Lp6SFT2 gene (FIG. 17B).

Southern hybridization analysis was performed with DNA samples from the PCR positive transgenic plants in order to demonstrate the integration of the Lp6SFT2 transgene. Genomic DNA was digested with EcoRI and analysed by Southern hybridization analysis (FIG. 17C). Hybridization to a band of the expected size (transgene plus promoter and terminator) was observed in transformed plants. Additional larger and smaller bands corresponding to multiply rearranged transgene copies were also found in individual transgenic plants (FIG. 17D). No hybridizing bands were detected in the untransformed tobacco negative control (SR1).

Northern hybridization analysis of total RNA isolated from Southern positive Lp6SFT2 transgenic plants and probed with an Lp6SFT2 specific gene fragment revealed that the Lp6SFT2 transgene was expressed in all 4 Lp6SFT2 transgenic plants tested (FIG. 17D).

Progenies (T1 plants) from the primary transgenic tobacco plants expressing the chimeric Lp6SFT2 gene were obtained. Callus generated from these T1 plants was screened by northern hybridization analysis (FIG. 18A). Callus was grown on MS morpho medium in the dark for 1 month. Soluble carbohydrates were isolated from transgenic plants and antisense negative controls and sugar products analysed by high performance anion exchange chromatography (HPAEC) (FIG. 18Bi and 18Bii). Kestose or DP 3 fructan was detected and identified in the Lp6SFT2 callus (FIG. 18Bi) and was absent in the negative control samples (FIG. 18Bii), demonstrating fructosyltransferase activity in the callus samples from Lp6SFT2-expressing transgenic tobacco plants under these conditions.

This example demonstrates the use of ryegrass fructosyltransferase gene sequences for expression in plants leading to manipulated fructan accumulation.

EXAMPLE 10

Production of Transgenic Ryegrass Plants for Transgenic Expression of Fructosyltransferases To investigate the effects of over-expression and down-regulation of fructosyltransferases in perennial ryegrass through sense and antisense technology, transformation vectors carrying chimeric fructosyltransferase genes in sense and antisense orientation were used for the biolistic transformation of embryogenic calli derived from mature seed-embryos. A robust and reliable procedure for the recovery of transgenic perennial ryegrass plants was used.

The procedure utilises embryogenic calli produced from mature seed-derived embryos as direct targets for biolistic transformation without requiring the establishment of embryogenic cell suspensions. The protocol, however, relies on a continuous supply of isolated zygotic embryos for callus induction. Transgenic ryegrass plants are regenerated 24-28 weeks after embryo isolation. Isolated embryos are plated onto MSM5 medium to produce embryogenic calli suitable as targets for biolistic transformation within 8 weeks. The embryogenic calli treated on high-osmoticum medium MSM3Plus prior to microprojectile bombardment, are selected on MSM3 medium containing 100 mg/l paromomycin (Pm) for 2 weeks before being transferred onto MSK with 100 mg/l Pm for further 4 weeks until differentiation of Pm resistant shoot (FIG. 19). A set of transgenic plants for over-expression and down-regulation of fructosyltransferases using sense and antisense Lp6SFT1 and Lp6SFT2 chimeric genes was generated.

EXAMPLE 11

Genetic Mapping of Ryegrass Fructosyltransferases

Lp6SFT1 and Lp6SFT2 clones were PCR amplified and radio-labelled for use as probes to detect restriction fragment length polymorphisms (RFLPs). RFLPs were mapped using 110 progeny individuals of the p150/112 perennial ryegrass reference population restricted with the enzyme HindIII. Lp6SFT1 and Lp6SFT2 loci mapped to linkage groups LG7 and LG6, respectively (FIG. 20). These gene locations can now be used as candidate genes for quantitative trait loci for fructan biosynthesis associated traits such as herbage quality, drought and cold tolerance and plant growth components.

Finally, it is to be understood that various alterations, modifications and/or additions may be made without departing from the spirit of the present invention as outlined herein.

It will also be understood that the term "comprises" (or its grammatical variants) as used in this specification is equivalent to the term "includes" and should not be taken as excluding the presence of other elements or features.

Documents cited in this specification are for reference purposes only and their inclusion is not an acknowledgement that they form part of the common general knowledge in the relevant art.

The invention claimed is:

1. A substantially purified or isolated nucleic acid encoding a sucrose:sucrose 1-fructosyltransferase (1-SST) homologue, said nucleic acid comprising the nucleotide sequence of SEQ ID No: 11, or a variant of Seq. ID No. 11 with one or more nucleotide changes that result in conservative amino acid substitutions, with the proviso that the variant of Seq. ID No. 11 has at least 95% sequence identity with Seq ID No. 11.

2. A substantially purified or isolated nucleic acid that is the complement of a nucleic acid encoding a sucrose:sucrose 1-fructosyltransferase (1-SST) homologue comprising SEQ. ID No. 11, or a variant of Seq. ID No. 11 with one or more nucleotide changes that result in conservative amino acid substitutions, with the proviso that the variant of Seq. ID No. 11 has at least 95% sequence identity with Seq. ID No. 11.

3. A substantially purified or isolated nucleic acid encoding a sucrose:sucrose 1-fructosyltransferase (1-SST) homologue, said nucleic acid comprising a nucleotide sequence that is the complement of the coding portions of SEQ ID No: 11 as depicted in FIG. 11 hereto, or a variant of said coding portions with one or more nucleotide changes that result in conservative amino acid substitutions, with the proviso that the variant of Seq. ID No. 11 has at least 95% sequence identity with the coding portions of Seq ID No. 11.

4. A substantially purified or isolated nucleic acid encoding a sucrose:sucrose 1-fructosyltransferase (1-SST) homologue, said nucleic acid comprising the coding portions of SEQ ID No. 11 as depicted in FIG. 11 hereto, or a variant of said coding portions with one or more nucleotide changes that result in conservative amino acid substitutions, with the proviso that the variant of Seq. ID No. 11 has at least 95% sequence identity with the coding portions of Seq ID No. 11.

5. The nucleic acid of claim 4, wherein the nucleic acid comprises the coding portions of SEQ ID No. 11 as depicted in FIG. 11 hereto.

6. The nucleic acid of claim 1, wherein the nucleic acid comprises SEQ ID No. 11.

7. A substantially purified or isolated nucleic acid encoding a sucrose:sucrose 1-fructosyltransferase (1-SST) homologue, said 1-SST homologue comprising the amino acid sequence of SEQ ID No: 12 or a variant of the amino acid sequence of SEQ ID No: 12 with one or more conservative amino acid substitutions, with the proviso that the encoded variant of Seq. ID No. 12 has at least 95% sequence identity with Seq ID No. 12.

8. The nucleic acid of claim 7, wherein the nucleic acid comprises a sequence encoding the amino acid sequence of SEQ ID No: 12.

9. A vector comprising a nucleic acid according to claim 1, wherein the nucleic acid comprises the nucleotide sequence of SEQ ID No: 11.

10. The vector according to claim 9 further comprising a promoter and a terminator, said promoter, nucleic acid and terminator being operatively linked.

11. A vector comprising a nucleic acid according to claim 1.

12. The vector according to claim 11 further comprising a promoter and a terminator, said promoter, nucleic acid and terminator being operatively linked.

13. A plant cell, plant, plant seed or other plant part comprising the vector according to claim 11.

14. A plant cell, plant, plant seed or other plant part comprising the vector according to claim 10.

15. A method of modifying fructan biosynthesis in a plant, said method comprising introducing into said plant an effective amount of the nucleic acid according to claim 1.

16. A method of modifying fructan biosynthesis in a plant, said method comprising introducing into said plant an effective amount of the nucleic acid according to claim 4.

17. A method of modifying fructan biosynthesis in a plant, said method comprising introducing into said plant an effective amount of a vector according to claim 11.

* * * * *

SEQUENCE LISTING

<160> NUMBER OF SEQ ID NOS: 14

<210> SEQ ID NO 1
<211> LENGTH: 2386
<212> TYPE: DNA
<213> ORGANISM: Lolium perenne

<400> SEQUENCE: 1
ggcacgagat ctgctccatt tgttttggaa ttcgccgacg atcgatggag tctcggtcca 60
ttcccggcgc gtacgcgtac gagccgctgc cccactcctc cgacgacgcc catggccacg 120
acgaccgccg gagcgccggc ggcgtgaggt ggcgcgcgtg cgcggccgtt cttgcggcgt 180
ctgccctggt tgtgttcgtg gtcgccagca cgctcgccgg gtcaagggtg gaccgcgtgg 240
ccgtggacgt ggctgccatg ccggcgctgt cggagacggc gaggagccgt gggaaggacg 300
cgggcgtgtc ggagaagacg tccggcgcgg cggacgagat ggggttcctc ggcgccggct 360
ccggcgccga cgccgacggg ttcccgtgga gcaacgccat gctgcagtgg cagcgcacgg 420
gtttccattt ccagcccgag atgaactgga tgaacgatcc caacggtccg gtgtattacc 480
gaggatggta ccacctcttc taccagtaca accccgaggg ggcggtgtgg ggcaacatcg 540
cgtggggcca cgccgtgtcc cgggacctgg tccactggcg ccacctcccg ctcgccatgg 600
tgcctgacca atggtacgac atcaacggtg tctggacggg ctccgccact gtgttccccg 660
atgggaccct caacatgctc tacacggggt ccaccaacgc ctccgtgcag gttcagtgcc 720
ttgctgtgcc cgaggacccc aacgactccc tcctccgcaa ctggacaaag cacgaagcta 780
accccgtgct cctaccgccg cccgggatcg gcgacaagga cttccgtgac ccgaccaccg 840
cctggttcga cgagtccgac cagacgtggc gcaccgtcat cgggtccaag gacaacaacg 900
gccacgccgg tattgccatg gtgtacaaga ccaaggactt cctcaactac gagctcatcc 960
cgggatactt gcatcgcgtc gacggcaccg gcatgtggga gtgcatcgac ttctaccccg 1020
tcggaggcaa aaacggcagc gaggagttgt acgtgatcaa ggagagcagc gacgacgacc 1080
gacatgactg gtacacgcta gggaaatacg acgcggcagc caacacgttc acggccgcgg 1140
acccggagaa cgacctaggg attgggttga ggtatgactg gggcaagttc tacgcgacca 1200
agactttcta cgacccggcc aagaatcggc gcgtgctctg ggatggatc ggcgagaccg 1260 actctgagcg cgccgatgtc gccaagggat gggcatccct catgtcgatt ccgaggacgg 1320
tggaactcga cgagaagacc cggaccaacc tcatccaatg gccggtggag gagctcgaga 1380
ccctccgcat caagtccacc gacctcggtg gcgtcaccat cgaccacggc agcgtctacc 1440

-continued

```
cactccctct ccaccgcgcc acacaactcg acattgaggc ctccttccgc atcgacactg   1500

ccaccgtcgc tgccctcaat gaggctgacg ttggctacaa ttgcagcacc agcggtggct   1560

ctgccaaccg tggcgcactc ggcccctttg gcctcctcgt cctcgccgac ggtaaggcag   1620

agcagacggc agtgtacttc tatgtggcca agggcctcga cgggaccctc caaacccact   1680

tctgccacga cgagtcacgg tcgacgcttg ctagggatgt tgtgaagcgg gtggtgggat   1740

acaccgtgcc tgtcctcgac ggtgaggcct tctccgtcag ggtgctcgtg gaccactcaa   1800

tcgtggagag cttcgccatg ggcggcaggt ccacggcaac atcgagggtg tacccaacgg   1860

aggccatcta tggcgctgcc ggtgcgtatc ttttcaacaa cgccaccggc ggctccgtca   1920

ccgttgagaa gctcgtggtg catgagatgg actcgtccta caaccagatc ttcatggctg   1980

acgacttgta gtcatcgtcg tccatggata gcgcgcgcgg atggtgagga tgatcaccta   2040

ctacatatac atacatacta ttgatcgagc gatcaccaca tcggtcggtg gcggcttcct   2100

cttctcttgg atgcagaagg agatggagta ctagctactc tatttaccat gttgttttgt   2160

tggttttttt gggttttggg tttttgacga gatggatgaa ttagctatag atggacgatt   2220

gtgtcctatt tatctcctgc cttccgagtg taactataca tatattggca ggatcgatga   2280

tatccctact gcatgacagt catgattaat tattgtgatg atattgatca atcaacttgt   2340

aaatgaattt attgggggaa aggtttatga aaaaaaaaaa aaaaaa                  2386


<210> SEQ ID NO 2
<211> LENGTH: 648
<212> TYPE: PRT
<213> ORGANISM: Lolium perenne

<400> SEQUENCE: 2

Met Glu Ser Arg Ser Ile Pro Gly Ala Tyr Ala Tyr Glu Pro Leu Pro
1               5                   10                  15

His Ser Ser Asp Asp Ala His Gly His Asp Asp Arg Arg Ser Ala Gly
            20                  25                  30

Gly Val Arg Trp Arg Ala Cys Ala Ala Val Leu Ala Ala Ser Ala Leu
        35                  40                  45

Val Val Phe Val Val Ala Ser Thr Leu Ala Gly Ser Arg Val Asp Arg
    50                  55                  60

Val Ala Val Asp Val Ala Ala Met Pro Ala Leu Ser Glu Thr Ala Arg
65                  70                  75                  80

Ser Arg Gly Lys Asp Ala Gly Val Ser Glu Lys Thr Ser Gly Ala Ala
                85                  90                  95

Asp Glu Met Gly Phe Leu Gly Ala Gly Ser Gly Ala Asp Ala Asp Gly
            100                 105                 110

Phe Pro Trp Ser Asn Ala Met Leu Gln Trp Gln Arg Thr Gly Phe His
        115                 120                 125

Phe Gln Pro Glu Met Asn Trp Met Asn Asp Pro Asn Gly Pro Val Tyr
    130                 135                 140

Tyr Arg Gly Trp Tyr His Leu Phe Tyr Gln Tyr Asn Pro Glu Gly Ala
145                 150                 155                 160

Val Trp Gly Asn Ile Ala Trp Gly His Ala Val Ser Arg Asp Leu Val
                165                 170                 175

His Trp Arg His Leu Pro Leu Ala Met Val Pro Asp Gln Trp Tyr Asp
            180                 185                 190

Ile Asn Gly Val Trp Thr Gly Ser Ala Thr Val Phe Pro Asp Gly Thr
        195                 200                 205
```

-continued

```
Leu Asn Met Leu Tyr Thr Gly Ser Thr Asn Ala Ser Val Gln Val Gln
    210                 215                 220

Cys Leu Ala Val Pro Glu Asp Pro Asn Asp Ser Leu Leu Arg Asn Trp
225                 230                 235                 240

Thr Lys His Glu Ala Asn Pro Val Leu Leu Pro Pro Pro Gly Ile Gly
                245                 250                 255

Asp Lys Asp Phe Arg Asp Pro Thr Thr Ala Trp Phe Asp Glu Ser Asp
            260                 265                 270

Gln Thr Trp Arg Thr Val Ile Gly Ser Lys Asp Asn Asn Gly His Ala
        275                 280                 285

Gly Ile Ala Met Val Tyr Lys Thr Lys Asp Phe Leu Asn Tyr Glu Leu
    290                 295                 300

Ile Pro Gly Tyr Leu His Arg Val Asp Gly Thr Gly Met Trp Glu Cys
305                 310                 315                 320

Ile Asp Phe Tyr Pro Val Gly Gly Lys Asn Gly Ser Glu Glu Leu Tyr
                325                 330                 335

Val Ile Lys Glu Ser Ser Asp Asp Asp Arg His Asp Trp Tyr Thr Leu
            340                 345                 350

Gly Lys Tyr Asp Ala Ala Ala Asn Thr Phe Thr Ala Ala Asp Pro Glu
        355                 360                 365

Asn Asp Leu Gly Ile Gly Leu Arg Tyr Asp Trp Gly Lys Phe Tyr Ala
    370                 375                 380

Thr Lys Thr Phe Tyr Asp Pro Ala Lys Asn Arg Arg Val Leu Trp Gly
385                 390                 395                 400

Trp Ile Gly Glu Thr Asp Ser Glu Arg Ala Asp Val Ala Lys Gly Trp
                405                 410                 415

Ala Ser Leu Met Ser Ile Pro Arg Thr Val Glu Leu Asp Glu Lys Thr
            420                 425                 430

Arg Thr Asn Leu Ile Gln Trp Pro Val Glu Glu Leu Glu Thr Leu Arg
        435                 440                 445

Ile Lys Ser Thr Asp Leu Gly Gly Val Thr Ile Asp His Gly Ser Val
    450                 455                 460

Tyr Pro Leu Pro Leu His Arg Ala Thr Gln Leu Asp Ile Glu Ala Ser
465                 470                 475                 480

Phe Arg Ile Asp Thr Ala Thr Val Ala Ala Leu Asn Glu Ala Asp Val
                485                 490                 495

Gly Tyr Asn Cys Ser Thr Ser Gly Gly Ser Ala Asn Arg Gly Ala Leu
            500                 505                 510

Gly Pro Phe Gly Leu Leu Val Leu Ala Asp Gly Lys Ala Glu Gln Thr
        515                 520                 525

Ala Val Tyr Phe Tyr Val Ala Lys Gly Leu Asp Gly Thr Leu Gln Thr
    530                 535                 540

His Phe Cys His Asp Glu Ser Arg Ser Thr Leu Ala Arg Asp Val Val
545                 550                 555                 560

Lys Arg Val Val Gly Tyr Thr Val Pro Val Leu Asp Gly Glu Ala Phe
                565                 570                 575

Ser Val Arg Val Leu Val Asp His Ser Ile Val Glu Ser Phe Ala Met
            580                 585                 590

Gly Gly Arg Ser Thr Ala Thr Ser Arg Val Tyr Pro Thr Glu Ala Ile
        595                 600                 605

Tyr Gly Ala Ala Gly Ala Tyr Leu Phe Asn Asn Ala Thr Gly Gly Ser
    610                 615                 620

Val Thr Val Glu Lys Leu Val Val His Glu Met Asp Ser Ser Tyr Asn
```

-continued 625 630 635 640

Gln Ile Phe Met Ala Asp Asp Leu
645

<210> SEQ ID NO 3
<211> LENGTH: 2340
<212> TYPE: DNA
<213> ORGANISM: Lolium perenne

<400> SEQUENCE: 3
ggcacgagct tgtctaatcc ctccctcgca ctagtcggcc gaggcattct tcctagttgc 60
ttccatcgca tcgatctcga tccacagatt ctatgccaat ggaggcaaga gatggcgtct 120
cgatgcccta ctcgtatgcg gccctgccgg aggacgccga ggcagcggtg gttgggcgcg 180
gtcgccggac cgggcctctg ttcgcagcgt tgctgttgac gttggtcgcc gcgctccttg 240
ccgtcgccgc gctggctggc gtcaggctcg ttggcgagct gcctgccggg ggcgtcktca 300
tgcccaacca cccgatggaa gtcatggacg tcagcggtag cagagggcct gagtcaggcg 360
tgtcggagaa gacgtccggg gccgccagcg agagcggcgg catgctgggc gccgacgccg 420
gcagcaacgc gttcccgtgg agcaatgcga tgctccagtg gcagcgcacc ggcttccact 480
tccagcccga gaagaactgg atgaacgacc ccaacggtcc ggtctactac aaggggtggt 540
accacctctt ctaccagtac aacccggagg gcgcaatctg ggcaacaag atcgcgtggg 600 gccatgccgt gtcccgggac atgctccggt ggcgccacct gcccatcgcc atgttccccg 660
accagtggta cgacatcaac ggcgcatggt caggctccgc caccgtgctc cccgacggcc 720
gcatcgtcat gctctacacg ggctccacca acgcctccgt gcaggtccag tgcctcgcct 780
tcccctccga cccctccgac ccgctgctca ccaactggac caagtatgag ggcaacccgg 840
tgctgtaccc gcctccgcac gtcggggaga aggacttccg ggacccgacc actgcatggt 900
acgatggctc cgatggaatg tggcggatcg tcatcgggtc caaggataac cgccgcgccg 960
gcatggcctt gacctacaag accaagaact tccatgattt tgagctcgtt cccggagtgc 1020
tgcaccgggt gccggcgacg gggatgtggg agtgcatcga tttgtacccg gttggcggcg 1080
cgaggggcat tgacatgacg gaggccgttg cggcggcatc caacagcggt ggtggtgaag 1140
ttttgcatgt catgaaggag agctcagacg acgaccgaca tgactactac gcgctaggga 1200
ggtacgatgc agcgacaaac aagtggacac cgctagatgc cgacgccgat gtcggcatcg 1260
ggctgaggta cgattgggga aagttctacg catccaagac cttctatgac ccggccaaga 1320
agaggcgtgt gctatggggg tgggtcggcg agactgactc tgagcgcgcc gacgtggcca 1380
agggatgggc ttccctacag tcgatccctc gcacggtrgt gctagatacc aagacgggca 1440
gcawccttat ccagtggccg gtggtcgagg tggagacgct ccgtaccaac tccaccaatc 1500
tcgggagcat catcgtcgag catggctccg tcttccctct cagtctccac cgggccacac 1560
agctcgacat cgaggcttcc ttccgcctgg acccgctcga tgtcgccgcc gcaaaggagg 1620
ccgacgttgg ctacaactgc agcaccagcg gtggcgcggc cggtcgtgga gcgctcggtc 1680
cctttggcct gctcgtactc gccgatgcca ggcgccatgg cggggacacg gagcagaccg 1740
ccgtctactt ctacgtcgcg aggggcctcg atggcaacct gcgcacgcac ttctgccatg 1800
acgagtcacg gtcatcccgt gccaacgaca ttgtcaagag ggtcgttggc aacatcgtgc 1860
cagtgctcga cggagaggcg ctgtctgtta gggttctggt ggaccamtcc attgtcgaga 1920
gyttcgcaca gggtgggagg tcggtggtga mttcaacgga gtttaacccg actgaggcca 1980

-continued

```
tmtacgccaa tgccggggta tacctcttca acaacgccac cggtgcccgg gtcaccgcca   2040

ccagtctygt cgtccatgag atggacccct cctacaacca gaaccaggcc gagatggctt   2100

cattgtaaat cgaagatgta catattgttt tttgtgatag catgttgcac gtacaacatg   2160

tgtgctgaac atcgagggag cctggatcga gccaagggga atgtgcatcc ccgtaggcac   2220

cacccaaaac aaaacaaaaa tacgtgagcg aggcgaaacg caggccggaa tagactgcca   2280

caattagacc gggaaaagtg cccagagtgt tttgatgaat tcaaaaaaaa aaaaaaaaaa   2340
```

<210> SEQ ID NO 4
<211> LENGTH: 671
<212> TYPE: PRT
<213> ORGANISM: Lolium perenne
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (451)..(451)
<223> OTHER INFORMATION: Xaa can be any naturally occurring amino acid
<220> FEATURE:
<221> NAME/KEY: misc_feature
<222> LOCATION: (605)..(605)
<223> OTHER INFORMATION: Xaa can be any naturally occurring amino acid
<220> FEATURE:
<221> NAME/KEY: misc_feature
<222> LOCATION: (620)..(620)
<223> OTHER INFORMATION: Xaa can be any naturally occurring amino acid

<400> SEQUENCE: 4

```
Met Pro Met Glu Ala Arg Asp Gly Val Ser Met Pro Tyr Ser Tyr Ala
1               5                   10                  15

Ala Leu Pro Glu Asp Ala Glu Ala Ala Val Val Gly Arg Gly Arg Arg
            20                  25                  30

Thr Gly Pro Leu Phe Ala Ala Leu Leu Leu Thr Leu Val Ala Ala Leu
        35                  40                  45

Leu Ala Val Ala Ala Leu Ala Gly Val Arg Leu Val Gly Glu Leu Pro
    50                  55                  60

Ala Gly Gly Val Xaa Met Pro Asn His Pro Met Glu Val Met Asp Val
65                  70                  75                  80

Ser Gly Ser Arg Gly Pro Glu Ser Gly Val Ser Glu Lys Thr Ser Gly
                85                  90                  95

Ala Ala Ser Glu Ser Gly Gly Met Leu Gly Ala Asp Ala Gly Ser Asn
            100                 105                 110

Ala Phe Pro Trp Ser Asn Ala Met Leu Gln Trp Gln Arg Thr Gly Phe
        115                 120                 125

His Phe Gln Pro Glu Lys Asn Trp Met Asn Asp Pro Asn Gly Pro Val
    130                 135                 140

Tyr Tyr Lys Gly Trp Tyr His Leu Phe Tyr Gln Tyr Asn Pro Glu Gly
145                 150                 155                 160

Ala Ile Trp Gly Asn Lys Ile Ala Trp Gly His Ala Val Ser Arg Asp
                165                 170                 175

Met Leu Arg Trp Arg His Leu Pro Ile Ala Met Phe Pro Asp Gln Trp
            180                 185                 190

Tyr Asp Ile Asn Gly Ala Trp Ser Gly Ser Ala Thr Val Leu Pro Asp
        195                 200                 205

Gly Arg Ile Val Met Leu Tyr Thr Gly Ser Thr Asn Ala Ser Val Gln
    210                 215                 220

Val Gln Cys Leu Ala Phe Pro Ser Asp Pro Ser Asp Pro Leu Leu Thr
```

-continued

```
225                 230                 235                 240

Asn Trp Thr Lys Tyr Glu Gly Asn Pro Val Leu Tyr Pro Pro Pro His
                245                 250                 255

Val Gly Glu Lys Asp Phe Arg Asp Pro Thr Thr Ala Trp Tyr Asp Gly
            260                 265                 270

Ser Asp Gly Met Trp Arg Ile Val Ile Gly Ser Lys Asp Asn Arg Arg
        275                 280                 285

Ala Gly Met Ala Leu Thr Tyr Lys Thr Lys Asn Phe His Asp Phe Glu
    290                 295                 300

Leu Val Pro Gly Val Leu His Arg Val Pro Ala Thr Gly Met Trp Glu
305                 310                 315                 320

Cys Ile Asp Leu Tyr Pro Val Gly Gly Ala Arg Gly Ile Asp Met Thr
                325                 330                 335

Glu Ala Val Ala Ala Ala Ser Asn Ser Gly Gly Gly Glu Val Leu His
            340                 345                 350

Val Met Lys Glu Ser Ser Asp Asp Asp Arg His Asp Tyr Tyr Ala Leu
        355                 360                 365

Gly Arg Tyr Asp Ala Ala Thr Asn Lys Trp Thr Pro Leu Asp Ala Asp
    370                 375                 380

Ala Asp Val Gly Ile Gly Leu Arg Tyr Asp Trp Gly Lys Phe Tyr Ala
385                 390                 395                 400

Ser Lys Thr Phe Tyr Asp Pro Ala Lys Lys Arg Arg Val Leu Trp Gly
                405                 410                 415

Trp Val Gly Glu Thr Asp Ser Glu Arg Ala Asp Val Ala Lys Gly Trp
            420                 425                 430

Ala Ser Leu Gln Ser Ile Pro Arg Thr Val Val Leu Asp Thr Lys Thr
        435                 440                 445

Gly Ser Xaa Leu Ile Gln Trp Pro Val Val Glu Val Glu Thr Leu Arg
    450                 455                 460

Thr Asn Ser Thr Asn Leu Gly Ser Ile Ile Val Glu His Gly Ser Val
465                 470                 475                 480

Phe Pro Leu Ser Leu His Arg Ala Thr Gln Leu Asp Ile Glu Ala Ser
                485                 490                 495

Phe Arg Leu Asp Pro Leu Asp Val Ala Ala Ala Lys Glu Ala Asp Val
            500                 505                 510

Gly Tyr Asn Cys Ser Thr Ser Gly Gly Ala Ala Gly Arg Gly Ala Leu
        515                 520                 525

Gly Pro Phe Gly Leu Leu Val Leu Ala Asp Ala Arg Arg His Gly Gly
    530                 535                 540

Asp Thr Glu Gln Thr Ala Val Tyr Phe Tyr Val Ala Arg Gly Leu Asp
545                 550                 555                 560

Gly Asn Leu Arg Thr His Phe Cys His Asp Glu Ser Arg Ser Ser Arg
                565                 570                 575

Ala Asn Asp Ile Val Lys Arg Val Val Gly Asn Ile Val Pro Val Leu
            580                 585                 590

Asp Gly Glu Ala Leu Ser Val Arg Val Leu Val Asp Xaa Ser Ile Val
        595                 600                 605

Glu Ser Phe Ala Gln Gly Gly Arg Ser Val Val Xaa Ser Thr Glu Phe
    610                 615                 620

Asn Pro Thr Glu Ala Ile Tyr Ala Asn Ala Gly Val Tyr Leu Phe Asn
625                 630                 635                 640

Asn Ala Thr Gly Ala Arg Val Thr Ala Thr Ser Leu Val Val His Glu
                645                 650                 655
```

-continued

Met Asp Pro Ser Tyr Asn Gln Asn Gln Ala Glu Met Ala Ser Leu
660 665 670

<210> SEQ ID NO 5
<211> LENGTH: 1743
<212> TYPE: DNA
<213> ORGANISM: Lolium perenne

<400> SEQUENCE: 5
ggcacgagcg gacgagtgtc gggtaccatc acggtgctcc acaatggcac gctcgtcctc 60
ctctacacgg gggtcacaga agaccctatg gccgagtccc agtgcatcgc cgtcccgacc 120
gaccccaacg accccctcct tcgccattgg accaagcacc ccgccaaccc agttctcgct 180
cacccacagg gggtccaggg catggacttc cgagacccca ccagcgcgtg gtgggacaag 240
tccgactcca cgtggcgcat tctcatcggt tccaargacr amracaacgg cagccacgct 300
ggcwtcscct tcatcttcaa gaccaaggac ttccttagct tcgagcgtgt tccmagktat 360
cgttgcatcg tgttcsargg twccggcatg tkggagtgca tcgactttta ccccgttgga 420
ggtggccaca actcttcgtc ggaggagttg tacgtgataa aggcgagcat ggacgacgaa 480
cgacacgact actactcatt ggggaggtat gacgcggcag cgaacacatg gacgccattg 540
gacgccgagc tagacttggg gattgggctg aggtacgact ggggcaagct ctacgcttcc 600
acgtcgttct acgatccact gaagcagcgg cgaattatgt tggggtatgt aggcgaggtc 660
gactctgcgc gagccgacgt tgccaaggga tgggcctcac ttcagtcgat tccgaggaca 720
gtggcactag acgagaagac ccggacgaac ctcctcctat ggccggtgga ggaggtggag 780
gccctccgct acaactccac cgacctcagc ggcatcactg ttgagaacgg ctccatcttc 840
cacctccctc tccaccaagc cactcagctg gacatcgagg cttccttccg cctcgatgct 900
tctgatgttg ctgccatcaa cgaggccgac gtcggctaca actgcagcag cagcggtggc 960
gcggccgctc gtggcgctct cggccccttc ggcctcctcg tccatgccgc cggagacctc 1020
cgtggcgagc agacggcggt gtacttctac gtgtccaggg ccctcgacgg tagcctccgg 1080
accagcttct gcaacgacga gacgcggtcg tcacgggcca gggacgtgac gaagcgggtg 1140
gtgggcagca cggtgccggt gctcgacggc gaggtgttag cgatgagggt gctcgtggac 1200
cactcgatcg tgcagagctt cgcgatgggt gggagggtca cggcgacgtc gcgggtgtac 1260
ccaacggagg ctatctacgc cagggcaggg gtgtacctgt tcaacaacgc caccggcgcc 1320
agcgtgacgg cggagaggct catcgtgcac gagatggcct cggcggtata cgacgagacc 1380
gtcatggtta aggactcata gctgctcaca catgagctat cagaccggta acgttgggtc 1440
actagcattt tcaagcgttg aaataattta cttggcgtag caagccccgg gtccgaggtt 1500
ccaaaagtaa ggtgggatat tcttccaaac tccgcgagtc ccgcaaggtt gtctaggtgt 1560
gagtgtgatg tcgtttgcgc acctgcgcgt gtgcttgtaa tttgctggat ttgttgtttc 1620
tttacagaaa aaaaaggata ctatactatg taagtatcta cattgttgta tmwmwrrwrw 1680
awmwwaaraa aaaatatatg caagcatgca tgcacgttgt cgtaaaaaaa aaaaaaaaaa 1740
aaa 1743

<210> SEQ ID NO 6
<211> LENGTH: 466
<212> TYPE: PRT
<213> ORGANISM: Lolium perenne
<220> FEATURE:
<221> NAME/KEY: misc_feature -continued

```
<222> LOCATION: (94)..(94)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid

<400> SEQUENCE: 6

Gly Thr Ser Gly Arg Val Ser Gly Thr Ile Thr Val Leu His Asn Gly
1               5                   10                  15

Thr Leu Val Leu Leu Tyr Thr Gly Val Thr Glu Asp Pro Met Ala Glu
            20                  25                  30

Ser Gln Cys Ile Ala Val Pro Thr Asp Pro Asn Asp Pro Leu Leu Arg
        35                  40                  45

His Trp Thr Lys His Pro Ala Asn Pro Val Leu Ala His Pro Gln Gly
    50                  55                  60

Val Gln Gly Met Asp Phe Arg Asp Pro Thr Ser Ala Trp Trp Asp Lys
65                  70                  75                  80

Ser Asp Ser Thr Trp Arg Ile Leu Ile Gly Ser Lys Asp Xaa Asn Asn
                85                  90                  95

Gly Ser His Ala Gly Ile Ala Phe Ile Phe Lys Thr Lys Asp Phe Leu
            100                 105                 110

Ser Phe Glu Arg Val Pro Xaa Tyr Arg Cys Ile Val Phe Glx Gly Thr
        115                 120                 125

Gly Met Trp Glu Cys Ile Asp Phe Tyr Pro Val Gly Gly Gly His Asn
    130                 135                 140

Ser Ser Ser Glu Glu Leu Tyr Val Ile Lys Ala Ser Met Asp Asp Glu
145                 150                 155                 160

Arg His Asp Tyr Tyr Ser Leu Gly Arg Tyr Asp Ala Ala Ala Asn Thr
                165                 170                 175

Trp Thr Pro Leu Asp Ala Glu Leu Asp Leu Gly Ile Gly Leu Arg Tyr
            180                 185                 190

Asp Trp Gly Lys Leu Tyr Ala Ser Thr Ser Phe Tyr Asp Pro Leu Lys
        195                 200                 205

Gln Arg Arg Ile Met Leu Gly Tyr Val Gly Glu Val Asp Ser Ala Arg
    210                 215                 220

Ala Asp Val Ala Lys Gly Trp Ala Ser Leu Gln Ser Ile Pro Arg Thr
225                 230                 235                 240

Val Ala Leu Asp Glu Lys Thr Arg Thr Asn Leu Leu Leu Trp Pro Val
                245                 250                 255

Glu Glu Val Glu Ala Leu Arg Tyr Asn Ser Thr Asp Leu Ser Gly Ile
            260                 265                 270

Thr Val Glu Asn Gly Ser Ile Phe His Leu Pro Leu His Gln Ala Thr
        275                 280                 285

Gln Leu Asp Ile Glu Ala Ser Phe Arg Leu Asp Ala Ser Asp Val Ala
    290                 295                 300

Ala Ile Asn Glu Ala Asp Val Gly Tyr Asn Cys Ser Ser Ser Gly Gly
305                 310                 315                 320

Ala Ala Ala Arg Gly Ala Leu Gly Pro Phe Gly Leu Leu Val His Ala
                325                 330                 335

Ala Gly Asp Leu Arg Gly Glu Gln Thr Ala Val Tyr Phe Tyr Val Ser
            340                 345                 350

Arg Ala Leu Asp Gly Ser Leu Arg Thr Ser Phe Cys Asn Asp Glu Thr
        355                 360                 365

Arg Ser Ser Arg Ala Arg Asp Val Thr Lys Arg Val Val Gly Ser Thr
```

-continued

```
    370                 375                 380

Val Pro Val Leu Asp Gly Glu Val Leu Ala Met Arg Val Leu Val Asp
385                 390                 395                 400

His Ser Ile Val Gln Ser Phe Ala Met Gly Gly Arg Val Thr Ala Thr
                405                 410                 415

Ser Arg Val Tyr Pro Thr Glu Ala Ile Tyr Ala Arg Ala Gly Val Tyr
            420                 425                 430

Leu Phe Asn Asn Ala Thr Gly Ala Ser Val Thr Ala Glu Arg Leu Ile
        435                 440                 445

Val His Glu Met Ala Ser Ala Val Tyr Asp Glu Thr Val Met Val Lys
    450                 455                 460

Asp Ser
465
```

<210> SEQ ID NO 7
<211> LENGTH: 2132
<212> TYPE: DNA
<213> ORGANISM: Lolium perenne
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (814)..(814)
<223> OTHER INFORMATION: n is a, c, g, or t
<220> FEATURE:
<221> NAME/KEY: misc_feature
<222> LOCATION: (1827)..(1827)
<223> OTHER INFORMATION: n is a, c, g, or t
<220> FEATURE:
<221> NAME/KEY: misc_feature
<222> LOCATION: (2033)..(2033)
<223> OTHER INFORMATION: n is a, c, g, or t
<220> FEATURE:
<221> NAME/KEY: misc_feature
<222> LOCATION: (2036)..(2036)
<223> OTHER INFORMATION: n is a, c, g, or t
<220> FEATURE:
<221> NAME/KEY: misc_feature
<222> LOCATION: (2042)..(2042)
<223> OTHER INFORMATION: n is a, c, g, or t
<220> FEATURE:
<221> NAME/KEY: misc_feature
<222> LOCATION: (2044)..(2044)
<223> OTHER INFORMATION: n is a, c, g, or t
<220> FEATURE:
<221> NAME/KEY: misc_feature
<222> LOCATION: (2046)..(2046)
<223> OTHER INFORMATION: n is a, c, g, or t
<220> FEATURE:
<221> NAME/KEY: misc_feature
<222> LOCATION: (2054)..(2054)
<223> OTHER INFORMATION: n is a, c, g, or t
<220> FEATURE:
<221> NAME/KEY: misc_feature
<222> LOCATION: (2060)..(2060)
<223> OTHER INFORMATION: n is a, c, g, or t
<220> FEATURE:
<221> NAME/KEY: misc_feature
<222> LOCATION: (2063)..(2063)
<223> OTHER INFORMATION: n is a, c, g, or t
<220> FEATURE:
<221> NAME/KEY: misc_feature -continued
<222> LOCATION: (2067)..(2067)
<223> OTHER INFORMATION: n is a, c, g, or t
<220> FEATURE:
<221> NAME/KEY: misc_feature
<222> LOCATION: (2072)..(2072)
<223> OTHER INFORMATION: n is a, c, g, or t
<220> FEATURE:
<221> NAME/KEY: misc_feature
<222> LOCATION: (2074)..(2074)
<223> OTHER INFORMATION: n is a, c, g, or t
<220> FEATURE:
<221> NAME/KEY: misc_feature
<222> LOCATION: (2077)..(2077)
<223> OTHER INFORMATION: n is a, c, g, or t
<220> FEATURE:
<221> NAME/KEY: misc_feature
<222> LOCATION: (2082)..(2082)
<223> OTHER INFORMATION: n is a, c, g, or t
<220> FEATURE:
<221> NAME/KEY: misc_feature
<222> LOCATION: (2085)..(2085)
<223> OTHER INFORMATION: n is a, c, g, or t
<220> FEATURE:
<221> NAME/KEY: misc_feature
<222> LOCATION: (2088)..(2088)
<223> OTHER INFORMATION: n is a, c, g, or t
<220> FEATURE:
<221> NAME/KEY: misc_feature
<222> LOCATION: (2090)..(2090)
<223> OTHER INFORMATION: n is a, c, g, or t
<220> FEATURE:
<221> NAME/KEY: misc_feature
<222> LOCATION: (2096)..(2096)
<223> OTHER INFORMATION: n is a, c, g, or t

<400> SEQUENCE: 7
ggcacgagcc ggcttactct gctcggccga catacacgta cgcagatccc aacggtccgg 60
tctactatgg cggatggtac cacctcttct accagcacaa cccctatggc gactcgtggg 120
gaaacgtatc ttggggacat gccgtgtcca aggacctggt gaactggcgc cacctcccgg 180
tcgccttggt gcccgatcag tggtacgaca tcaacggcgt cctgacgggc tctatcacag 240
tgctcccaga cgggcgtgtc atcctgctat atacggggaa caccgacacc ttttcgcagg 300
tccagtgcct cgcagtgccc gccgacccat ctgacccgct ccttcgtagc tggatcaagc 360
accccgccaa ccccatcctt tttccgccac ctgggatcgg gctcaaggac ttccgtgacc 420
cgctcacagc ctggttcgaa cattccgaca acacgtggng caccatcatt ggatccaagg 480
atgacgacgg ccacgccggc atcgkcctta gctacaagac caccgacttt gtgaattatg 540
agctcatgcc agggaacatg catygtggcc ccgacggcac cggcatgtac gagtgccttg 600
acatctaccc tgtgggcggc aactcatccg agatgttggg tggcgactcc tcacctgagg 660
tgttgntcgt gctcaaggag agcgccaacg acgagtggca cgactactac gcgcttgggt 720
ggtttgacgc tgccgccaac acgtggacgc cacaggaccc cgaggcggac cttgggatcg 780
gcctcaggta cnactggggc aagtactacg cgtncaagtt cttctacgac ccgatcaaga 840
accggcgtgt cgtttgggct ttcgtcggcg agaccgactc tgarcaggcc gacaaagcca 900
agggatgggc gtccctyatg tcgattccca ggacsgtgga gcttgacaag aagacccgga 960
cgaacctgat ccaatggcma gtggaggaga tcgagaccct tcgcaggaac gtcacagacc 1020
tcggtggcat caccgttgaa gccggctccg tcattcacct tcccctccaa caaggcgggc 1080
agcttgacat cgaggcctcc ttccgtctca actcttcgga catcgatgca ctcaacgagg 1140
ccgacgtcgg cttcaactgc agtagcagcg atggggcagc cgtgcgtggt gcgctcggcc 1200
cctttggcct cctcgtcttc gccgacggtc gccacgaaca gacggcggcg tacttctacg 1260

-continued

```
tgtccaaggg cctcgacggc agcctcctga cgcactactg ccacgacgag tcacggtcga   1320

cgcgagcaaa ggacgtcgtg agccgggtgg ttggcggcac tgtgccagtg cttgacggtg   1380

aaacctttc  agtgagggtg ctagtggacc actccatcgt gcagagcttc gtgatgggtg   1440

ggaggaccac ggtgacatcg cgggcatacc cgacggaggc catctacgcc gcggcagggg   1500

tgtacctgtt caacaacgca acgagcgcca ccatcaccgc cgaagggctc gtcgtgtacg   1560

agatggcctc ggccgagagt cgggccttct tggctgacga catgtagatg aaaactagtc   1620

aagaacatgt caatggcgat cgtcaagctt gctggatggg gatcgtggtc acagagatct   1680

tcattcgcaa gttcgcgggt atgttgtagc tagggtggtg ccattgcatg ctgtggaggg   1740

gctgacggct ctctttggac tggattgcga tctggccaag acggtagatc gagaagccct   1800

cgtcgcccat ggctgggcaa agcagtntgg accagaaggt gttggttcat gtcgttgcac   1860

ctgatgacac gatggtgccc aacgaggcat cctgacttcc acatcgtctc tgcgcatgtc   1920

atgctcctta ctatctacct ctccccttct gttagttttg ttggtctgtc gtcctacctg   1980

atgtagctcc aatctttgtt gccggtgctt ttttgtccca gttgttcaac cgnatnttgc   2040

cnangnacgg ttanctaaan tgnttcnaac angnttngag cntgnaangn ttaaantttt   2100

tgctggaaaa aaaaaaaaaa aaaaaaaaaa aa                                 2132
```

<210> SEQ ID NO 8
<211> LENGTH: 534
<212> TYPE: PRT
<213> ORGANISM: Lolium perenne
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid

<400> SEQUENCE: 8

```
His Glu Pro Ala Tyr Ser Ala Arg Pro Thr Tyr Thr Tyr Ala Asp Pro
1               5                   10                  15

Asn Gly Pro Val Tyr Tyr Gly Gly Trp Tyr His Leu Phe Tyr Gln His
            20                  25                  30

Asn Pro Tyr Gly Asp Ser Trp Gly Asn Val Ser Trp Gly His Ala Val
        35                  40                  45

Ser Lys Asp Leu Val Asn Trp Arg His Leu Pro Val Ala Leu Val Pro
    50                  55                  60

Asp Gln Trp Tyr Asp Ile Asn Gly Val Leu Thr Gly Ser Ile Thr Val
65                  70                  75                  80

Leu Pro Asp Gly Arg Val Ile Leu Leu Tyr Thr Gly Asn Thr Asp Thr
                85                  90                  95

Phe Ser Gln Val Gln Cys Leu Ala Val Pro Ala Asp Pro Ser Asp Pro
            100                 105                 110

Leu Leu Arg Ser Trp Ile Lys His Pro Ala Asn Pro Ile Leu Phe Pro
        115                 120                 125

Pro Pro Gly Ile Gly Leu Lys Asp Phe Arg Asp Pro Leu Thr Ala Trp
    130                 135                 140

Phe Glu His Ser Asp Asn Thr Trp Arg Thr Ile Ile Gly Ser Lys Asp
145                 150                 155                 160

Asp Asp Gly His Ala Gly Ile Ala Leu Ser Tyr Lys Thr Thr Asp Phe
                165                 170                 175
```

-continued

```
Val Asn Tyr Glu Leu Met Pro Gly Asn Met His Arg Gly Pro Asp Gly
            180                 185                 190

Thr Gly Met Tyr Glu Cys Leu Asp Ile Tyr Pro Val Gly Gly Asn Ser
        195                 200                 205

Ser Glu Met Leu Gly Gly Asp Ser Ser Pro Glu Val Leu Xaa Val Leu
    210                 215                 220

Lys Glu Ser Ala Asn Asp Glu Trp His Asp Tyr Tyr Ala Leu Gly Trp
225                 230                 235                 240

Phe Asp Ala Ala Ala Asn Thr Trp Thr Pro Gln Asp Pro Glu Ala Asp
                245                 250                 255

Leu Gly Ile Gly Leu Arg Tyr Asp Trp Gly Lys Tyr Tyr Ala Xaa Lys
            260                 265                 270

Phe Phe Tyr Asp Pro Ile Lys Asn Arg Arg Val Val Trp Ala Phe Val
        275                 280                 285

Gly Glu Thr Asp Ser Glu Gln Ala Asp Lys Ala Lys Gly Trp Ala Ser
    290                 295                 300

Leu Met Ser Ile Pro Arg Thr Val Glu Leu Asp Lys Lys Thr Arg Thr
305                 310                 315                 320

Asn Leu Ile Gln Trp Pro Val Glu Glu Ile Glu Thr Leu Arg Arg Asn
                325                 330                 335

Val Thr Asp Leu Gly Gly Ile Thr Val Glu Ala Gly Ser Val Ile His
            340                 345                 350

Leu Pro Leu Gln Gln Gly Gly Gln Leu Asp Ile Glu Ala Ser Phe Arg
        355                 360                 365

Leu Asn Ser Ser Asp Ile Asp Ala Leu Asn Glu Ala Asp Val Gly Phe
    370                 375                 380

Asn Cys Ser Ser Ser Asp Gly Ala Ala Val Arg Gly Ala Leu Gly Pro
385                 390                 395                 400

Phe Gly Leu Leu Val Phe Ala Asp Gly Arg His Glu Gln Thr Ala Ala
                405                 410                 415

Tyr Phe Tyr Val Ser Lys Gly Leu Asp Gly Ser Leu Leu Thr His Tyr
            420                 425                 430

Cys His Asp Glu Ser Arg Ser Thr Arg Ala Lys Asp Val Val Ser Arg
        435                 440                 445

Val Val Gly Gly Thr Val Pro Val Leu Asp Gly Glu Thr Phe Ser Val
    450                 455                 460

Arg Val Leu Val Asp His Ser Ile Val Gln Ser Phe Val Met Gly Gly
465                 470                 475                 480

Arg Thr Thr Val Thr Ser Arg Ala Tyr Pro Thr Glu Ala Ile Tyr Ala
                485                 490                 495

Ala Ala Gly Val Tyr Leu Phe Asn Asn Ala Thr Ser Ala Thr Ile Thr
            500                 505                 510

Ala Glu Gly Leu Val Val Tyr Glu Met Ala Ser Ala Glu Ser Arg Ala
        515                 520                 525

Phe Leu Ala Asp Asp Met
    530


<210> SEQ ID NO 9
<211> LENGTH: 9538
<212> TYPE: DNA
<213> ORGANISM: Lolium perenne
<220> FEATURE:
<221> NAME/KEY: misc_feature
<222> LOCATION: (3698)..(3698)
<223> OTHER INFORMATION: n is a, c, g, or t
<220> FEATURE:
```

-continued

<221> NAME/KEY: misc_feature
<222> LOCATION: (4669)..(4669)
<223> OTHER INFORMATION: n is a, c, g, or t
<220> FEATURE:
<221> NAME/KEY: misc_feature
<222> LOCATION: (5546)..(5546)
<223> OTHER INFORMATION: n is a, c, g, or t
<220> FEATURE:
<221> NAME/KEY: misc_feature
<222> LOCATION: (5611)..(5611)
<223> OTHER INFORMATION: n is a, c, g, or t
<220> FEATURE:
<221> NAME/KEY: misc_feature
<222> LOCATION: (5615)..(5616)
<223> OTHER INFORMATION: n is a, c, g, or t
<220> FEATURE:
<221> NAME/KEY: misc_feature
<222> LOCATION: (6033)..(6033)
<223> OTHER INFORMATION: n is a, c, g, or t
<220> FEATURE:
<221> NAME/KEY: misc_feature
<222> LOCATION: (6221)..(6221)
<223> OTHER INFORMATION: n is a, c, g, or t
<220> FEATURE:
<221> NAME/KEY: misc_feature
<222> LOCATION: (6404)..(6404)
<223> OTHER INFORMATION: n is a, c, g, or t
<220> FEATURE:
<221> NAME/KEY: misc_feature
<222> LOCATION: (6502)..(6502)
<223> OTHER INFORMATION: n is a, c, g, or t
<220> FEATURE:
<221> NAME/KEY: misc_feature
<222> LOCATION: (6528)..(6528)
<223> OTHER INFORMATION: n is a, c, g, or t
<220> FEATURE:
<221> NAME/KEY: misc_feature
<222> LOCATION: (6533)..(6534)
<223> OTHER INFORMATION: n is a, c, g, or t
<220> FEATURE:
<221> NAME/KEY: misc_feature
<222> LOCATION: (6536)..(6536)
<223> OTHER INFORMATION: n is a, c, g, or t
<220> FEATURE:
<221> NAME/KEY: misc_feature
<222> LOCATION: (6619)..(6619)
<223> OTHER INFORMATION: n is a, c, g, or t
<220> FEATURE:
<221> NAME/KEY: misc_feature
<222> LOCATION: (6627)..(6627)
<223> OTHER INFORMATION: n is a, c, g, or t
<220> FEATURE:
<221> NAME/KEY: misc_feature
<222> LOCATION: (6632)..(6632)
<223> OTHER INFORMATION: n is a, c, g, or t
<220> FEATURE:
<221> NAME/KEY: misc_feature
<222> LOCATION: (6647)..(6647)
<223> OTHER INFORMATION: n is a, c, g, or t
<220> FEATURE:
<221> NAME/KEY: misc_feature
<222> LOCATION: (6675)..(6675)
<223> OTHER INFORMATION: n is a, c, g, or t
<220> FEATURE:
<221> NAME/KEY: misc_feature
<222> LOCATION: (6696)..(6696)
<223> OTHER INFORMATION: n is a, c, g, or t
<220> FEATURE:
<221> NAME/KEY: misc_feature
<222> LOCATION: (6735)..(6735)
<223> OTHER INFORMATION: n is a, c, g, or t
<220> FEATURE:
<221> NAME/KEY: misc_feature
<222> LOCATION: (6749)..(6749)
<223> OTHER INFORMATION: n is a, c, g, or t
<220> FEATURE:
<221> NAME/KEY: misc_feature
<222> LOCATION: (7516)..(7516)
<223> OTHER INFORMATION: n is a, c, g, or t -continued
<220> FEATURE:
<221> NAME/KEY: misc_feature
<222> LOCATION: (9095)..(9095)
<223> OTHER INFORMATION: n is a, c, g, or t
<220> FEATURE:
<221> NAME/KEY: misc_feature
<222> LOCATION: (9121)..(9121)
<223> OTHER INFORMATION: n is a, c, g, or t
<220> FEATURE:
<221> NAME/KEY: misc_feature
<222> LOCATION: (9260)..(9260)
<223> OTHER INFORMATION: n is a, c, g, or t
<220> FEATURE:
<221> NAME/KEY: misc_feature
<222> LOCATION: (9471)..(9471)
<223> OTHER INFORMATION: n is a, c, g, or t

<400> SEQUENCE: 9
ctcgtggttc aagttacgaa caccacacaa cacacatccg gatcatgata aacattacgg 60
cccaaaaggt gccgagcgga gcctgattat tggcctacgc cacctggtga acttcttgct 120
gctgctgcgg ccggttctgc tgagcgaaaa ccggttgcgc atttgccccg gttagcggtg 180
gcggtggtgg caacgcctcg aaaacttgtt ctctgtcatc tttcatcatg cctctctcca 240
tcaacctctt ggtccaggag caatcttttt gttaggtggt ttgccggtct cgttggattc 300
ggtgtgtgcg aacggcacgg ctgatccata gcggattcca tggtgtactt ggcctggtcc 360
tgccatggtt ttttctccac ccattgtttc ttttggccag cccacggctg cgttccagtt 420
ttctgccttt ggcttccacc agcgcctgaa ttgtcttgca ctgcagccac ttgttgcatt 480
ccatatctcc tatccgggaa atcttccgtt gttttgttat gatggttgtt ccggtgctga 540
tctgggcgcg gtgggaatct tggtgctgga ttcgctccga tcgccggttg cattggatct 600
cccagcgcat aggttatcag ccacccagat catttcggtt aaggtggttg gcatgtttct 660
ttgtaacttt gccamaacgg tgagcctctc cggcatccat tgctgaacca agcaatttcc 720
tgtgcttcaa tcacaccctc gcaagagttt cttgtggagt tccaccgggt cagatagccc 780
cggtctgttt tattctcgcg ctgttggcac atggcgagct gctgcggtct gtttggcctc 840
cggtatgtac tgctgaagtt gctcacgaat gcttcttcaa aatcaagcca gccgtttatg 900
cttccctttg gcaaattgtt gagccaaatg cgagtcggtc ctaccagcac tgacggtatg 960
tatcttacca cccagcgccg gtttccttcg ccagctgcgg ttcctccacc tccagcgaca 1020
tataccgttg tgacgtagtc tgccagccaa tcttccggct ttgtggtgcc atcgtacgtt 1080
tttgtgtcac ggggcaactg aaagttgcgt accggttgct cttccctcat gatccgcggg 1140
tcaaaacatt gtggaaccgg cggaccctca gcctcgatca tctcaaraga aatatacttt 1200
tgtccaagcc tatgtcgtgc atctctatcc gggcaaagca tctttctccc aaacgttctc 1260
cgagagggtt tcggtrattt ccggttcgct cccatccgta atcggcttca tcataccggt 1320
tcggtgcgac cgtgacaccc cttgggtacc tcagcacttc tgcctcttgt gcagcgtgtc 1380
ccgcccttgc tgggcgatag ttttgcccgg tttcaccgtt tccggcacca gcatttccgg 1440
cataaccgtt tccggcagtg cctgcccctt ggctttttct accgggatcg tgttgcccgg 1500
ctctctgttt tccggccaaa accggatcat aaacagtcat ccgttgtgca tttgcatctt 1560
tttctcttct tttgctcgga tggggggacg aagcatgccc atgcgacttg cttccggcat 1620
ttcttgccga acgcaccaat tgcgatgcag cagctgcctt ggtgtttcgg gccatctctg 1680
tattttgtgc ctcaatcata tctagcagtt ctcccctagc ttgatgtttt gctaaggcat 1740
ctcctgaaaa ggaatcacat gcttatacag cagccctagt agctttcaaa gttttatccg 1800

-continued

```
gactgctata cttaggtttc tctaccatga tcaaagatac cgacacgctc ttaccggaaa   1860
gaacctcccg gcgtagatcc tgatctaggt tacgacctct aagccggttt ccagctactc   1920
tagcagggtt tgcgctaaca gaagcaaaac catgagcagc gttatactca cgtagggtca   1980
ggttgagctc ctgctgagcc ttgacgatgt ttcctgcact ggagagcagc ttctgtcgtt   2040
gtgcctccag ttcggcttgg gtggctgcag cgtcggtgtt gtgcgcgatg ggcgtggcca   2100
acaagctcat ggccgcttgc agtggggttg cttccggtgg cgcggtagaa gcaccggcga   2160
cgatctcatc gcgctcggtc ggaggcttgg ccgtgcacgt ggacttggtt tgcccagggc   2220
cctcccctgc actttcttta ccggcgcctc cagcgccagc catcatcacc tccacgctgt   2280
cggcggcgcg gtcgtagcgc ggcccgcgag aagctgaaga ccttggcgga tccggcgcca   2340
ccagcaccag cgatgggtac tggcgctctg gcacggtgcc gaagtagatg cggtgggagc   2400
cggactcgaa gatgcggccg ttcttgggga agcggccacc gttggtgaag cagcctgcgt   2460
tgttgttgac gaaatccagc gagccgraga cggtgaggag gcctgcctgg atatgaactc   2520
cagcaagcgc agctgctggc cccatggtgg gcgccaactg tcgtcgtggt gtaacaacag   2580
atgccatagg atggcttaag ttggggccga atgtgcgcta gaggatccgg gggagggttt   2640
ggttaacagg gaaagagaga aaagaagctg gtatgtattg atgaacttgg ccgatggcca   2700
gaggttgaag acagtacggt acaggacctt agcaacttgc tactaaactg cctaatttct   2760
ctattgaatc gatctcttcg tgctagggtg taccccctct ccttatatag gggagagggt   2820
ggcttacaag ggaagaaacc ctaatggaat ctttgatgag ctaagctact ttataaagct   2880
actctggccc agctgacacc ggctctatct ttaatcaggg actgatgacc tcggccggta   2940
tcttttacgt caccttctgc tttggtgcca gggcttcgat taaagctgaa gtgcttcgct   3000
catctttgtc ctttagtcct tggtggaatc tttggctgaa gtgccgacag gctacagtga   3060
tccaataccg gtttgccggt acctttacct ctgagttccg gtaccttggt ccttggtgat   3120
atggcctcct tattgccagg actccggtat accccctctg ggataccggt tcgtactagc   3180
ttcgcctagc taagattaac tttagagtcc ggatcactct ttgatccggt ttataactac   3240
catattatgg cttatttgcc atagtcttgg cctaccgggg gccatccccc cgacagcccc   3300
ttacgccgcc tgatgttatc attggacggc aggcgtttcc tggccaactg ccataggaag   3360
caccttccct gggaccatga tctgccacaa gtcactgaag tgcttggaag gggtgccctg   3420
gcagagctta aggtacaaag accgcactaa gaatctcccc gaagattcta gcgcccaagt   3480
aaccttatct tgcaaacctg aggtgggtgg taccgtgaac tcccgcgtga ggttagacaa   3540
atcaacacga tccccaaagc ccagcccgcg ccgaaacggt agatgtcagg cccccccaca   3600
acgagaggag tcgggtcgag gcctcctgct cagtcacaat ggcaaagagc gaggggaacc   3660
tatcgmacag gggtcccgac ccctgccact agtcctgnta gaagctcgcc gtcttaccat   3720
tatgcactgt gtgtctcgcc cccaagcgaa aaaggtgttt gagtttctgg atagagttcc   3780
agaactgcga gcccggtcgg tgtgcatcta acatcaggtc cttatccctg aggtacttgt   3840
tccgtaggat ctccgcccag aggccttgct ccccagcata aagcctccag atccacttaa   3900
ccacaagaca cgcgttcatg agcctggtgt ccacaattcc aagcccccaa gctctttggc   3960
ctacagatcg ccgaccacct cacccagtgg tatttccgct tggtactgct ggcttcccaa   4020
tagaagcgtg atcggtgtct atccataatg atgtgcggcc cctcccccag aaggaaaacc   4080
gtcatcgcca tggcatgaag cggtaggcta gataagcaag tgttagtgag ggtcagccta   4140
cgccgcagag gacataagct tccccatcca cggctcggcg cgcttaccta ccttggccat   4200
```

-continued

```
aagaggaccc cagtccgcga gcagtgagag cgcgatcact gatcggtagc cscatgtatg   4260
agaatggaaa ggacccaagt ttgcagttga gcatatgcgc gatcctgggc ccatcttcct   4320
gatccatacc taacaccata acctcacttt tgtggaaatt gatccttagc cccgacatgc   4380
tctcaaaaca gagcagaatg tacttcaaat tggccacggc caaatcatca ggctggatca   4440
taataatggt gtcgtcagca tattacaagt gagatacccc caggtatcaa gtgtgggatt   4500
acccccgcag tatgaccggc ccctctagct ttctctagaa tagcagctag ggcttcgaca   4560
acgtagtcga agagaatagg ggatagggggg tcaccctggc gcacccccgcg ccaattgcga   4620
aagtatttcc caatgtctcc attaatggag attgcagtct ggcctaccna gaccagactg   4680
aggscccctgt gcacmtaaag ttggctcaaa accccttgca tataagamcc tcacggagga   4740
agggcccagt tcacccggat cataggcttt ctagaagtct aattttagga atactcccct   4800
aagcttcctg gacttggatt catggatgat ttcttgggag ggccagaacg cccctcgtga   4860
atgtgtctcc ctttgataaa ggcggattgg gaacgactaa tggtcatgtg cgcaataggg   4920
gatagcctag tggcataagc tttggcaaca aacttaaaaa tcacattaat cagcgcaatc   4980
ggcctaatgt gtcacattcc ccatctccta tggttttctc gcgccacata ttttatatgc   5040
cggaacggtg gccaaccggc taactggaat tggccaacaa tggtgacsca tgtwaagaga   5100
ctactaggtc atggtcaaga cgatcatgta cgtagagggg caaaaaaattg catgtgaggt   5160
taaaccgggt cggagaagaa gcggcagcgg cggcgcgccg tcgacacggt ctsgaggttg   5220
aagatgaagg gcatctcaag atttccattg taatttttat tttcgttcgg gagtgtttct   5280
tttaatgcta aggttttatt cgcaaaaaaa aaagaaatgg gttggggaag aagggaaaag   5340
gaatggagta acaaggcata tacaaaaaaa gattatgtac acacggtcac aggaataggg   5400
aagggaagga tagagaataa aaagtgccta gaaatggata gcaactatat atccaaaaag   5460
aaaagaaatc aaccgggcga gcgataagag aggatccacc gatctcgtag ggtcaatgtc   5520
catttcaccc tcgctgaccg cccggnccca cactccagcc accctcaccg gcctacgcac   5580
gcgcttgcat cccgcgccct gtttccattt ngggnncccg cgcagctata aatcccgctc   5640
gttggctcgc tcgggaagcc acatccatca gaatctgctc catttgtttt ggaattcgcc   5700
catggagtct cggtccattc ccggcgcgta cgcgtacgag ccgctgcccc actcctacga   5760
cgacgcccat ggccacgacg accgccggag caccggcggc gtgaggtggc gcgcgtgcgc   5820
ggccgttctt gcggcgtcgg ccctggtcgt cttcgtggtc gccagcacgc tcgccgggtc   5880
gagggtggac cgcgtggycg tcgacgtggc cgccatgccg gcgctgtcgg agacggcgag   5940
gagccgcggg agggacgcgg gcgtgtcgga gaagacgtcc ggcgcggcgg acgagatggg   6000
gttcctcggc gccggcgccg gcgccgacgc cgncgggttc ccgtggagca acgccatgct   6060
gcagtggcag cgcacgggtt tccatttcca gcccgagatg aactggatga acggtacgtg   6120
ccacgatcca tatccattac tcctttcctt ttcccgtccg attcaggctc agatgtatat   6180
atcttgcttt catatctatc tatacatctc tcgcgcgtgg ntgwtttgat cgacatatat   6240
aagctgacgc tgttgccatt gctttctttc ctgtttgctc gmtgctgcgg ccgkcggcgt   6300
accttctycg gcgacgacat gcatgcagat cccaacggtt agtaccgatt aaccgatctc   6360
tatcccatgg aatattcttg ttcaattgtc cgcttgcccs rtcnccgcct gtctcgcgcg   6420
cgcgcgcgga agggaaacca tatctgcatc tattttgacc acgcgccatt ggttgccgca   6480
aaactgaaac cggtgtagat gnatatagag agatccagat tacctcgntc ccnntntctc   6540
```

-continued

```
attggtacac acgattaatc acgtccccac tgcaataatg tgccagccgt aaccacaaat   6600
gattattatc ctttatttng ccataanctt angcatacat aaatccncct aatcacctat   6660
ccacaccttc cttanctgac tctagtttta gtatanattt gcatctctta taactaatcc   6720
ttgttttcat ctatntacgg cctggattna tctaatcttr aattrtcyrt gcaggtccgg   6780
tktattaccg mggatggtac cacctcttct accagtacaa cccygagggg rcggtgtggg   6840
gcaacatcgc gtggggccac gcygtstcyc gggacctrgt ccactggcgc cacctcccgc   6900
tcgcmatggt gccygaccaa tggtacgaca tcaamggtgt ctggacrggc tccgccacyg   6960
tgttcccyga ygggacmctc aacatgctct acacggggtc caccaacgcc tccgtgcagg   7020
tycagtgcct cgccgtgccc gaggacccca wsgactccyt cctccgcaac tggaccaagc   7080
acgaagccaa ycccgtgctc ctcccgccrc ccgggatcgg wgacaagrac ttccgtgacc   7140
cgaccaccgc mtggttcgay gagtccgacc agacgtggcg mmcgtcatcg ggtccaagga   7200
caacaacgrc caygccggya tsrccatggt gtacaagacc margacttcc tcaactasga   7260
gctcatcysa ggatacttgc atcgtgtcga tggcactggc atgtgggagt gcatcgactt   7320
ctaccccgtt ggaggcaaga acggcagcga ggagttgtac gtgatcaagg agagcagcga   7380
cgacgaccga catgactggt acacgctagg gaaatacgac gcggcagcca acacgttcac   7440
ggccgcggac ccggagaacg acctagggat tgggctgagg tacgactggg gcaagtttta   7500
cgcgtccaag accttntacg atccggccaa gaaccggcga gtgctctggg gatggatcgg   7560
cgagaccgac tctgagcgcg ccgatgtcgc caagggatgg gcatccctca tggtatgctc   7620
gcttttccct tactgcttct catctttgtt tcgttatgca tatgttagtt ccatctcata   7680
catcctgcaa ttgatcagac cttcaacctg cttaatcgaa atgttgatgc aagcatgcat   7740
atagatgctg acggatcggc ccgccgacac atacgttggc agagaactgt taatcgcatt   7800
gtcaatggga tgagaatgga tttatgtctg ctaattggtc gtggggattg gcgacgttgt   7860
cacgcatcga ttaattgata cacaagtcgc agtcatgccg tttaacgttt tcttttcctg   7920
tttaaccacc tacctaccta taggtcgcat gtcgccagct atatcgctgt tgagaagatt   7980
gaaatccaag agcaagtaca ataagatcta gtcagctggc tacaaggatt aaaataatat   8040
atttgtgtct agttggagga gagataggag gagagagaat gtgagtatgc tcttatgcaa   8100
gagctagctc tagcacgtgc tcctaggcaa ggtgtgtgaa tgaaaggtgg gtcatccatt   8160
gaaaaaatag tacattctaa tagccaacta ttgtacttgt tggctacatg ttgactatag   8220
atgacatggc atcttgctta tagcccaaca accggctata ctattggagt tgctcttaag   8280
atgacaactg ggatttaaaa cgtgcatgca tgttccgtga gatctttagt taatcccaac   8340
tcatgcacct aattaagatg taccagttga cctgactgtg caaacgtacg tacccatacc   8400
cttctcgaag ctattagtat aatgcatgta accctttttg gtgatcctct cctgtggtag   8460
gttctatact agtattcaat tgaaaggcta gctgaatttc aagagtactt tttctctgac   8520
cagttccata ttctccgttg catcttccaa actttggtca acgggtgcaa gccaagtgtc   8580
atttctcaac aacatgttat agcaaagact atatccaacc caactggcat gcatgtgccc   8640
tagctagaca ccacatgtgc acgccacgtc gatcccacgt ggaaccacgt ggatgcctaa   8700
ataaatgtat cgatggcttc tgatgctgac cgttatgatt ggcaacggta tcttaattta   8760
tctgctccca gctaaccacc aaatttcaac tttctcctac cttcctgtct ggaatagaca   8820
ggatctgcat ggtaatatta tgtatttgat tagtcgtgcc aaacatggat ccgactaatc   8880
gttcttatcg agtttgaaca ttctttactc ttgtgcatat gtgacaccaa tttgttctgc   8940
```

-continued

```
tcttgtattt ttcttttcca agatgttgat gtgcataatg cgtgatcgat cattggacct   9000

acctctgctt gaattatttt aactaagaaa atgattgatt gatgtgtgct tgcagtcgat   9060

tccgaggacg gtggaactcg acgagaagac ccggnccaac ctcatccaat ggccggtgga   9120

ngagctcgag accctccgca tcaagtccac cgacctcggt ggcgtcacca tcgaccacgg   9180

cagcgtctac ccactccctc tccaccgcgc cacacaactc gacattgagg cctccttccg   9240

catcgacact gccaccgtcn ctgccctcaa tgaggctgac gttggctaca attgcagcac   9300

cagcggtggc tctgccaacc gtggcgcact cggccccttt ggcctcctcg tcctcgccga   9360

cggtaaggca gagcagacgg cagtgtactt ctatgtggcc aagggcctcg acgggaccct   9420

ccaaacccac ttctgccacg acgagtcacg gtcgacggta tcgataagcc ntgatatcga   9480

attcctgcag cccgggggat ccactagttc tagagcggcc gccaccgcgg tggagctc     9538
```

<210> SEQ ID NO 10
<211> LENGTH: 554
<212> TYPE: PRT
<213> ORGANISM: Lolium perenne
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (259)..(259)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (290)..(291)
<223> OTHER INFORMATION: Xaa can be any naturally occurring amino acid
<220> FEATURE:
<221> NAME/KEY: misc_feature
<222> LOCATION: (297)..(297)
<223> OTHER INFORMATION: Xaa can be any naturally occurring amino acid
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (306)..(306)
<223> OTHER INFORMATION: Xaa can be any naturally occurring amino acid
<220> FEATURE:
<221> NAME/KEY: misc_feature
<222> LOCATION: (388)..(388)
<223> OTHER INFORMATION: Xaa can be any naturally occurring amino acid
<220> FEATURE:

-continued

```
<221> NAME/KEY: misc_feature
<222> LOCATION: (434)..(434)
<223> OTHER INFORMATION: Xaa can be any naturally occurring amino acid
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
<222> LOCATION: (489)..(489)
<223> OTHER INFORMATION: Xaa can be any naturally occurring amino acid

<400> SEQUENCE: 10

Met Glu Ser Arg Ser Ile Pro Gly Ala Tyr Ala Tyr Glu Pro Leu Pro
1               5                   10                  15

His Ser Tyr Asp Asp Ala His Gly His Asp Asp Arg Arg Ser Thr Gly
            20                  25                  30

Gly Val Arg Trp Arg Ala Cys Ala Ala Val Leu Ala Ala Ser Ala Leu
        35                  40                  45

Val Val Phe Val Val Ala Ser Thr Leu Ala Gly Ser Arg Val Asp Arg
    50                  55                  60

Val Xaa Val Asp Val Ala Ala Met Pro Ala Leu Ser Glu Thr Ala Arg
65                  70                  75                  80

Ser Arg Gly Arg Asp Ala Gly Val Ser Glu Lys Thr Ser Gly Ala Ala
                85                  90                  95

Asp Glu Met Gly Phe Leu Gly Ala Gly Ala Gly Ala Asp Ala Xaa Gly
            100                 105                 110

Phe Pro Trp Ser Asn Ala Met Leu Gln Trp Gln Arg Thr Gly Phe His
        115                 120                 125

Phe Gln Pro Glu Met Asn Trp Met Asn Asp Pro Asn Gly Pro Val Tyr
    130                 135                 140

Tyr Arg Gly Trp Tyr His Leu Phe Tyr Gln Tyr Asn Pro Glu Gly Xaa
145                 150                 155                 160

Val Trp Gly Asn Ile Ala Trp Gly His Ala Val Ser Arg Asp Leu Val
                165                 170                 175

His Trp Arg His Leu Pro Leu Ala Met Val Pro Asp Gln Trp Tyr Asp
            180                 185                 190

Ile Xaa Gly Val Trp Thr Gly Ser Ala Thr Val Phe Pro Asp Gly Thr
        195                 200                 205

Leu Asn Met Leu Tyr Thr Gly Ser Thr Asn Ala Ser Val Gln Val Gln
    210                 215                 220

Cys Leu Ala Val Pro Glu Asp Pro Xaa Asp Ser Xaa Leu Arg Asn Trp
225                 230                 235                 240

Thr Lys His Glu Ala Asn Pro Val Leu Leu Pro Pro Pro Gly Ile Gly
                245                 250                 255

Asp Lys Xaa Phe Arg Asp Pro Thr Thr Ala Trp Phe Asp Glu Ser Asp
            260                 265                 270

Gln Thr Trp Arg Thr Val Ile Gly Ser Lys Asp Asn Asn Xaa His Ala
        275                 280                 285

Gly Xaa Xaa Met Val Tyr Lys Thr Xaa Asp Phe Leu Asn Xaa Glu Leu
    290                 295                 300

Ile Xaa Gly Tyr Leu His Arg Val Asp Gly Thr Gly Met Trp Glu Cys
305                 310                 315                 320

Ile Asp Phe Tyr Pro Val Gly Gly Lys Asn Gly Ser Glu Glu Leu Tyr
                325                 330                 335

Val Ile Lys Glu Ser Ser Asp Asp Asp Arg His Asp Trp Tyr Thr Leu
            340                 345                 350
```

-continued

```
Gly Lys Tyr Asp Ala Ala Ala Asn Thr Phe Thr Ala Ala Asp Pro Glu
        355                 360                 365

Asn Asp Leu Gly Ile Gly Leu Arg Tyr Asp Trp Gly Lys Phe Tyr Ala
    370                 375                 380

Ser Lys Thr Xaa Tyr Asp Pro Ala Lys Asn Arg Arg Val Leu Trp Gly
385                 390                 395                 400

Trp Ile Gly Glu Thr Asp Ser Glu Arg Ala Asp Val Ala Lys Gly Trp
                405                 410                 415

Ala Ser Leu Met Ser Ile Pro Arg Thr Val Glu Leu Asp Glu Lys Thr
            420                 425                 430

Arg Xaa Asn Leu Ile Gln Trp Pro Val Xaa Glu Leu Glu Thr Leu Arg
        435                 440                 445

Ile Lys Ser Thr Asp Leu Gly Gly Val Thr Ile Asp His Gly Ser Val
    450                 455                 460

Tyr Pro Leu Pro Leu His Arg Ala Thr Gln Leu Asp Ile Glu Ala Ser
465                 470                 475                 480

Phe Arg Ile Asp Thr Ala Thr Val Xaa Ala Leu Asn Glu Ala Asp Val
                485                 490                 495

Gly Tyr Asn Cys Ser Thr Ser Gly Gly Ser Ala Asn Arg Gly Ala Leu
            500                 505                 510

Gly Pro Phe Gly Leu Leu Val Leu Ala Asp Gly Lys Ala Glu Gln Thr
        515                 520                 525

Ala Val Tyr Phe Tyr Val Ala Lys Gly Leu Asp Gly Thr Leu Gln Thr
    530                 535                 540

His Phe Cys His Asp Glu Ser Arg Ser Thr
545                 550
```

<210> SEQ ID NO 11
<211> LENGTH: 4819
<212> TYPE: DNA
<213> ORGANISM: Lolium perenne
<220> FEATURE:
<221> NAME/KEY: misc_feature
<222> LOCATION: (1903)..(1903)
<223> OTHER INFORMATION: n is a, c, g, or t
<220> FEATURE:
<221> NAME/KEY: misc_feature
<222> LOCATION: (4028)..(4028)
<223> OTHER INFORMATION: n is a, c, g, or t
<220> FEATURE:
<221> NAME/KEY: misc_feature
<222> LOCATION: (4447)..(4447)
<223> OTHER INFORMATION: n is a, c, g, or t
<220> FEATURE:
<221> NAME/KEY: misc_feature
<222> LOCATION: (4465)..(4465)
<223> OTHER INFORMATION: n is a, c, g, or t
<220> FEATURE:
<221> NAME/KEY: misc_feature
<222> LOCATION: (4467)..(4467)
<223> OTHER INFORMATION: n is a, c, g, or t
<220> FEATURE:
<221> NAME/KEY: misc_feature
<222> LOCATION: (4683)..(4683)
<223> OTHER INFORMATION: n is a, c, g, or t

<400> SEQUENCE: 11

```
ggatccagat gtgtagcagc attattgtcc tacagtactt aattaactct tatgtggacc      60

tttccagttt gatatttccg gctcatgtgg agtatcagcg gtcgtgatag gagatcccaa     120

aagcaaccaa tggccaaatc tcttgggccc caaattctgg ccattagtgt actaaactag     180

gcaccttgtg gtatagagtc caaatgatgg agaaccgtcc tttataaaaa aaaaccccac     240
```

-continued

```
atgtcctgcg tcattcccaa taattgtgcc acggcagcat gaacttcgca tgtgcgtaac    300
aaagatcagc ggacaacggc aatatcgcaa gctccatgcc tcacgcgatt gctccgtttt    360
gtagagtaac gagtgttaaa attgattgat ggtgctttat tcacgcgatg taacaatgtt    420
ggtaaattca tattttttgg gtaaaaaaaa aaagtgcttc aatagcatga aacacatgta    480
tgctctttct atgagctata tatataccct gtggtaagcc ctccgttgga ttgtttcaaa    540
ctaaaacaaa aaacttgctg tagcagttca gtaagaaaac tgaatttctg aaccagtttt    600
cagttttctg aatctgttcc atatagtgtt atccacgtcg agttttgggc ttttatatat    660
acatctacaa atgtgtgcta caattacatg tgtacttttt gaataggtcg attgtgaatg    720
ctttggcaag cacctctaaa aaattagatt agaaggcaac cccgttacag tacaccctca    780
ttgttggtcg tcgacctatt atctccctac ggcctcttgt accgtctata gaacggtcmc    840
atttgacatc tacaaattca cctttgtaat cagacactat atcattctta aagattcaat    900
ggtaacgctc aagggcaatc aatttcaacc gcaacgaact cggacggttt gctgatgatg    960
acctcttctc cggcctctag gattctcccc gaccataagt tgatgctttc aaacaaccag   1020
ctgggtcgac aacacccatt gctagagaga cactatatgt tttgtttccc agctaattta   1080
ctgcacggca actatctgta ctggatttcc tgtgggtata tatagtagta tttcttcaat   1140
taatggcatt tgaaaaataa atatgtttgg tgaggcttga agcacatata ggatggagaa   1200
gagagtgtgt ccacaaatat agatctactg ctacctcgcc caccctagta agtaagtaga   1260
gtgatggaat cagctgagcg agcccgtcca gagctgggat atgcgatctc acatggccaa   1320
tgtcggcctt ctccgtcgct gacccgtggg ccccacgagc cagacgtgtc cgtgctggcg   1380
caccctgcca ttttaatctt tagcgcgatc aacggacggg agcgctcgac ggagacgcgt   1440
acgtacgtac gtacaggctg ttcaaaacta gtctatttga cgcaacgggc caaaacccct   1500
gcgaaaaccc ctgctataaa tcgcgcccgc tcgctcctcc gtccatccat ccatccaccg   1560
cccagatcag ccttcctcgg aaccatcgac cgggccgccg ccgacgcgac gcgacgccat   1620
ggagtcccca agcgccgtcg tccccggcac cacggcgccg ctgcttcctt atgcgtacgc   1680
gccgctgccg tcgtccgccg acgacgcccg tcaaaaccgg agtggcggga ggtggcgcgc   1740
gtgcgccgcc gtgctggccg catcggcgtt ggcggtggtc gtcgtggtcg ggctcctcgc   1800
gggcggcagg gtggatcggg tcccggccgg cggagacgtg gcgtcggcca cggtgccggc   1860
cgtgccgatg gagttcccga ggagccgggg caaggacttc ggngtgtcgg agaagtcctc   1920
cggtgcctac tccaccgacg gcgggttccc gtggagcaac gccatgctgc agtggcagcg   1980
caccgggttc catttccagc cggagcagca ctacatgaac ggtacggsgc atgcagttgt   2040
tgctatctag tagtgtttca gattcagatt tcgtttttcc ccttgatctg acgtacgtac   2100
gtgggtctga ttctgatcat ggatcgttcg aggaaaccag ctaatcgatt tcctgtttgt   2160
ctgttgccgg cggcgtattc tgcagatccc aacggccccg tgtactacgg cggatggtac   2220
cacctcttct accagcacaa ccccaagggc gacagctggg gcaacatcgc gtgggcccac   2280
gccgtctcca aggacatggt caactggcgc cacctccctc tcgccatggt tcccgaccag   2340
tggtacgaca gcaacggcgt cctcaccggc tccatcaccg tgctccccga cggccaggtc   2400
atcctgctct acaccggcaa caccgacacc ctagcccagg tccagtgcct cgccacgccc   2460
gccgacccgt ccgacccgct cctccgcgag tgggtcaagc accccgccaa ccccatcctc   2520
taccctcccc ccggcatcgg cctcaaggac ttccgcgacc ccctcaccgc ctggttcgac   2580
```

-continued

```
cactccgacc acacctggcg caccgtcatc ggctccaagg acgacgacgg ccacgccggc   2640
atcatcctca gctacaagac caaggacttc gtcaactacg agctcatgcc ggggaacatg   2700
caccgcgggc ccgacggcac cggaatgtac gagtgcatcg acctctaccc cgtcggcggc   2760
aactcgtccg agatgctcgg cggcgacgac tcgcccggcg tgctcttcgt gctcaaggag   2820
agcagcgacg acgagcgcca cgactactac gcgctcggaa ggttcgacgc cgtcgccaac   2880
gtttggacgc ccatcgaccg ggagctggac cttgggatcg ggctcagata cgactgggga   2940
aagtactacg cctccaagtc cttctacgac cagaagaaga accgccgcat cgtatgggca   3000
tacatcggcg agaccgactc cgagcaggcc gacatcacca agggatgggc caatctcatg   3060
gtatgcactt gtacaaatcc acatcattct tcttgtactt agtattagta ccttatttgc   3120
atatattctg tcattatcat cctcatkgyt ycatcgccgg cataagcatg gaggacgact   3180
agctaacact attagacgga cgtcttgtcg cttgtttctt tcttgtttaa cggtcacctc   3240
tcggttctac tgtaggcagg tcactatcgt aattagctgc tagctgcctt gttgacacac   3300
atggtgtgcc cgtccccttt ggctctgcct gcctgcatgc atgtcgcatt cagtccctag   3360
ttaaaatcgc agatctacca tcgactactc atatgcctag tgtagtagtg tgtcctttcc   3420
cccagtatag aatttgcttg tatttttgtt aatcgccatg gtaggtgctt gatgctgaac   3480
taatctttta tttacttacc gatcgggaca taggccggct gaatttcaac ggcttgtttt   3540
cttttggtca ctttcatcat tgatctcaca ctgcacctct caagtgtcca ttttcagtct   3600
agtggaaaat tagctagcat tgctccacaa tcgtactcat caacttgttg cttattaaat   3660
tgtttatgtg aagactacga tatcttcttt gttcgtgccg ttgtttcttt aagagaattc   3720
ggtggagggc gcaggccctt tatattgatt acatagacaa gagtagttgt ttgcagtcaa   3780
gttaaataat tgattcatta taacggtaaa tgtatcatcg tgtgtgcaga cgattccaag   3840
aacggtggag cttgacagga agacccgcac aaacctcatc caatggccag tggaggaggt   3900
cgacaccctc cgcaggaact ccacggacct cggtcgcatc accgtcaacg ccggctccgt   3960
cattcgcctc cccctccacc agggcgctca actcgacatc gaggcctcct tccaactcaa   4020
ctcttccnac gtggatgcta tcaacgaggc cgacgtcggc tacaactgca gcaccagtgg   4080
tgccgccgta cggggggcgc tcggcccctt tggcctcctc gtccttgcca acggccgcac   4140
cgaacagacg gctgtgtact tctacgtgtc caagggcgtc gacggtgccc tccagaccca   4200
cttttgccac gacgagtcac ggtcaacgcg ggcaaaggat gtcgtgaata gratgattgg   4260
cagcatcgtg ccggtgcttg acggtagacc ttttcggtga gggtgctagt ggaccactcc   4320
atcgtgcaga gcttcgcgat gggcgggagg atcacggcga cgtcgcgggc gtacccgacg   4380
gaggccatct acgcggccgc gggggtctac ctcttcaaca acgccacggg cgccaccgtc   4440
accgccnaga ggctcgtcgt gcacnanatg gcctcagctg acaaccatat cttcacgaac   4500
gacgacttgt agatgaaacc aagtttagct cgtgttgcat tcttgttaac ggccggtgat   4560
tgcctatcta cacattcatt tggcgttcga ttggtgggtt ccttgatctt gtcatggatg   4620
gggatcgtac aatagttttt gatttggttt tttttttgt atcggggtga tgtatgaaat   4680
tanatgactg tcctaccccc aagtcgtaac tatctgcagg agcccttctg cagtgactat   4740
gatgacagtg tcatctatca actgtatcag attacttaat ttccaaaggg ggtttccttt   4800
taatcgagtc atgggatcc                                                4819
```

<210> SEQ ID NO 12
<211> LENGTH: 653

-continued

```
<212> TYPE: PRT
<213> ORGANISM: Lolium perenne
<220> FEATURE:
<221> NAME/KEY: misc_feature
<222> LOCATION: (493)..(493)
<223> OTHER INFORMATION: Xaa can be any naturally occurring amino acid
<220> FEATURE:
<221> NAME/KEY: misc_feature
<222> LOCATION: (579)..(579)
<223> OTHER INFORMATION: Xaa can be any naturally occurring amino acid
<220> FEATURE:
<221> NAME/KEY: misc_feature
<222> LOCATION: (633)..(633)
<223> OTHER INFORMATION: Xaa can be any naturally occurring amino acid
<220> FEATURE:
<221> NAME/KEY: misc_feature
<222> LOCATION: (639)..(639)
<223> OTHER INFORMATION: Xaa can be any naturally occurring amino acid

<400> SEQUENCE: 12

Met Glu Ser Pro Ser Ala Val Val Pro Gly Thr Thr Ala Pro Leu Leu
1               5                   10                  15

Pro Tyr Ala Tyr Ala Pro Leu Pro Ser Ser Ala Asp Asp Ala Arg Gln
            20                  25                  30

Asn Arg Ser Gly Gly Arg Trp Arg Ala Cys Ala Ala Val Leu Ala Ala
        35                  40                  45

Ser Ala Leu Ala Val Val Val Val Val Gly Leu Leu Ala Gly Gly Arg
    50                  55                  60

Val Asp Arg Val Pro Ala Gly Gly Asp Val Ala Ser Ala Thr Val Pro
65                  70                  75                  80

Ala Val Pro Met Glu Phe Pro Arg Ser Arg Gly Lys Asp Phe Gly Val
                85                  90                  95

Ser Glu Lys Ser Ser Gly Ala Tyr Ser Thr Asp Gly Gly Phe Pro Trp
            100                 105                 110

Ser Asn Ala Met Leu Gln Trp Gln Arg Thr Gly Phe His Phe Gln Pro
        115                 120                 125

Glu Gln His Tyr Met Asn Asp Pro Asn Gly Pro Val Tyr Tyr Gly Gly
    130                 135                 140

Trp Tyr His Leu Phe Tyr Gln His Asn Pro Lys Gly Asp Ser Trp Gly
145                 150                 155                 160

Asn Ile Ala Trp Ala His Ala Val Ser Lys Asp Met Val Asn Trp Arg
                165                 170                 175

His Leu Pro Leu Ala Met Val Pro Asp Gln Trp Tyr Asp Ser Asn Gly
            180                 185                 190

Val Leu Thr Gly Ser Ile Thr Val Leu Pro Asp Gly Gln Val Ile Leu
        195                 200                 205

Leu Tyr Thr Gly Asn Thr Asp Thr Leu Ala Gln Val Gln Cys Leu Ala
    210                 215                 220

Thr Pro Ala Asp Pro Ser Asp Pro Leu Leu Arg Glu Trp Val Lys His
225                 230                 235                 240

Pro Ala Asn Pro Ile Leu Tyr Pro Pro Pro Gly Ile Gly Leu Lys Asp
                245                 250                 255

Phe Arg Asp Pro Leu Thr Ala Trp Phe Asp His Ser Asp His Thr Trp
            260                 265                 270

Arg Thr Val Ile Gly Ser Lys Asp Asp Asp Gly His Ala Gly Ile Ile
        275                 280                 285

Leu Ser Tyr Lys Thr Lys Asp Phe Val Asn Tyr Glu Leu Met Pro Gly
    290                 295                 300

Asn Met His Arg Gly Pro Asp Gly Thr Gly Met Tyr Glu Cys Ile Asp
```

-continued

```
305                 310                 315                 320

Leu Tyr Pro Val Gly Gly Asn Ser Ser Glu Met Leu Gly Gly Asp Asp
                325                 330                 335

Ser Pro Gly Val Leu Phe Val Leu Lys Glu Ser Ser Asp Asp Glu Arg
            340                 345                 350

His Asp Tyr Tyr Ala Leu Gly Arg Phe Asp Ala Val Ala Asn Val Trp
        355                 360                 365

Thr Pro Ile Asp Arg Glu Leu Asp Leu Gly Ile Gly Leu Arg Tyr Asp
    370                 375                 380

Trp Gly Lys Tyr Tyr Ala Ser Lys Ser Phe Tyr Asp Gln Lys Lys Asn
385                 390                 395                 400

Arg Arg Ile Val Trp Ala Tyr Ile Gly Glu Thr Asp Ser Glu Gln Ala
                405                 410                 415

Asp Ile Thr Lys Gly Trp Ala Asn Leu Met Thr Ile Pro Arg Thr Val
            420                 425                 430

Glu Leu Asp Arg Lys Thr Arg Thr Asn Leu Ile Gln Trp Pro Val Glu
        435                 440                 445

Glu Val Asp Thr Leu Arg Arg Asn Ser Thr Asp Leu Gly Arg Ile Thr
    450                 455                 460

Val Asn Ala Gly Ser Val Ile Arg Leu Pro Leu His Gln Gly Ala Gln
465                 470                 475                 480

Leu Asp Ile Glu Ala Ser Phe Gln Leu Asn Ser Ser Xaa Val Asp Ala
                485                 490                 495

Ile Asn Glu Ala Asp Val Gly Tyr Asn Cys Ser Thr Ser Gly Ala Ala
            500                 505                 510

Val Arg Gly Ala Leu Gly Pro Phe Gly Leu Leu Val Leu Ala Asn Gly
        515                 520                 525

Arg Thr Glu Gln Thr Ala Val Tyr Phe Tyr Val Ser Lys Gly Val Asp
    530                 535                 540

Gly Ala Leu Gln Thr His Phe Cys His Asp Glu Ser Arg Ser Thr Arg
545                 550                 555                 560

Ala Lys Asp Val Val Asn Arg Met Ile Gly Ser Ile Val Pro Val Leu
                565                 570                 575

Asp Gly Xaa Thr Phe Ser Val Arg Val Leu Val Asp His Ser Ile Val
            580                 585                 590

Gln Ser Phe Ala Met Gly Gly Arg Ile Thr Ala Thr Ser Arg Ala Tyr
        595                 600                 605

Pro Thr Glu Ala Ile Tyr Ala Ala Ala Gly Val Tyr Leu Phe Asn Asn
    610                 615                 620

Ala Thr Gly Ala Thr Val Thr Ala Xaa Arg Leu Val Val His Xaa Met
625                 630                 635                 640

Ala Ser Ala Asp Asn His Ile Phe Thr Asn Asp Asp Leu
                645                 650


<210> SEQ ID NO 13
<211> LENGTH: 7551
<212> TYPE: DNA
<213> ORGANISM: Lolium perenne
<220> FEATURE:
<221> NAME/KEY: misc_feature
<222> LOCATION: (6782)..(6782)
<223> OTHER INFORMATION: n is a, c, g, or t

<400> SEQUENCE: 13

ggatccggag ctgacggcgg ggtggaaggg agagaagcga tcgatacttt caccgcgttg     60
```

-continued

```
ctaggttttc gcctccacca tgcgaaacaa gcgatgtgca ggatcaaaat gtaaaatcga    120
tcggacgatg gagaggtgga ggtgaagcaa ggccagtgtc ctgcccgtgc gtgccaggag    180
tctatcatgg atagaatgag agggcgcccc gggtgtcgct cttgcttgtt ctaatttagc    240
cacttgttca ccttttgttt ttctcattgc atggttggaa ttcatgatta atttcactat    300
cagttacagt tttggttatc taataatttt atgaaacccc atatctatag acggcttcat    360
caaggttgtg gtgtgcgtta tcaaggttcc attacttttc cccaaaaaaa aaggttccat    420
tgcgttgtta tattcatgtt ttggaccggg tcgtaattca atactcgaat gaccattagt    480
ccatcgatta ccagatttca tgaaaggagt taaatgaagc agtatacata catgcatgta    540
ttttactata tatacagttg tattttacta tatatactat gtaataggga ctttatgcgc    600
acgtgtcctt cttgatggtt aattcacacc gcaatcaaat ttactgagat ggcagcttgt    660
agtaccctga ctgacattac atgaatgcga tggccggcca gtcctctacc ttcttgtttt    720
tgacacttgg cccggtcccc arcattgtac gatgtgttcg tgtcggacaa tcacaatgca    780
tgcatgtctc ttyggggaca tccgatacga tacaggtacc agaagaatgc atgtctagtc    840
ttgacggttc acactkrcat ccgatatgtt cgtttgtgga cgtaatattt ctgaaatatc    900
ttttttcagt atattattta tgaaatttgg ttaaataaat tccgggattt acaccgaatt    960
aatgcatggt tgctgacagt caagcatgca tatatcccgt cttgatggtt cacactgagg   1020
ccggtcccac aaaccagcca aggcatcgcc caactataaa tcacgctcgc tcctcaagag   1080
tgagatcgtc catccatcaa ctttcctcta ttttttcgaa cacgatgaag tcacgcgcca   1140
ccccgcctcg tctgatccag tgcgtgtcgc tgcacctcca ccgtactagc ggcggcgcga   1200
cgaggtggcg cgcgtgcaca accaccgtgc tggccgtggg cgtgctcgcc cacgcgctcg   1260
caggggccgg cgaaataatg gcgtggtggc tcggcgccgg gaagggcgcg gatgggttcc   1320
cgtggaccag cgcgatgctg cagtggcagc gcaccgggtt ccatttccag cccgagaaga   1380
attttatgag cggtagtaca ggagtagttg attatttatt tttctctggc aatctgtacg   1440
tgcagaaact gactgactga ctggctttct tgtttgtttg ctcgtggcag atcccagcgg   1500
ttagtacgta catcactttc tttgtttttg ttgaactggg aagtttatat tgattagtaa   1560
caacatctta cagagtatta attaagggga gtgctgggcg tcccccggcg gattagaaat   1620
ctaatcccac gggtccccaa ccatccgatc aacagatctg gaacgttttc ggccgtcaga   1680
tcaaaccaac cagccctctc ttccactttt actaccatga tgaaccaaag tagcaaaaaa   1740
cggttcaatt gtagcaaaat ctattttcac ctaaaaacac agacctcgcc ggagatgtcg   1800
ccggagacct cgccggagaa cttgtagcaa aaaacatata ctattatagc taaaacctag   1860
aacaaatgta gcaaaacctg attccgccgg atactcgcag gagacatagt agcaaagaaa   1920
atatggtata gtagcaagaa aacaaaaata ttgtagcaaa tttttttgc tattgtagca   1980
aactatgcat tgatgaaaaa tataattgta gtaagacaaa tttcgccaaa aagaattgta   2040
gcaaacaatg tatactatat taacataaat gccaaactaa agtagcaaaa acaatatatt   2100
attgtagcat cacgccccga agcaaaaacg cccaggagcc gttggcagca ggcggccgtt   2160
gacttgcagc tagagggtag gggggagagg aggatgacsg ccatggctgg gcgtgcttgc   2220
agtgggagga ataggcggag gaagtaggag gcggctgccg ccgcgcgtag gggaggcggc   2280
acgcggagct cgctatgagg gctgacgacg gagtcggcgg aggaggtcag gggagggcgg   2340
cggccgccgt tcgcagaggg tgctcgaggc agctcgcgga ccttggcgtg gcggcgggcg   2400
gcggctgctg cagtggggtt ggcggcagtg gcgccgcaca gcagaatcgc gtgtaggtgg   2460
```

-continued

```
tcgcgggacg ccgccggtcg cccggggatg cagggtggag gcgcgggacg ccgccgtagt   2520
tcgggatgca ggggaggagg cggagtggca cgctatggag gaagttgcgg cggcacgccg   2580
ggtcagcggc acccggcacg tggcttgcgc ggcgggctgg ctcgacgcgt tgctgggttg   2640
gcggtggctc gtggcagggc gacgacggcg gcgcgacagc ctacctgtgc ggttgctcga   2700
tttggggatg agattgaaac cagaaaaaaa gggatgaagg ggaagacgat aacgtgggtg   2760
ggtcccacgg gacacgtggc atacgggggga atcggaggaa tggagcgctg atcccccggg   2820
ggttcggcag cgtttcccat taattaattg acttgatgat gcaggtccgg tgtactaccg   2880
tggatggtac cacctattct accaatacaa cccggagggc accgtggggg ccaacatcac   2940
gtggggccac gccgtgtccc gggatctcgt ccactggcgc cacctccctc tcgccatgct   3000
ccctgaccgg tggtacgaca tcaacggcgt ttggaccggc tccgccacca tgctccccaa   3060
cgggacgctc acaatgctct acacggggtc caccaatgcc tctacccagg tccagtgcct   3120
cgccgtcccc gcaaacccca acgactccct cctccgcaac tggacaaagc accctgccaa   3180
ccccgtcctc ctcccgcccc ccggcatcgg cgataaggac ttccgtgacc ccaccaccgc   3240
ctggttccac aagtcagact ccacctggca catcgccatc gggtccaagg atgaccacgg   3300
ccactccggc atcgccatca cgtacaagac caaagacttt gttagctacg agctcatccc   3360
gggattcttg catcgtgtcg agagcactgg catgtgggag tgcgttgact tctaccccgt   3420
cggcagccgc gaccaagacg ccgagaactc gtcggaggag ctgttgtacg tgatgaaggc   3480
gagcatggac gaccaccggc acgactgcta cgcattgggg aggtacgacg ctgaggcaaa   3540
catatggacg ccggtggacc ctgaggcgga cgtggggatc gggctgaggt acgactgggg   3600
aaggtttttt gcgtccaaaa cgttctatga tccggcgaag cggcggcgcg tgctgttggg   3660
gtatgtcgcc gaggccgact ccgagttggc cgacgtggcc aagggatggg cttgcctcca   3720
ggtatctcta tactatacat cgctatgatt gtgttttacc ttgcattttg catcaatagc   3780
tccatccttc atttcgttac tcatgttaga ttgatacatc agtgcatcgc ctcttgggga   3840
ttgaaatgct atctgttgtt atatcagtgc atgcatgcat catacaatcc atcttctctt   3900
ttgtgcaata caacctgctt aaaatgttga ttaatgcatg gctgatggct ttctgggaaa   3960
acttgttaat cacattgtta atatattcta atgcgagaag agaggaactt gtggctgcta   4020
attagtcgtg gatggtgtcg cagtcatgga cgagtactag ttgcactcgc tccgtatggt   4080
ccgctggtat tttttttttt taaaattgac catcaatttg atcaacaaaa tatgagttat   4140
attttacaaa aattataccg ttagaaactc tttttaaata tgaatccaat gttatatttt   4200
tttacagtat tactcatata tggttgacaa aatttgtggt cagagttttt cttaaaatac   4260
gtgcatgctt tataaaccca tacggaggta gtacatcgct acatcgcagt ctcatcgttt   4320
caggtttcta tcttttttct tttgggaaaa ttctttcttg tttaacggcc aataatagct   4380
gcatgatgca tgataatatt tttttattaa tcctcgtgga aggtataggc cggccgggtg   4440
aatttcaagg gtacctttct ttgatcactt tcatcatgtc tttgcatctt ccaagaacca   4500
atgagtgccc atcaagtgtc cattttccgc gtaattccaa attaactagt acgtgccacg   4560
tatcgtgcgg aaagcacgat accagctatc tacaaaccac ctkratgtta tggtgaatca   4620
tgcatgtagt caaaaaacta gtacgtgcca cgtcagtcgc acttggaacc atgtatttaa   4680
ggctcagttt gcggttccta aactgtgcta tgctggactt attttataat catctctgaa   4740
acaatagatt gaccacaaga tatcaggact ttcttcctta attccctctt tccttcctat   4800
```

-continued

```
ctgttacggt acatggtcgt gccgacgtgg gactgactca tcaacctcga gttttggaag   4860
ttgcttatgt aaagtgttcg attcttttag gctagccata gtggtagtat cttagctagt   4920
atcatgcaca ttggttccac aaaaatactg atgtggcagc taattaagga ggakasatra   4980
gakkmgagya tcataggtgg ataccgtatc atagcgcata tcacgagaaa agttaatgtc   5040
aaacaaatct tgtacatcaa tttgcattga gattctaaat agcaataaat atagcataac   5100
tatgatacta cttcatgata ctacccacta tagggataat atcatacaca agtatcatat   5160
gcatgatact actatatgat acttagcact atggccagcc ttatggaaat tggtggagga   5220
cgccagcacc tttattaatt gaataacaat aatttttatc atgttttttt ttcaagttca   5280
ttatgtcaat gtgcattcat aatcgatgga cttacctcgc ttgaattatt gaactaacta   5340
attaatggtc tatgacatgt gtgcagtcga ttccgaggac ggtggcgttg gatgagaaga   5400
cccggatgaa tctcctccaa tggccggtgg aaggaatcga gaccctccgc ctcaatacca   5460
tcgaccttgg caacatcacc atcggcaccg gctccatctt ccccctcccc ctccggcaag   5520
ccactcagct cgacatggag gcctccttcc gcctagacgc wtccgccata gctgccttca   5580
atgaggtcga cgttagctac aactgcagca ccagtggcgg tgccgctagc cgtggcacgc   5640
tcggcccctt cggcctccta gtcctcacca ccgccgacag tcgcagcgaa caaatggcag   5700
tgtacttcta cgtgtccaag agcatcgacg gcacgctcca gaccagcttc tgccacgacg   5760
agtcccgctc gtctcgggcc tgggacgtgg tgaagcgggt ggtgggcagc accgtgccgg   5820
tgctccacgg tgaggcttta tctgtcaggg tgctcgtgga tcattcgatc gtagagagct   5880
tcgcgatggg cgggaggtca acggtgacgt cgcgggtata cccgacggag gccatctacg   5940
aggcggcgag ggcgtatgtt ttcaacaacg ccaccggctc cactgtcacc gtcgagagac   6000
tcgtggtgca cgatatggac tcggcattca tcaaataaag agaacaataa ttttctgagc   6060
ctagtatcca catgatcatg atatagtaag ggaaaaatca tatctataag tttccgaact   6120
tagtgaaaaa aaacctgtaa aagatatgca gtcatataca catgtgaaat taggtaggaa   6180
aatatgataa tctcgtagat gaggaaaaaa tattgtacac caaactattg taagttacag   6240
taatgtaatg taaaaaaagt ttttaagtta cagaaggtac ataccgcaaa taatcatatt   6300
attttaccaa gatatttttt tctggagtat tcctttcaag tatcttttat ctctagaatc   6360
ttctccaatc atgagtggca accgaaatgg agctcctgtg ttgctccccg tgtctcaccc   6420
ctttcggccc cactgtcatt gggtggacct attctcacgg cggctgtcct gagaaacaaa   6480
aatagcagct gaaatgaaga cacggcgaca cgcaagccag catctctcat tgaacctgcg   6540
gagtgagata gctctcgtgg cgctgctcta cttgacgcgt ttgtctcata caacagcgca   6600
tggctccttc atgtcaggtc catgatccac agatggtatg attgggtttg gaacattttt   6660
tgggtttgtg atatgtcgta gatacaaagg gaaatgtctg aagcatgcat ggatggggtt   6720
ccctgctcat gtactcaatg ttgatggatc tgaawccggg ataggttttg cttctgtctt   6780
gnatttctct tcatggattt tctccaatga ttttttaatg atttgtttat catggacttg   6840
taggttagtt catggaatat attttttgca ttggtttgct agatttatca attttcatct   6900
gctgatagtc catatgaaca atgggtttgg tacagatcga aattcaaatt catggtgttt   6960
ttgtaaaaaa tatcttttcc ttcccagttt ttctatgatg ttaataatgc atgtatgctc   7020
atggaaccgg tggactgatg caggtatgca gattcgttgc aaacagaatt ggcttcatca   7080
ttgcttagaa tttgaggaag catggttccg agttgatgtc atttcttaga atctgatcta   7140
atgcatacaa gaaaaggtct actaaatttt ttgacgtttc aacaaggtag aatccaacgg   7200
```

-continued ttggacgccc agttggttgt ggttttgcag ttttggctac ctctaggcga tcgctgcttg 7260
tcctcttcat ttttgttcct cggggggttt cgcggcggct ttttgcggtg cgcggctggg 7320
tgcggtagat ttgttggcga gcgtagattg tttactgagt ttttttcttc tttgaattgt 7380
gagctacaac tgtttgttga ggtgcatagt tatcattgat cagttttgtg tttggtgcag 7440
ttcgggtaga gaacaagatg ccaggtgctc tatagcttct tcattttgag acattatggc 7500
tttggggtcg accccggtaa caaaaaaggg atgcataaaa acttgggatc c 7551

<210> SEQ ID NO 14
<211> LENGTH: 653
<212> TYPE: PRT
<213> ORGANISM: Lolium perenne

<400> SEQUENCE: 14

Met Val Ala Asp Ser Gln Ala Cys Ile Tyr Pro Val Leu Met Val His
1 5 10 15

Thr Glu Ala Gly Pro Thr Asn Gln Pro Arg His Arg Pro Thr Ile Asn
20 25 30

His Ala Arg Ser Ser Arg Val Arg Ser Ser Ile His Gln Leu Ser Ser
35 40 45

Ile Phe Ser Asn Thr Met Lys Ser Arg Ala Thr Pro Pro Arg Leu Ile
50 55 60

Gln Cys Val Ser Leu His Leu His Arg Thr Ser Gly Gly Ala Thr Arg
65 70 75 80

Trp Arg Ala Cys Thr Thr Thr Val Leu Ala Val Gly Val Leu Ala His
85 90 95

Ala Leu Ala Gly Ala Gly Glu Ile Met Ala Trp Trp Leu Gly Ala Gly
100 105 110

Lys Gly Ala Asp Gly Phe Pro Trp Thr Ser Ala Met Leu Gln Trp Gln
115 120 125

Arg Thr Gly Phe His Phe Gln Pro Glu Lys Asn Phe Met Ser Asp Pro
130 135 140

Ser Gly Pro Val Tyr Tyr Arg Gly Trp Tyr His Leu Phe Tyr Gln Tyr
145 150 155 160

Asn Pro Glu Gly Thr Val Gly Ala Asn Ile Thr Trp Gly His Ala Val
165 170 175

Ser Arg Asp Leu Val His Trp Arg His Leu Pro Leu Ala Met Leu Pro
180 185 190

Asp Arg Trp Tyr Asp Ile Asn Gly Val Trp Thr Gly Ser Ala Thr Met
195 200 205

Leu Pro Asn Gly Thr Leu Thr Met Leu Tyr Thr Gly Ser Thr Asn Ala
210 215 220

Ser Thr Gln Val Gln Cys Leu Ala Val Pro Ala Asn Pro Asn Asp Ser
225 230 235 240

Leu Leu Arg Asn Trp Thr Lys His Pro Ala Asn Pro Val Leu Leu Pro
245 250 255

Pro Pro Gly Ile Gly Asp Lys Asp Phe Arg Asp Pro Thr Thr Ala Trp
260 265 270

Phe His Lys Ser Asp Ser Thr Trp His Ile Ala Ile Gly Ser Lys Asp
275 280 285

Asp His Gly His Ser Gly Ile Ala Ile Thr Tyr Lys Thr Lys Asp Phe
290 295 300

Val Ser Tyr Glu Leu Ile Pro Gly Phe Leu His Arg Val Glu Ser Thr

-continued

```
305                 310                 315                 320

Gly Met Trp Glu Cys Val Asp Phe Tyr Pro Val Gly Ser Arg Asp Gln
                325                 330                 335

Asp Ala Glu Asn Ser Ser Glu Glu Leu Leu Tyr Val Met Lys Ala Ser
            340                 345                 350

Met Asp Asp His Arg His Asp Cys Tyr Ala Leu Gly Arg Tyr Asp Ala
        355                 360                 365

Glu Ala Asn Ile Trp Thr Pro Val Asp Pro Glu Ala Asp Val Gly Ile
    370                 375                 380

Gly Leu Arg Tyr Asp Trp Gly Arg Phe Phe Ala Ser Lys Thr Phe Tyr
385                 390                 395                 400

Asp Pro Ala Lys Arg Arg Arg Val Leu Leu Gly Tyr Val Ala Glu Ala
                405                 410                 415

Asp Ser Glu Leu Ala Asp Val Ala Lys Gly Trp Ala Cys Leu Ser Ile
            420                 425                 430

Pro Arg Thr Val Ala Leu Asp Glu Lys Thr Arg Met Asn Leu Leu Gln
        435                 440                 445

Trp Pro Val Glu Gly Ile Glu Thr Leu Arg Leu Asn Thr Ile Asp Leu
    450                 455                 460

Gly Asn Ile Thr Ile Gly Thr Gly Ser Ile Phe Pro Leu Pro Leu Arg
465                 470                 475                 480

Gln Ala Thr Gln Leu Asp Met Glu Ala Ser Phe Arg Leu Asp Ala Ser
                485                 490                 495

Ala Ile Ala Ala Phe Asn Glu Val Asp Val Ser Tyr Asn Cys Ser Thr
            500                 505                 510

Ser Gly Gly Ala Ala Ser Arg Gly Thr Leu Gly Pro Phe Gly Leu Leu
        515                 520                 525

Val Leu Thr Thr Ala Asp Ser Arg Ser Glu Gln Met Ala Val Tyr Phe
    530                 535                 540

Tyr Val Ser Lys Ser Ile Asp Gly Thr Leu Gln Thr Ser Phe Cys His
545                 550                 555                 560

Asp Glu Ser Arg Ser Ser Arg Ala Trp Asp Val Val Lys Arg Val Val
                565                 570                 575

Gly Ser Thr Val Pro Val Leu His Gly Glu Ala Leu Ser Val Arg Val
            580                 585                 590

Leu Val Asp His Ser Ile Val Glu Ser Phe Ala Met Gly Gly Arg Ser
        595                 600                 605

Thr Val Thr Ser Arg Val Tyr Pro Thr Glu Ala Ile Tyr Glu Ala Ala
    610                 615                 620

Arg Ala Tyr Val Phe Asn Asn Ala Thr Gly Ser Thr Val Thr Val Glu
625                 630                 635                 640

Arg Leu Val Val His Asp Met Asp Ser Ala Phe Ile Lys
                645                 650
```